United States Patent
Yamagishi et al.

(10) Patent No.: US 11,154,544 B2
(45) Date of Patent: Oct. 26, 2021

(54) AMIDE DERIVATIVES AS NAV1.7 AND NAV1.8 BLOCKERS

(71) Applicant: RaQualia Pharma Inc., Aichi (JP)

(72) Inventors: Tatsuya Yamagishi, Aichi (JP); Mikio Morita, Aichi (JP); Yuji Shishido, Aichi (JP); Ryuichi Yamaguchi, Aichi (JP); Norikazu Gaja, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 259 days.

(21) Appl. No.: 16/301,691

(22) PCT Filed: Jun. 20, 2018

(86) PCT No.: PCT/JP2018/023412
§ 371 (c)(1),
(2) Date: Nov. 14, 2018

(87) PCT Pub. No.: WO2018/235851
PCT Pub. Date: Dec. 27, 2018

(65) Prior Publication Data
US 2020/0016135 A1 Jan. 16, 2020

Related U.S. Application Data

(60) Provisional application No. 62/522,215, filed on Jun. 20, 2017.

(51) Int. Cl.
A61K 31/444 (2006.01)
A61K 31/506 (2006.01)
A61K 31/44 (2006.01)
A61K 31/4709 (2006.01)
A61K 31/505 (2006.01)
C07D 213/81 (2006.01)
C07D 401/12 (2006.01)
C07D 239/28 (2006.01)

(52) U.S. Cl.
CPC ............ *A61K 31/444* (2013.01); *A61K 31/44* (2013.01); *A61K 31/4709* (2013.01); *A61K 31/505* (2013.01); *A61K 31/506* (2013.01); *C07D 213/81* (2013.01); *C07D 239/28* (2013.01); *C07D 401/12* (2013.01)

(58) Field of Classification Search
CPC .. A61K 31/506; A61K 31/44; A61K 31/4709; A61K 31/505; C07D 491/107; C07D 498/04; C07D 487/04; C07D 413/12; C07D 403/12; C07D 405/14
USPC ........................................................ 514/210
See application file for complete search history.

(56) References Cited

U.S. PATENT DOCUMENTS

| | | |
|---|---|---|
| 2009/0270413 A1 | 10/2009 | Galemmo, Jr. et al. |
| 2015/0291582 A1 | 10/2015 | Kawamura et al. |
| 2017/0029416 A1 | 2/2017 | Adamski-Werner et al. |

FOREIGN PATENT DOCUMENTS

| | | |
|---|---|---|
| WO | 2006/027052 | 3/2006 |
| WO | 2006/058905 | 6/2006 |
| WO | 2008011131 | * 1/2008 |
| WO | 2010/137351 | 12/2010 |
| WO | 2012/053186 | 4/2012 |
| WO | 2012053186 | * 4/2012 |
| WO | 2015/144657 | 10/2015 |
| WO | 2017/012966 | 1/2017 |

OTHER PUBLICATIONS

Cummins et al., "The roles of sodium channels in nociception: Implications for mechanisms of pain", Pain, vol. 131: pp. 243-257 (2007).
Dib-Hajj et al., "The $Na_v1.7$ sodium channel: from molecule to man", Nature Reviews | Neuroscience, vol. 14: pp. 49-62 (2013).
Hong et al., "Early Painful Diabetic Neuropathy Is Associated with Differential Changes in Tetrodotoxin-sensitive and -resistant Sodium Channels in Dorsal Root Ganglion Neurons in the Rat", J Biol Chem., vol. 279, No. 28: pp. 29341-29350 (2004).
Nassar et al., "Nociceptor-specific gene deletion reveals a major role for $Na_v1.7$ (PN1) in acute and inflammatory pain", PNAS, vol. 101, No. 34: pp. 12706-12711 (2004).
Minett et al., "Pain without Nociceptors? Nav1.7-Independent Pain Mechanisms", Cell Reports, vol. 6: pp. 301-312 (2014).
Gingras et al., "Global Nav1.7 Knockout Mice Recapitulate the Phenotype of Human Congenital Indifference to Pain", PLOS One, vol. 9, Issue 9, e105895: (2014).
Waxman et al., "Sodium channel genes in pain-related disorders: phenotype-genotype associations and recommendations for clinical use", Lancet Neurol, vol. 13: pp. 1152-1160 (2014).

(Continued)

*Primary Examiner* — Tracy Vivlemore
*Assistant Examiner* — Ebenezer O Sackey
(74) *Attorney, Agent, or Firm* — Wenderoth, Lind & Ponack, L.L.P.

(57) ABSTRACT

The present invention relates to amide derivatives which have blocking activities of voltage gated sodium channels as the Nav1.7 and Nav1.8 channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

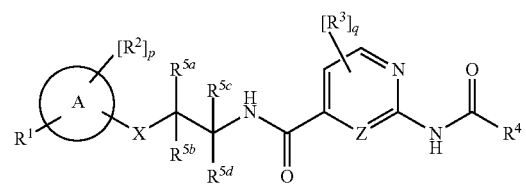

12 Claims, No Drawings

(56) References Cited

OTHER PUBLICATIONS

Coggeshall et al., "Differential expression of tetrodotoxin-resistant sodium channels $Na_v1.8$ and Nav1.9 in normal and inflamed rats", Neuroscience Letters, vol. 355: 45-48 (2004).
Akopian et al., "The tetrodotoxin-resistant sodium channel SNS has a specialized function in pain pathways", Nature Neuroscience, vol. 2, No. 6: pp. 541-548 (1999).
Kerr et al., "A role for the TTX-resistant sodium channel Nav 1.8 in NGF-induced hyperalgesia, but not neuropathic pain", NeuroReport, vol. 12, No. 14: pp. 3077-3080 (2001).
Joshi et al., "Involvement of the TTX-resistant sodium channel Nav 1.8 in inflammatory and neuropathic, but not post-operative, pain states", Pain, vol. 123: pp. 75-82 (2006).
Dong et al., "Small Interfering RNA-Mediated Selective Knockdown of $Na_v$ 1.8 Tetrodotoxin-Resistant Sodium Channel Reverses Mechanical Allodynia in Neuropathic Rats", Neuroscience, vol. 146: pp. 812-821 (2007).
Faber et al. "Gain-of-function $Na_v1.8$ mutations in painful neuropathy", PNAS, vol. 109, No. 47: pp. 19444-19449 (2012).
Lee et al., "A Monoclonal Antibody that Targets a $Na_v1.7$ Channel Voltage Sensor for Pain and Itch Relief", Cell, vol. 157: pp. 1393-1404 (2014).
International Preliminary Report on Patentability dated Jan. 2, 2020 in International (PCT) Patent Application No. PCT/JP2018/023412.
International Search Report, dated Aug. 28, 2018 in corresponding International Patent Application No. PCT/JP2018/023412
Examination Report dated Apr. 20, 2021 in corresponding Indian Patent Application No. 201927047321.
Russian Office Action dated Aug. 4, 2021 in corresponding Russian Patent Application No. 2019133530, with English translation.
Belikov, V.G., "Relationship between the Chemical Struccture, Properties of the Compound, and Their Effect on a Living Body", Farmatsevitcheskaya Khimiya (Pharmaceutical Chemistry), Moscow, MEDpress-Inform, 2007, pp. 27-29, with English translation.
Berge. S. M. et al., "Pharmaceutical Salts", Journal of Pharmaceutical Sciences, Jan. 1977, vol. 66, No. 1, pp. 1-19.
English version of https://official.academic.ru/28407/%D0%A4% D0%B0%D1%B0%D0%BC%D0%B0%D1%86%D0%B5%D0% B2%D1%82%D0%B8%D1%87%D0% B5%D1%81%D0%BA% D1%8F%_%D0%BA%D0%BE%D0%BC%D0%BF%D0%BE% D0%B7%B8%D1%86%D0%B8%D1%8F, Wayback Internet Archive Machine, Apr. 12, 2013.
Strickland, I.T. et al. "Changes in the expression of $Na_v1.8$ and $Na_v1.9$ in a distinct population of dorsal root ganglia innervating the rat knee joint in a model of chronic inflammatory joint pain", European Journal of Pain, 2008, vol. 12, No. 5, pp. 564-572.

\* cited by examiner

AMIDE DERIVATIVES AS NAV1.7 AND NAV1.8 BLOCKERS

TECHNICAL FIELD

The present invention relates to the amide derivatives which are sodium channel blockers and have a number of therapeutic applications, particularly in the treatment of pain.

BACKGROUND ART

The amide derivatives of the present invention are sodium channel blockers and have a number of therapeutic applications, particularly in the treatment of pain. More particularly, the amide derivatives of the invention are modulators of both Nav1.7 and Nav1.8 channel. In the discussion that follows, the invention is exemplified by reference to the inhibition of Nav1.7 and Nav1.8 channel. They show the affinity for Nav1.7 and Nav1.8 channel which is significantly greater than their affinity for Nav1.5 channel. The amide derivatives of the invention show good selectivity for the Nav1.7 and Nav1.8 channel as compared with Nav1.5 channel.

The Voltage-gated sodium channels (VGSCs, Nav1.x) have crucial role in initiation and propagation of action potentials in excitable tissues. The VGSCs are integral plasma membrane proteins composed of a large alpha-subunit and one or more smaller beta-subunits. In human, nine alpha-subunits (Nav1.1-Nav1.9) have been identified with distinct biophysical properties and expression profiles. Nav1.7, Nav1.8 and Nav1.9 are expressed predominantly in the peripheral nervous system (NPL1). The biophysical characteristics of Nav1.7 propose a role in initiation of action potentials, while Nav1.8 is a major contributor to the upstroke of action potentials. Nav1.9 creates a persistent current that is involved in setting the resting membrane potential.

Nav1.7 is highly expressed in dorsal root ganglion (DRG) neurons, as well as in sympathetic neurons, and their expression extends to both central and peripheral axonal terminal. Nav1.7 is up-regulated in preclinical models of inflammatory and neuropathic pain, including diabetic neuropathy (NPL 2 and NPL 3). The role of Nav1.7 in pain has been confirmed in knockout studies. In a conditional Nav1.7 knockout mouse, which Nav1.7 is selectively knockout in Nav1.8-positive sensory neurons, inflammatory pain responses evoked by arrange of stimuli, such as formalin, complete Freund's adjuvant (CFA), or nerve growth factor (NGF), were reduced or abolished. However, neuropathic pain developed normally (NPL 4 and NPL 5). A conditional ablation of Nav1.7 in both sensory and sympathetic neurons or global deletion of Nav1.7 recapitulated the pain-free phenotype seen in channelopathy-associated congenital insensitivity to pain (CIP) patients, abolishing inflammatory or neuropathic pain without causing any abnormal autonomic dysfunction (NPL 5 and NPL 6).

In human, mutations in SCN9A, which encodes Nav1.7, are associated with three pain disorders; inherited erythromelalgia (IEM), paroxysmal extreme pain disorder (PEPD) and channelopathy-associated congenital insensitivity to pain (CIP). Gain-of-function mutations, enhancing channel activity and increasing the excitability of DRG neurons, produce severe pain syndromes: inherited erythromelalgia (IEM) or paroxysmal extreme pain disorder (PEPD). In contrast, loss-of-function mutations, causing a complete loss of functional Nav1.7 by channel truncation, miss-splicing or defective trafficking, lead to inability to feel pain: channelopathy-associated congenital insensitivity to pain (CIP) (NPL 7).

Nav1.8 is highly expressed in both non myelinated small C-fiber and thinly myelinated A-delta fiber DRG neurons and their expression level is significantly elevated in inflammatory condition (NPL 8). Several lines of evidences have indicated that Nav1.8 carries most of sodium current underlying the upstroke of action potential in nociceptive neurons. Global Nav1.8 knockout mouse demonstrated the reduction in pain responses to cold stimuli and mechanical pressure, but normally development neuropathic pain (NPL 9 and NPL 10). Knockdown studies using Nav1.8 antisense or siRNA, however, suggested the involvement of Nav1.8 in both neuropathic pain and inflammatory pain (NPL 11 and NPL 12). In human, gain-of-function mutations in SCN10A, which encode Nav1.8, were recently identified in patients with small-fiber neuropathy (SFN) who did not carry mutations in Nav1.7 (NPL 6 and NPL 13). A monoclonal antibody that targets a Nav1.7 channel voltage sensor for pain and itch relief is described. (NPL 14).

Clinically, voltage-gated sodium channel blocker (e.g. lidocaine, halothane) have used in the management of pain, but their utility is often limited by incomplete efficacy owing to low potency and by unwanted side effects due to non-subtype selective, especially against Nav1.5 (e.g., cardiac arrhythmia). Nav1.7 and Nav1.8 are co-expressed in peripheral nerve system and transducing painful signals by functioning in tandem, with Nav1.7 acting as threshold current, and with Nav1.8 producing the majority of sodium current underlying the upstroke of action potential during repetitive firing. Therefore, sodium channel blacker with higher affinity for both Nav1.7 and Nav1.8 than Nav1.5 may offer more favorable clinical profile than existing drugs.

CITATION LIST

Non Patent Literature

{NPL 1} Cummins T R, et al. Pain 2007; 111:243-257
{NPL 2} Dib-Hajj S D, et al. Nat Rev Neurosci. 2013; 14: 49-62
{NPL 3} Hong S, et al. Journal of Biological Chemistry. 2004; 279: 29341-29350
{NPL 4} Massar M A, et al. PNAS 2004; 101: 12706-12711
{NPL 5} Minett M S, et al. Cell Report 2014; 6: 301-312
{NPL 6} Gingras J, et al. PLOS ONE 2014; 9: e105895
{NPL 7} Waxman S G, et al. Lancet Neurol 2014; 13: 1152-1160
{NPL 8} Coggeshal R E, et al. Neuroscience Letters 2004; 355: 45-48
{NPL 9} Akopian A N, et al. Nat Neurosci 1999; 2: 541-548
{NPL 10} Kerr B J. et al. Neuroreport 2001; 12: 3077-3080
{NPL 11} Joshi S K. et al. Pain 2006; 123: 75-82
{NPL 12} Dong X W. et al. Neuroscience 2007; 146: 812-821
{NPL 13 } Faber C G, et al. PNAS 2012; 109: 19444-19449
{NPL 14} Lee J H, et al. Cell. 2014; 157, 1393-1404

SUMMARY OF INVENTION

Technical Problem

It is an objective of the invention to provide new Nav1.7 and Nav1.8 channel blockers that are good drug candidates.

Preferred compounds bind potently to the Nav1.7 and Nav1.8 channels whilst showing little affinity for other sodium channels, particularly the Nav1.5 channel. They possess favorable pharmacokinetic properties, such as absorption, distribution, metabolism and excretion, for the treatment of a condition or disorder in which Nav1.7 and Nav1.8 channel blockers are involved. They are non-toxic and demonstrate few side-effects. Furthermore, the ideal drug candidate will exist in a physical form that is stable, non-hygroscopic and easily formulated.

In particular, the amide derivatives of the present invention are selective for the Nav1.7 and Nav1.8 channels over the Nav1.5 channel, leading to improvements in the side-effect profile.

The amide derivatives of the present invention are therefore useful in the treatment of a wide range of disorders, particularly pain, acute, pain, chronic pain, neuropathic pain, inflammatory pain, visceral pain, nociceptive pain including post-surgical pain, and mixed pain types involving the viscera, gastrointestinal tract, cranial structures, musculo-skeletal system, spine, urogenital system, cardiovascular system and CNS (central nervous system), including cancer pain, back pain, orofacial pain and chemo-induced pain.

Other conditions that may be treated with the amide derivatives of the present invention include pruritus, multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke, cancer pain, seizure disorder and causalgia.

The compounds show activities against Nav1.7 and Nav1.8 channels. In addition, they show selectivity for the Nav1.7 and Nav1.8 channels as compared with Nav1.5 channel.

Solution to Problem

For The treatment of a condition or disorder in which Nav1.7 and Nav1.8 channel blockers are involved, with respect to other compounds disclosed in the art, the compounds of the present invention may show less toxicity; favorable absorption, distribution, metabolism and excretion; favorable solubility; favorable plasma protein binding; less drug-drug interaction; reduced inhibitory activity at HERG channel; and/or reduced QT prolongation.

This invention provides:
[1] a compound of the following formula (I):

[Chem.1]

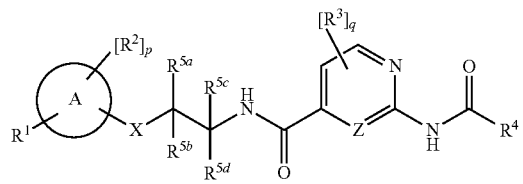

(I)

Wherein:
A is aryl or heteroaryl;
$R^1$ is selected from the group consisting of: —$CF_3$, —$CHF_2$, —$OCF_3$, —$SF_5$, —$OCHF_2$, —$OCH_2CHF_2$, —$OCH_2CF_3$, —$OCH_2CH_2CF_3$, —$OCH(CH_3)CF_3$, —$OCH_2C(CH_3)F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, —$OCH_2CH_2OCF_3$, and fluorobenzyloxy;
$R^2$ is independently selected from the group consisting of:
(1) hydrogen, (2) halogen, (3) hydroxyl, (4) $C_{1-6}$ alkyl, (5) —O—$C_{1-6}$ alkyl, (6) $C_{2-6}$ alkenyl, (7) $C_{3-7}$ cycloalkyl, (8) —CN, and (9) —(C=O)—$NR^6R^7$, wherein the $C_{1-6}$ alkyl, the —O—$C_{1-6}$ alkyl, the $C_{2-6}$ alkenyl or $C_{3-7}$ cycloalkyl is unsubstituted or substituted with one or more substituents independently selected from the group consisting of: halogen, and hydroxyl;
$R^1$ and $R^2$ may be the same or different;
p is 0, 1, 2, 3 or 4;
when p is two or more, each $R^2$ is the same or different;
$R^1$ and $R^2$ may be substituted anywhere on the A ring;
X is selected from the group consisting of: —$CR^{8a}R^{8b}$—, —O—, —O—$CR^{8a}R^{8b}$—, —$NR^9$—, —$NR^9$—$CR^{8a}R^{8b}$—, —S—, and —S—$CR^{8a}R^{8b}$—;
Z is CH, $CR^3$, or N;
$R^3$ is independently selected from the group consisting of:
(1) hydrogen, (2) halogen, (3) hydroxyl, (4) $C_{1-6}$ alkyl, and (5) —O—$C_{1-6}$ alkyl;
q is 0, 1, 2, or 3; when q is two or more, each $R^3$ is the same or different;
$R^4$ is selected from the group consisting of:
(1) hydrogen, (2) $C_{1-6}$ alkyl, (3) $C_{2-6}$ alkenyl, (4) $C_{3-7}$ cycloalkyl, wherein the $C_{1-6}$ alkyl, the $C_{2-6}$ alkenyl or the $C_{3-7}$ cycloalkyl is unsubstituted or substituted with one or more substituents independently selected form the group consisting of: halogen, hydroxyl, —$C_{1-6}$ alkyl, —O—$C_{1-6}$ alkyl, and $C_{3-7}$ cycloalkyl, and (5) aryl which is unsubstituted or substituted with one or more substituents independently selected from the group consisting of: halogen, hydroxyl, $C_{1-6}$ alkyl, —O—$C_{1-6}$ alkyl, —$C_{3-7}$ cycloalkyl, and —O—$C_{3-7}$ cycloalkyl;
$R^{5a}$ and $R^{5c}$ are independently selected from the group consisting of:
(1) hydrogen, (2) halogen, (3) hydroxyl, (4) $C_{1-6}$ alkyl, (5) —O—$C_{1-6}$ alkyl, and (6) $C_{1-6}$ alkoxy$C_{1-6}$ alkyl, wherein the $C_{1-6}$ alkyl, the —O—$C_{1-6}$ alkyl, and the $C_{1-6}$ alkoxy$C_{1-6}$ alkyl is unsubstituted or substituted with one or more substituents independently selected from the group consisting of: halogen and hydroxyl;
$R^{5b}$ and $R^{5d}$ are independently selected from the group consisting of: (1) hydrogen, (2) halogen, and (3) $C_{1-6}$ alkyl;

$R^{5a}$ may form a $C_{3-6}$ cycloalkyl with $R^{5b}$;
$R^{5c}$ may form a $C_{3-6}$ cycloalkyl with $R^{5d}$;
$R^6$ and $R^7$ are independently selected from the group consisting of: (1) hydrogen, (2) $C_{1-6}$ alkyl, and (3) $C_{1-6}$ alkoxy$C_{1-6}$ alkyl, wherein the $C_{1-6}$ alkyl or the $C_{1-6}$ alkoxy$C_{1-6}$ alkyl is unsubstituted or substituted with one or more substituents independently selected from the group consisting of: halogen, and hydroxyl; $R^6$ may form a 4 to 7 membered ring with $R^7$ which may contain a nitrogen atom, an oxygen atom, a sulfur atom, or a double bond;
$R^{8a}$ and $R^{8b}$ are independently selected from the group consisting of:
(1) hydrogen, (2) halogen, (3) hydroxyl, (4) $C_{1-6}$ alkyl, and (5) —O—$C_{1-6}$ alkyl;
$R^9$ is selected from the group consisting of: (1) hydrogen and (2) $C_{1-6}$ alkyl; or a prodrug thereof or a pharmaceutically acceptable salt thereof,

[2] the compound described in [1] wherein:
A is phenyl, pyridyl, pyrazyl, pyrimidyl, quinolyl, isoquinolyl, quinoxalyl, or naphthyl;
X is selected from the group consisting of: —$CR^{8a}R^{8b}$—, —O—, —O—$CR^{8a}R^{8b}$—, —$NR^9$—, —$NR^9$—$CR^{8a}R^{8b}$—, and —S—;
$R^{5a}$ and $R^{5c}$ are independently selected from the group consisting of:
(1) hydrogen, (2) halogen, (3) hydroxyl, and (4) $C_{1-6}$ alkyl, wherein the $C_{1-6}$ alkyl is unsubstituted or substituted with one or more substituents independently selected from the group consisting of: halogen and hydroxyl;
$R^{5b}$ is hydrogen;
$R^{5d}$ is selected from the group consisting of: (1) hydrogen, (2) halogen, and (3) $C_{1-6}$ alkyl;
$R^{5c}$ may form a $C_{3-6}$ cycloalkyl with $R^{5d}$;
or a prodrug thereof or a pharmaceutically acceptable salt thereof,

[3] a compound of the following formula (II):

[Chem.2]

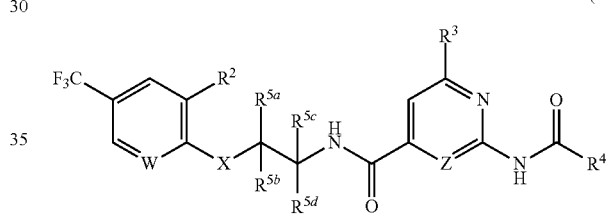

(II)

Wherein:
W is CH, $CR^1$, $CR^2$ or N;
$R^1$ is selected from the group consisting of: —$CF_3$, —$CHF_2$, —$OCF_3$, —$SF_5$, —$OCH_2CF_3$, and fluorobenzyloxy;
$R^2$ is selected from the group consisting of: (1) hydrogen, (2) halogen, (3) hydroxyl, (4) $C_{1-6}$ alkyl, (5) —O—$C_{1-6}$ alkyl, and (8) —CN;
X is selected from the group consisting of: —$CR^{8a}R^{8b}$—, —O—, —O—$CR^{8a}R^{8b}$—, —$NR^9$—, —$NR^9$—$CR^{8a}R^{8b}$—, and —S—;
Z is CH, $CR^3$ or N;
$R^3$ is selected from the group consisting of:
(1) hydrogen, (2) halogen, (3) hydroxyl, (4) $C_{1-6}$ alkyl, and (5) —O—$C_{1-6}$ alkyl;

$R^4$ is selected from the group consisting of: (1) $C_{1-6}$ alkyl, and (2) $C_{3-7}$ cycloalkyl, wherein the $C_{1-6}$ alkyl or the $C_{3-7}$ cycloalkyl is unsubstituted or substituted with one or more substituents independently selected form the group consisting of: halogen, hydroxyl, —$C_{1-6}$ alkyl, —O—$C_{1-6}$ alkyl, and $C_{3-7}$ cycloalkyl;
$R^{5a}$ and $R^{5c}$ independently selected from the group consisting of: (1) hydrogen, (2) halogen, (3) hydroxyl, and (4) $C_{1-6}$ alkyl which is unsubstituted or substituted with one or more substituents independently selected from the group consisting of: halogen and hydroxyl;
$R^{5b}$ is hydrogen;
$R^{5d}$ is selected from the group consisting of: (1) hydrogen, (2) halogen, and (3) $C_{1-6}$ alkyl;
$R^{5c}$ may form a $C_{3-6}$ cycloalkyl with $R^{5d}$;
$R^{8a}$ and $R^8b$ are independently selected from the group consisting of:
(1) hydrogen, (2) halogen, (3) hydroxyl, (4) $C_{1-6}$ alkyl, and (5) —O—$C_{1-6}$ alkyl;
$R^9$ is selected from the group consisting of: (1) hydrogen, and (2) $C_{1-6}$ alkyl;
or a prodrug thereof or a pharmaceutically acceptable salt thereof,

[4] a compound of the following formula (III):

[Chem.3]

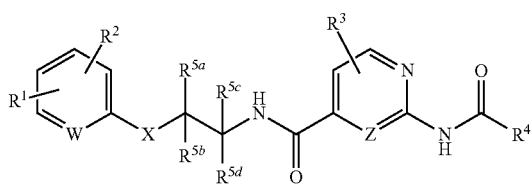

(III)

Wherein:
W is CH, or N;
R' is selected from the group consisting of: (1) hydrogen, (2) halogen, (3) hydroxyl, (4) $C_{1-6}$ alkyl, (5) —O—$C_{1-6}$ alkyl, and (6) —CN;
X is selected from the group consisting of: —$CR^{8a}R^{8b}$—, —O—, —O—$CR^{8a}R^{8b}$—, —$NR^9$—, —$NR^9$—$CR^{8a}R^{8b}$—, and —S—;
Z is CH or N;
$R^3$ is selected from the group consisting of:
(1) hydrogen, (2) halogen, (3) hydroxyl, (4) $C_{1-6}$ alkyl, and (5) —O—$C_{1-6}$ alkyl;
$R^4$ is selected from the group consisting of: (1) $C_{1-6}$ alkyl, and (2) $C_{3-7}$ cycloalkyl, wherein the $C_{1-6}$ alkyl or the $C_{3-7}$ cycloalkyl is unsubstituted or substituted with one or more substituents independently selected form the group consisting of: halogen and hydroxyl;
$R^{5a}$ and $R^{5c}$ are independently selected from the group consisting of: (1) hydrogen, (2) halogen, (3) hydroxyl, and (4) $C_{1-6}$ alkyl which is unsubstituted or substituted with one or more substituents independently selected from the group consisting of: halogen and hydroxyl;
$R^{5b}$ and $R^{5d}$ are hydrogen;
$R^{8a}$ and $R^{8b}$ are hydrogen;
$R^9$ is hydrogen;
or a prodrug thereof or a pharmaceutically acceptable salt thereof,

[5] the compound described in [4] wherein:
W is N;
or a prodrug thereof or a pharmaceutically acceptable salt thereof,

[6] a compound which is selected from the group consisting of:
2-(cyclopropanecarboxamido)-N-(2-(4-(trifluoromethyl)phenoxy)propyl)isonicotinamide;
2-acetamido-N-(2-((3-chloro-5-(trifluoromethyl)pyridin-2-yl)amino)ethyl)isonicotinamide;
N-(2-((3-chloro-5-(trifluoromethyl)pyridin-2-yl)amino)ethyl)-2-propionamidoisonicotinamide;
2-acetamido-N-(2-((3-chloro-5-(trifluoromethyl)pyridin-2-yl)amino)ethyl)-6-methylisonicotinamide;
N-(2-((3-chloro-5-(trifluoromethyl)pyridin-2-yl)amino)ethyl)-2-methyl-6-propionamidoisonicotinamide;
N-(2-((3-chloro-5-(trifluoromethyl)pyridin-2-yl)amino)ethyl)-2-(cyclopropanecarboxamido)isonicotinamide;
N-(2-((3-chloro-5-(trifluoromethyl)pyridin-2-yl)amino)ethyl)-2-isobutyramidoisonicotinamide;
2-acetamido-N-(2-((3-chloro-5-(trifluoromethyl)pyridin-2-yl)oxy)ethyl)isonicotinamide;
N-(2-((3-chloro-5-(trifluoromethyl)pyridin-2-yl)oxy)ethyl)-2-propionamidoisonicotinamide;
2-acetamido-N-(2-((3-chloro-5-(trifluoromethyl)pyridin-2-yl)oxy)ethyl)-6-methylisonicotinamide;
2-acetamido-N-(2-((3-chloro-5-(trifluoromethyl)pyridin-2-yl)oxy)ethyl)-6-methylpyrimidine-4-carboxamide;
2-methyl-6-propionamido-N-(2-((5-(trifluoromethyl)pyridin-2-yl)oxy)ethyl)isonicotinamide;
N-(2-((3-chloro-5-(trifluoromethyl)pyridin-2-yl)oxy)ethyl)-2-isobutyramidoisonicotinamide;
N-(2-((3-chloro-5-(trifluoromethyl)pyridin-2-yl)oxy)ethyl)-2-(cyclopropanecarboxamido)isonicotinamide;
N-(2-((3-chloro-5-(trifluoromethyl)pyridin-2-yl)oxy)ethyl)-2-methyl-6-propionamidoisonicotinamide;
N-(2-((3-chloro-5-(trifluoromethyl)pyridin-2-yl)oxy)ethyl)-2-(cyclopropanecarboxamido)-6-methylpyrimidine-4-carboxamide;
(R)—N-(2-((3-chloro-5-(trifluoromethyl)pyridin-2-yl)oxy)propyl)-2-isobutyramidoisonicotinamide;
2-isobutyramido-N-(2-(3-(trifluoromethoxy)phenoxy)ethyl)isonicotinamide;
2-acetamido-6-methyl-N-(2-(3-(trifluoromethoxy)phenoxy)ethyl)isonicotinamide;
2-acetamido-N-(2-(2-chloro-4-(trifluoromethyl)phenoxy)ethyl)isonicotinamide;
N-(2-(2-chloro-4-(trifluoromethyl)phenoxy)ethyl)-2-propionamidoisonicotinamide;
N-(2-(2-chloro-4-(trifluoromethyl)phenoxy)ethyl)-2-isobutyramidoisonicotinamide;
2-acetamido-N-(2-(2-chloro-4-(trifluoromethyl)phenoxy)ethyl)-6-methylisonicotinamide;
2-acetamido-6-methyl-N-(2-(4-(trifluoromethyl)phenoxy)ethyl)isonicotinamide;
N-(2-((3-chloro-5-(trifluoromethyl)pyridin-2-yl)oxy)ethyl)-2-(cyclopropanecarboxamido)-6-methylisonicotinamide;
N-(2-((3-chloro-5-(trifluoromethyl)pyridin-2-yl)amino)ethyl)-2-(cyclopropanecarboxamido)-6-methylisonicotinamide;
N-(3-(3-chloro-5-(trifluoromethyl)pyridin-2-yl)propyl)-2-(cyclopropanecarboxamido)isonicotinamide;
2-acetamido-N-(3-(3-chloro-5-(trifluoromethyl)pyridin-2-yl)propyl)-6-methylisonicotinamide;
N-(2-((3-fluoro-5-(trifluoromethyl)pyridin-2-yl)oxy)ethyl)-2-isobutyramido-6-methylisonicotinamide;
N-(3-(3-chloro-5-(trifluoromethyl)pyridin-2-yl)propyl)-2-propionamidoisonicotinamide;
2-acetamido-6-methyl-N-(2-(4-(pentafluorosulfanyl)phenoxy)ethyl)isonicotinamide;
2-propionamido-N-(2-(4-(pentafluorosulfanyl)phenoxy)ethyl)isonicotinamide;
2-(cyclopropanecarboxamido)-N-(2-(4-(pentafluorosulfanyl)phenoxy)ethyl)isonicotinamide;
2-isobutyramido-N-(2-(4-(pentafluorosulfanyl)phenoxy)ethyl)isonicotinamide;
N-(2-((3-chloro-5-(trifluoromethyl)pyridin-2-yl)oxy)ethyl)-2-isobutyramido-6-methylisonicotinamide;
N-(2-((3-chloro-5-(trifluoromethyl)pyridin-2-yl)oxy)ethyl)-2-(cyclopropanecarboxamido)pyrimidine-4-carboxamide;
N-(2-((3-chloro-5-(trifluoromethyl)pyridin-2-yl)amino)ethyl)-2-isobutyramido-6-methylisonicotinamide;
N-(2-((3-chloro-5-(trifluoromethyl)pyridin-2-yl)amino)ethyl)-2-(cyclopropanecarboxamido)pyrimidine-4-carboxamide;
N-(2-(2-chloro-4-(trifluoromethyl)phenoxy)ethyl)-2-methyl-6-propionamidoisonicotinamide;
N-(2-(2-chloro-4-(trifluoromethyl)phenoxy)ethyl)-2-(cyclopropanecarboxamido)isonicotinamide;
N-(2-(2-chloro-4-(trifluoromethyl)phenoxy)ethyl)-2-(cyclopropanecarboxamido)-6-methylisonicotinamide;
N-(2-(2-chloro-4-(trifluoromethyl)phenoxy)ethyl)-2-isobutyramido-6-methylisonicotinamide;
N-(2-(2-chloro-4-(trifluoromethyl)phenoxy)ethyl)-2-(cyclopropanecarboxamido)pyrimidine-4-carboxamide;
2-methyl-6-propionamido-N-(2-((6-(trifluoromethyl)quinolin-2-yl)oxy)ethyl)isonicotinamide;
2-(cyclopropanecarboxamido)-N-(2-((6-(trifluoromethyl)quinolin-2-yl)oxy)ethyl)isonicotinamide;
2-isobutyramido-N-(2-((6-(trifluoromethyl)quinolinyl)oxy)ethyl)isonicotinamide;
2-isobutyramido-N-(2-((6-(trifluoromethyl)quinolin-2-yl)amino)ethyl)isonicotinamide;
2-methyl-6-propionamido-N-(2-((6-(trifluoromethyl)isoquinolin-1-yl)oxy)ethyl)isonicotinamide;
2-methyl-6-propionamido-N-(2-((6-(2,2,2-trifluoroethoxy)naphthalen-2-yl)oxy)ethyl)isonicotinamide;
2-(cyclopropanecarboxamido)-N-(2-((6-(2,2,2-trifluoroethoxy)naphthalen-2-yl)oxy)ethyl)isonicotinamide;
2-isobutyramido-N-(2-((6-(2,2,2-trifluoroethoxy)naphthalen-2-yl)oxy)ethyl)isonicotinamide;
2-acetamido-N-(2-((3-chloro-5-(trifluoromethyl)pyridin-2-yl)thio)ethyl)isonicotinamide;
N-(2-((3-chloro-5-(trifluoromethyl)pyridin-2-yl)thio)ethyl)-2-isobutyramidoisonicotinamide;
2-acetamido-N-(2-((3-chloro-5-(trifluoromethyl)pyridin-2-yl)thio)ethyl)-6-methylisonicotinamide;
N-(2-((3-chloro-5-(trifluoromethyl)pyridin-2-yl)thio)ethyl)-2-methyl-6-propionamidoisonicotinamide;
2-acetamido-N-(2-((6-(trifluoromethyl)quinolin-2-yl)oxy)ethyl)isonicotinamide;
2-propionamido-N-(2-((6-(trifluoromethyl)quinolin-2-yl)oxy)ethyl)isonicotinamide;
2-acetamido-6-methyl-N-(2-((6-(trifluoromethyl)quinolin-2-yl)oxy)ethyl)isonicotinamide;
2-(cyclopropanecarboxamido)-6-methyl-N-(2-((6-(trifluoromethyl)quinolin-2-yl)oxy)ethyl)isonicotinamide;
2-isobutyramido-6-methyl-N-(2-((6-(trifluoromethyl)quinolin-2-yl)oxy)ethyl)isonicotinamide;
2-(cyclopropanecarboxamido)-N-(2-((6-(trifluoromethyl)quinolin-2-yl)oxy)ethyl)pyrimidine-4-carboxamide;
2-(2-hydroxy-2-methylpropanamido)-6-methyl-N-(2-((6-(trifluoromethyl)quinolin-2-yl)oxy)ethyl)isonicotinamide;

(R)-2-acetamido-N-(1-((3-chloro-5-(trifluoromethyl)pyridin-2-yl)oxy)propan-2-yl)ison icotinamide;
(R)—N-(1-((3-chloro-5-(trifluoromethyl)pyridin-2-yl)oxy)propan-2-yl)-2-propionamidoi sonicotinamide;
(R)-2-acetamido-N-(1-((3-chloro-5-(trifluoromethyl)pyridin-2-yl)oxy)propan-2-yl)-6-methylisonicotinamide;
(R)—N-(1-((3-chloro-5-(trifluoromethyl)pyridin-2-yl)oxy)propan-2-yl)-2-methyl-6-prop ionamidoisonicotinamide;
(R)—N-(1-((3-chloro-5-(trifluoromethyl)pyridin-2-yl)oxy)propan-2-yl)-2-(cyclopropane carboxamido)isonicotinamide;
(R)—N-(1-((3-chloro-5-(trifluoromethyl)pyridin-2-yl)oxy)propan-2-yl)-2-isobutyramido isonicotinamide;
(R)—N-(1-((3-chloro-5-(trifluoromethyl)pyridin-2-yl)oxy)propan-2-yl)-2-(cyclopropane carboxamido)-6-methylisonicotinamide;
(R)—N-(1-((3-chloro-5-(trifluoromethyl)pyridin-2-yl)oxy)propan-2-yl)-2-isobutyramido -6-methylisonicotinamide;
(R)—N-(1-((3-chloro-5-(trifluoromethyl)pyridin-2-yl)oxy)propan-2-yl)-2-(cyclopropane carboxamido)pyrimidine-4-carboxamide;
(S)—N-(2-((3-chloro-5-(trifluoromethyl)pyridin-2-yl)oxy)propyl)-2-methyl-6-propiona midoisonicotinamide;
(R)-2-acetamido-N-(2-((3-chloro-5-(trifluoromethyl)pyridin-2-yl)oxy)propyl)-6-methy lisonicotinamide;
(R)—N-(2-((3-chloro-5-(trifluoromethyl)pyridin-2-yl)oxy)propyl)-2-methyl-6-propiona midoisonicotinamide;
(R)—N-(2-((3-chloro-5-(trifluoromethyl)pyridin-2-yl)oxy)propyl)-2-(cyclopropanecarbo xamido)isonicotinamide;
(R)—N-(2-((3-chloro-5-(trifluoromethyl)pyridin-2-yl)oxy)propyl)-2-(cyclopropanecarbo xamido)-6-methylisonicotinamide;
(R)—N-(2-((3-chloro-5-(trifluoromethyl)pyridin-2-yl)oxy)propyl)-2-isobutyramido-6-m ethylisonicotinamide;
2-methyl-6-propionamido-N-(2-((7-(trifluoromethyl)quinolin-4-yl)oxy)ethyl)isonicotin amide;
2-(cyclopropanecarboxamido)-N-(2-((7-(trifluoromethyl)quinolin-4-yl)oxy)ethyl)isoni cotinamide;
2-isobutyramido-N-(2-((7-(trifluoromethyl)quinolin-4-yl)oxy)ethyl)isonicotinamide;
N-(2-((3-fluoro-5-(trifluoromethyl)pyridin-2-yl)oxy)ethyl)-2-methyl-6-propionamidois onicotinamide;
N-(2-((5-chloro-3-(trifluoromethyl)pyridin-2-yl)oxy)ethyl)-2-methyl-6-propionamidois onicotinamide;
2-propionamido-N-(2-((4-(trifluoromethyl)quinolin-2-yl)oxy)ethyl)isonicotinamide;
2-methyl-6-propionamido-N-(2-((4-(trifluoromethyl)quinolin-2-yl)oxy)ethyl)isonicotin amide;
2-isobutyramido-N-(2-((4-(trifluoromethyl)quinolin-2-yl)oxy)ethyl)isonicotinamide;
2-(cyclopropanecarboxamido)-N-(2-((4-(trifluoromethyl)quinolin-2-yl)oxy)ethyl)pyri midine-4-carboxamide;
2-butyramido-N-(2-((3-chloro-5-(trifluoromethyl)pyridin-2-yl)oxy)ethyl)isonicotinami de;
N-(2-((3-chloro-5-(trifluoromethyl)pyridin-2-yl)oxy)ethyl)-2-pivalamidoisonicotinami de;
N-(2-((3-chloro-5-(trifluoromethyl)pyridin-2-yl)oxy)ethyl)-6-methyl-2-propionamidop yrimidine-4-carboxamide;
N-(2((3-chloro-5-(trifluoromethyl)pyridin-2-yl)oxy)ethyl)-2-isobutyramido-6-methylp yrimidine-4-carboxamide;
2-acetamido-N-(2-(2-fluoro-4-(trifluoromethyl)phenoxy)ethyl)isonicotinamide;
N-(2-(2-fluoro-4-(trifluoromethyl)phenoxy)ethyl)-2-propionamidoisonicotinamide;
2-acetamido-N-(2-(2-fluoro-4-(trifluoromethyl)phenoxy)ethyl)-6-methylisonicotinami de;
N-(2-(2-fluoro-4-(trifluoromethyl)phenoxy)ethyl)-2-methyl-6-propionamidoisonicotina mide;
2-(cyclopropanecarboxamido)-N-(2-(2-fluoro-4-(trifluoromethyl)phenoxy)ethyl)isonic otinamide;
N-(2-(2-fluoro-4-(trifluoromethyl)phenoxy)ethyl)-2-isobutyramidoisonicotinamide;
2-(cyclopropanecarboxamido)-N-(2-(2-fluoro-4-(trifluoromethyl)phenoxy)ethyl)-6-met hylisonicotinamide;
N-(2-(2-fluoro-4-(trifluoromethyl)phenoxy)ethyl)-2-isobutyramido-6-methylisonicotin amide;
2-(cyclopropanecarboxamido)-N-(2-(2-fluoro-4-(trifluoromethyl)phenoxy)ethyl)pyrimi dine-4-carboxamide;
N-(2-(4-chloro-3-(trifluoromethyl)phenoxy)ethyl)-2-methyl-6-propionamidoisonicotin amide;
N-(2-(4-chloro-3-(trifluoromethyl)phenoxy)ethyl)-2-isobutyramidoisonicotinamide;
N-(2-(4-chloro-3-(trifluoromethyl)phenoxy)ethyl)-2-isobutyramido-6-methylisonicotin amide;
N-(2-(2-chloro-5-(trifluoromethyl)phenoxy)ethyl)-2-methyl-6-propionamidoisonicotin amide;
N-(2-(2-chloro-5-(trifluoromethyl)phenoxy)ethyl)-2-isobutyramido-6-methylisonicotin amide;
N-(2-(2-chloro-4-(trifluoromethoxy)phenoxy)ethyl)-2-methyl-6-propionamidoisonicoti namide;
N-(2-(2-chloro-4-(trifluoromethoxy)phenoxy)ethyl)-2-(cyclopropanecarboxamido)ison icotinamide;
N-(2-(2-chloro-4-(trifluoromethoxy)phenoxy)ethyl)-2-isobutyramidoisonicotinamide;
N-(2-(2-chloro-4-(trifluoromethoxy)phenoxy)ethyl)-2-isobutyramido-6-methylisonicot inamide;
N-(1-((3-chloro-5-(trifluoromethyl)pyridin-2-yl)oxy)-2-methylpropan-2-yl)-2-propiona midoisonicotinamide;
N-(1-((3-chloro-5-(trifluoromethyl)pyridin-2-yl)oxy)-2-methylpropan-2-yl)-2-(cyclopr opanecarboxamido)-6-methylpyrimidine-4-carboxamide;
N-(1-(((3-chloro-5-(trifluoromethyl)pyridin-2-yl)oxy)methyl)cyclopropyl)-2-isobutyra mido-6-methylisonicotinamide;
N-(2-((3-cyano-5-(trifluoromethyl)pyridin-2-yl)oxy)ethyl)-2-methyl-6-propionamidois onicotinamide;
2-acetamido-N-(2-(2-chloro-4-(trifluoromethoxy)phenoxy)ethyl)isonicotinamide;
N-(2-(2-chloro-4-(trifluoromethoxy)phenoxy)ethyl)-2-propionamidoisonicotinamide;
N-(2-(2-chloro-4-(trifluoromethoxy)phenoxy)ethyl)-2-(cyclopropanecarboxamido)-6-methylisonicotinamide;
2-acetamido-N-(2-(2-chloro-4-(trifluoromethoxy)phenoxy)ethyl)=6-methylisonicotina mide;
N-(2-(2-chloro-4-(trifluoromethoxy)phenoxy)ethyl)-2-(cyclopropanecarboxamido)pyri midine-4-carboxamide;
2-acetamido-N-(3-((3-chloro-5-(trifluoromethyl)pyridin-2-yl)amino)propyl)isonicotina mide;
N-(3-((3-chloro-5-(trifluoromethyl)pyridin-2-yl)amino)propyl)-2-propionamidoisonico tinamide;
N-(3-((3-chloro-5-(trifluoromethyl)pyridin-2-yl)amino)propyl)-2-isobutyramidoisonico tinamide;
2-acetamido-N-(3-((3-chloro-5-(trifluoromethyl)pyridin-2-yl)amino)propyl)-6-methyli sonicotinamide;
2-acetamido-N-(3-((3-chloro-5-(trifluoromethyl)pyridin-2-yl)oxy)propyl)isonicotinami de;
N-(3-((3-chloro-5-(trifluoromethyl)pyridin-2-yl)ox y)propyl)-2-isobutyramidoisonicoti namide;
2-acetamido-N-(3-((3-chloro-5-(trifluoromethyl)pyridin-2-yl)oxy)propyl)-6-methyliso nicotinamide;
N-(3-((3-chloro-5-(trifluoromethyl)pyridin-2-yl)oxy)propyl)-2-(cyclopropanecarboxam ido)-6-methylpyrimidine-4-carboxamide;

2-acetamido-N-(2-(2-methoxy-4-(trifluoromethyl)phenoxy)ethyl)isonicotinamide;
N-(2-(2-methoxy-4-(trifluoromethyl)phenoxy)ethyl)-2-propionamidoisonicotinamide;
2-acetamido-N-(2-(2-methoxy-4-(trifluoromethyl)phenoxy)ethyl)-6-methylisonicotina mide;
N-(2-(2-methoxy-4-(trifluoromethyl)phenoxy)ethyl)-2-methyl-6-propionamidoisonicot inamide;
2-(cyclopropanecarboxamido)-N-(2-(2-methoxy-4-(trifluoromethyl)phenoxy)ethyl)iso nicotinamide;
2-isobutyramido-N-(2-(2-methoxy-4-(trifluoromethyl)phenoxy)ethyl)isonicotinamide;
2-(cyclopropanecarboxamido)-N-(2-(2-methoxy-4-(trifluoromethyl)phenoxy)ethyl)-6-methylisonicotinamide;
2-isobutyramido-N-(2-(2-methoxy-4-(trifluoromethyl)phenoxy)ethyl)-6-methylisonicot inamide;
2-(cyclopropanecarboxamido)-N-(2-(2-methoxy-4-(trifluoromethyl)phenoxy)ethyl)pyri midine-4-carboxamide;
N-(1-(((3-chloro-5-(trifluoromethyl)pyridin-2-yl)oxy)methyl)cyclopropyl)-2-isobutyra mido-6-methylpyrimidine-4-carboxamide;
N-(1-(((3-chloro-5-(trifluoromethyl)pyridin-2-yl)oxy)methyl)cyclopropyl)-2-(cyclopro panecarboxamido)-6-methylpyrimidine-4-carboxamide;
2-butyramido-N-(1-(((3-chloro-5-(trifluoromethyl)pyridin-2-yl)oxy)methyl)cyclopropy l)isonicotinamide;
2-acetamido-N-(2-(2-methyl-4-(trifluoromethyl)phenoxy)ethyl)isonicotinamide;
N-(2-(2-methyl-4-(trifluoromethyl)phenoxy)ethyl)-2-propionamidoisonicotinamide;
2-acetamido-6-methyl-N-(2-(2-methyl-4-(trifluoromethyl)phenoxy)ethyl)isonicotinami de;
2-methyl-N-(2-(2-methyl-4-(trifluoromethyl)phenoxy)ethyl)-6-propionamidoisonicotin amide;
2-(cyclopropanecarboxamido)-N-(2-(2-methyl-4-(trifluoromethyl)phenoxy)ethyl)isoni cotinamide;
2-isobutyramido-N-(2-(2-methyl-4-(trifluoromethyl)phenoxy)ethyl)isonicotinamide;
2-(cyclopropanecarboxamido)-6-methyl-N-(2-(2-methyl-4-(trifluoromethyl)phenoxy)et hyl)isonicotinamide;
2-isobutyramido-6-methyl-N-(2-(2-methyl-4-(trifluoromethyl)phenoxy)ethyl)isonicoti namide;
2-(cyclopropanecarboxamido)-N-(2-(2-methyl-4-(trifluoromethyl)phenoxy)ethyl)pyri midine-4-carboxamide;
N-(2-(4-chloro-3-(trifluoromethyl)phenoxy)ethyl)-2-(cyclopropanecarboxamido)-6-me thylpyrimidine-4-carboxamide;
N-(2-(3-fluoro-4-(trifluoromethoxy)phenoxy)ethyl)-2-propionamidoisonicotinamide;
N-(2-(3-fluoro-4-(trifluoromethoxy)phenoxy)ethyl)-2-isobutyramidoisonicotinamide;
2-(cyclopropanecarboxamido)-N-(2-(3-fluoro-4-(trifluoromethoxy)phenoxy)ethyl)pyri midine-4-carboxamide;
2-(cyclopropanecarboxamido)-N-(2-(3-fluoro-4-(trifluoromethoxy)phenoxy)ethyl)isoni cotinamide;
2-acetamido-N-(2-(3-fluoro-4-(trifluoromethoxy)phenoxy)ethyl)-6-methylisonicotinam ide;
2-(cyclopropanecarboxamido)-N-(2-(3-fluoro-4-(trifluoromethoxy)phenoxy)ethyl)-6-m ethylpyrimidine-4-carboxamide;
2-acetamido-N-(2-(3-fluoro-4-(trifluoromethoxy)phenoxy)ethyl)isonicotinamide; and
N-(2-(3-fluoro-4-(trifluoromethoxy)phenoxy)ethyl)-2-isobutyramidoisonicotinamide;
or a prodrug thereof or a pharmaceutically acceptable salt thereof,

[7] the compound as described in [6] which is selected from the group consisting of:
2-(cyclopropanecarboxamido)-N-(2-(4-(trifluoromethyl)phenoxy)propyl)isonicotina mide;
2-acetamido-N-(2-((3-chloro-5-(trifluoromethyl)pyridin-2-yl)amino)ethyl)isonicotina mide;
N-(2-((3-chloro-5-(trifluoromethyl)pyridin-2-yl)amino)ethyl)-2-propionamidoisonico tinamide;
2-acetamido-N-(2-((3-chloro-5-(trifluoromethyl)pyridin-2-yl)amino)ethyl)-6-methyli sonicotinamide;
N-(2-((3-chloro-5-(trifluoromethyl)pyridin-2-yl)amino)ethyl)-2-methyl-6-propionami doisonicotinamide;
N-(2-((3-chloro-5-(trifluoromethyl)pyridin-2-yl)amino)ethyl)-2-(cyclopropanecarbox amido)isonicotinamide;
N-(2-((3-chloro-5-(trifluoromethyl)pyridin-2-yl)amino)ethyl)-2-isobutyramidoisonicoti namide;
2-acetamido-N-(2-((3-chloro-5-(trifluoromethyl)pyridin-2-yl)oxy)ethyl)isonicotinamid e;
N-(2-((3-chloro-5-(trifluoromethyl)pyridin-2-yl)oxy)ethyl)-2-propionamidoisonicotina mide;
2-acetamido-N-(2-((3-chloro-5-(trifluoromethyl)pyridin-2-yl)oxy)ethyl)-6-methylisoni cotinamide;
2-acetamido-N-(2-((3-chloro-5-(trifluoromethyl)pyridin-2-yl)oxy)ethyl)-6-methylpyri midine-4-carboxamide;
2-methyl-6-propionamido-N-(2-((5-(trifluoromethyl)pyridin-2-yl)oxy)ethyl)isonicotina mide;
N-(2-((3-chloro-5-(trifluoromethyl)pyridin-2-yl)oxy)ethyl)-2-isobutyramidoisonicotina mide;
N-(2-((a-chloro-5-(trifluoromethyl)pyridin-2-yl)oxy)ethyl)-2-(cyclopropanecarboxami do)isonicotinamide;
N-(2-((3-chloro-5-(trifluoromethyl)pyridin-2-yl)oxy)ethyl)-2-methyl-6-propionamidois onicotinamide;
N-(2-((3-chloro-5-(trifluoromethyl)pyridin-2-yl)oxy)ethyl)-2-(cyclopropanecarboxami do)-6-methylpyrimidine-4-carboxamide;
(R)—N-(2-((3-chloro-5-(trifluoromethyl)pyridin-2-yl)oxy)propyl)-2-isobutyramidoisoni cotinamide;
2-isobutyramido-N-(2-(3-(trifluoromethoxy)phenoxy)ethyl)isonicotinamide;
2-acetamido-6-methyl-N-(2-(3-(trifluoromethoxy)phenoxy)ethyl)isonicotinamide;
2-acetamido-N-(2-(2-chloro-4-(trifluoromethyl)phenoxy)ethyl)isonicotinamide;
N-(2-(2-chloro-4-(trifluoromethyl)phenoxy)ethyl)-2-propionamidoisonicotinamide;
N-(2-(2-chloro-4-(trifluoromethyl)phenoxy)ethyl)-2-isobutyramidoisonicotinamide;
2-acetamido-N-(2-(2-chloro-4-(trifluoromethyl)phenoxy)ethyl)-6-methylisonicotinami de;
2-acetamido-6-methyl-N-(2-(4-(trifluoromethyl)phenoxy)ethyl)isonicotinamide;
N-(2-((3-chloro-5-(trifluoromethyl)pyridin-2-yl)oxy)ethyl)-2-(cyclopropanecarboxami do)-6-methylisonicotinamide;
N-(2-((3-chloro-5-(trifluoromethyl)pyridin-2-yl)amino)ethyl)-2-(cyclopropanecarboxa mido)-6-methylisonicotinamide;
N-(3-(3-chloro-5-(trifluoromethyl)pyridin-2-yl)propyl)-2-(cyclopropanecarboxamido)i sonicotinamide;
2-acetamido-N-(3-(3-chloro-5-(trifluoromethyl)pyridin-2-yl)propyl)-6-methylisonicoti namide;
N-(2-((3-fluoro-5-(trifluoromethyl)pyridin-2-yl)oxy)ethyl)-2-isobutyramido-6-methylis onicotinamide;
N-(3-(3-chloro-5-(trifluoromethyl)pyridin-2-yl)propyl)-2-propionamidoisonicotinamid e;
2-acetamido-6-methyl-N-(2-(4-(pentafluorosulfanyl)phenoxy)ethyl)isonicotinamide;

2-propionamido-N-(2-(4-(pentafluorosulfanyl)phenoxy) ethyl)isonicotinamide;
2-(cyclopropanecarboxamido)-N-(2-(4-(pentafluorosulfanyl)phenoxy)ethyl)isonicotinamide;
2-isobutyramido-N-(2-(4-(pentafluorosulfanyl)phenoxy) ethyl)isonicotinamide;
N-(2-((3-chloro-5-(trifluoromethyl)pyridin-2-yl)oxy)ethyl)-2-isobutyramido-6-methylisonicotinamide;
N-(2-((3-chloro-5-(trifluoromethyl)pyridin2-yl)oxy)ethyl)-2-(cyclopropanecarboxamido)pyrimidine-4-carboxamide;
N-(2-((3-chloro-5-(trifluoromethyl)pyridin-2-yl)amino) ethyl)-2-isobutyramido-6-methylisonicotinamide;
N-(2-((3-chloro-5-(trifluoromethyl)pyridin-2-yl)amino) ethyl)-2-(cyclopropanecarboxamido)pyrimidine-4-carboxamide;
N-(2-(2-chloro-4-(trifluoromethyl)phenoxy)ethyl)-2-methyl-6-propionamidoisonicotinamide;
N-(2-(2-chloro-4-(trifluoromethyl)phenoxy)ethyl)-2-(cyclopropanecarboxamido)isonicotinamide;
N-(2-(2-chloro-4-(trifluoromethyl)phenoxy)ethyl)-2-(cyclopropanecarboxamido)-6-methylisonicotinamide;
N-(2-(2-chloro-4-(trifluoromethyl)phenoxy)ethyl)-2-isobutyramido-6-methylisonicotinamide;
N-(2-(2-chloro-4-(trifluoromethyl)phenoxy)ethyl)-2-(cyclopropanecarboxamido)pyrimidine-4-carboxamide;
2-acetamido-N-(2-((3-chloro-5-(trifluoromethyl)pyridin-2-yl)thio)ethyl)isonicotinamide;
N-(2-((3-chloro-5-(trifluoromethyl)pyridin-2-yl)thio)ethyl)-2-isobutyramidoisonicotinamide;
2-acetamido-N-(2-((3-chloro-5-(trifluoromethyl)pyridin-2-yl)thio)ethyl)-6-methylisonicotinamide;
N-(2-((3-chloro-5-(trifluoromethyl)pyridin-2-yl)thio)ethyl)-2-methyl-6-propionamidoisonicotinamide;
(R)-2-acetamido-N-(1-((3-chloro-5-(trifluoromethyl)pyridin-2-yl)oxy)propan-2-yl)isonicotinamide;
(R)—N-(1-((3-chloro-5-(trifluoromethyl)pyridin-2-yl)oxy) propan-2-yl)-2-propionamidoisonicotinamide;
(R)-2-acetamido-N-(1-((3-chloro-5-(trifluoromethyl)pyridin-2-yl)oxy)propan-2-yl)-6-methylisonicotinamide;
(R)—N-(1-((3-chloro-5-(trifluoromethyl)pyridin-2-yl)oxy) propan-2-yl)-2-methyl-6-propionamidoisonicotinamide;
(R)—N-(1-((3-chloro-5-(trifluoromethyl)pyridin-2-yl)oxy) propan-2-yl)-2-(cyclopropane carboxamido)isonicotinamide;
(R)—N-(1-((3-chloro-5-(trifluoromethyl)pyridin-2-yl)oxy) propan-2-yl)-2-isobutyramido isonicotinamide;
(R)—N-(1-((3-chloro-5-(trifluoromethyl)pyridin-2-yl)oxy) propan-2-yl)-2-(cyclopropane carboxamido)-6-methylisonicotinamide;
(R)—N-(1-((3-chloro-5-(trifluoromethyl)pyridin-2-yl)oxy) propan-2-yl)-2-isobutyramido-6-methylisonicotinamide;
(R)—N-(1-((3-chloro-5-(trifluoromethyl)pyridin-2-yl)oxy) propan-2-yl)-2-(cyclopropane carboxamido)pyrimidine-4-carboxamide;
(S)—N-(2-((3-chloro-5-(trifluoromethyl)pyridin-2-yl)oxy) propyl)-2-methyl-6-propionamidoisonicotinamide;
(R)-2-acetamido-N-(2-((3-chloro-5-(trifluoromethyl)pyridin-2-yl)oxy)propyl)-6-methylisonicotinamide;
(R)—N-(2-((3-chloro-5-(trifluoromethyl)pyridin-2-yl)oxy) propyl)-2-methyl-6-propionamidoisonicotinamide;
(R)—N-(2-((3-chloro-5-(trifluoromethyl)pyridin-2-yl)oxy) propyl)-2-(cyclopropanecarboxamido)isonicotinamide;
(R)—N-(2-((3-chloro-5-(trifluoromethyl)pyridin-2-yl)oxy) propyl)-2-(cyclopropanecarboxamido)-6-methylisonicotinamide;
(R)—N-(2-((3-chloro-5-(trifluoromethyl)pyridin-2-yl)oxy) propyl)-2-isobutyramido-6-methylisonicotinamide;
N-(2-((3-fluoro-5-(trifluoromethyl)pyridin-2-yl)oxy)ethyl)-2-methyl-6-propionamidoisonicotinamide;
N-(2-((5-chloro-3-(trifluoromethyl)pyridin-2-yl)oxy)ethyl)-2-methyl-6-propionamidoisonicotinamide;
2-butyramido-N-(2-((3-chloro-5-(trifluoromethyl)pyridin-2-yl)oxy)ethyl)isonicotinamide;
N-(2-((3-chloro-5-(trifluoromethyl)pyridin-2-yl)oxy)ethyl)-2-pivalamidoisonicotinamide;
N-(2-((3-chloro-5-(trifluoromethyl)pyridin-2-yl)oxy)ethyl)-6-methyl-2-propionamidopyrimidine-4-carboxamide;
N-(2-((3-chloro-5-(trifluoromethyl)pyridin-2-yl)oxy)ethyl)-2-isobutyramido-6-methylpyrimidine-4-carboxamide;
2-acetamido-N-(2-(2-fluoro-4-(trifluoromethyl)phenoxy) ethyl)isonicotinamide;
N-(2-(2-fluoro-4-(trifluoromethyl)phenoxy)ethyl)-2-propionamidoisonicotinamide;
2-acetamido-N-(2-(2-fluoro-4-(trifluoromethyl)phenoxy) ethyl)-6-methylisonicotinamide;
N-(2-(2-fluoro-4-(trifluoromethyl)phenoxy)ethyl)-2-methyl-6-propionamidoisonicotinamide;
2-(cyclopropanecarboxamido)-N-(2-(2-fluoro-4-(trifluoromethyl)phenoxy)ethyl)isonicotinamide;
N-(2-(2-fluoro-4-(trifluoromethyl)phenoxy)ethyl)-2-isobutyramidoisonicotinamide;
2-(cyclopropanecarboxamido)-N-(2-fluoro-4-(trifluoromethyl)phenoxy)ethyl)-6-methylisonicotinamide;
N-(2-(2-fluoro-4-(trifluoromethyl)phenoxy)ethyl)-2-isobutyramido-6-methylisonicotinamide;
2-(cyclopropanecarboxamido)-N-(2-(2-fluoro-4-(trifluoromethyl)phenoxy)ethyl)pyrimidine-4-carboxamide;
N-(2-(4-chloro-3-(trifluoromethyl)phenoxy)ethyl)-2-methyl-6-propionamidoisonicotinamide;
N-(2-(4-chloro-3-(trifluoromethyl)phenoxy)ethyl)-2-isobutyramidoisonicotinamide;
N-(2-(4-chloro-3-(trifluoromethyl)phenoxy)ethyl)-2-isobutyramido-6-methylisonicotinamide;
N-(2-(2-chloro-5-(trifluoromethyl)phenoxy)ethyl)-2-methyl-6-propionamidoisonicotinamide;
N-(2-(2-chloro-5-(trifluoromethyl)phenoxy)ethyl)-2-isobutyramido-6-methylisonicotinamide;
N-(2-(2-chloro-4-(trifluoromethoxy)phenoxy)ethyl)-2-methyl-6-propionamidoisonicotinamide;
N-(2-(2-chloro-4-(trifluoromethoxy)phenoxy)ethyl)-2-(cyclopropanecarboxamido)isonicotinamide;
N-(2-(2-chloro-4-(trifluoromethoxy)phenoxy)ethyl)-2-isobutyramidoisonicotinamide;
N-(2-(2-chloro-4-(trifluoromethoxy)phenoxy)ethyl)-2-isobutyramidomethylisonicotinamide;
N-(1-((3-chloro-5-(trifluoromethyl)pyridin-2-yl)oxy)-2-methylpropan-2-yl)-2-propionamidoisonicotinamide;
N-(1-((3-chloro-5-(trifluoromethyl)pyridin-2-yl)oxy)-2-methylpropan-2-yl)-2-(cyclopropanecarboxamido)-6-methylpyrimidine-4-carboxamide;
N-(1-(((3-chloro-5-(trifluoromethyl)pyridin-2-yl)oxy) methyl)cyclopropyl)-2-isobutyramido-6-methylisonicotinamide;
N-(2-((3-cyano-5-(trifluoromethyl)pyridin-2-yl)oxy)ethyl)-2-methyl-6-propionamidoisonicotinamide;
2-acetamido-N-(2-(2-chloro-4-(trifluoromethoxy)phenoxy) ethyl)isonicotinamide;
N-(2-(2-chloro-4-(trifluoromethoxy)phenoxy)ethyl)-2-propionamidoisonicotinamide;
N-(2-(2-chloro-4-(trifluoromethoxy)phenoxy)ethyl)-2-(cyclopropanecarboxamido)-6-methylisonicotinamide;

2-acetamido-N-(2-(2-chloro-4-(trifluoromethoxy)phenoxy)ethyl)-6-methylisonicotina mide;
N-(2-(2-chloro-4-(trifluoromethoxy)phenoxy)ethyl)-2-(cyclopropanecarboxamido)pyri midine-4-carboxamide;
2-acetamido-N-(3-((3-chloro-5-(trifluoromethyl)pyridin-2-yl)amino)propyl)isonicotina mide;
N-(3-((3-chloro-5-(trifluoromethyl)pyridin-2-yl)amino)propyl)-2-propionamidoisonico tinamide;
N-(3-((3-chloro-5-(trifluoromethyl)pyridin-2-yl)amino)propyl)-2-isobutyramidoisonico tinamide;
2-acetamido-N-(3-((3-chloro-5-(trifluoromethyl)pyridin-2-yl)amino)propyl)-6-methyli sonicotinamide;
2-acetamido-N-(3-((3-chloro-5-(trifluoromethyl)pyridin-2-yl)oxy)propyl)isonicotinami de;
N-(3-((3-chloro-5-(trifluoromethyl)pyridin-2-yl)oxy)propyl)-2-isobutyramidoisonicoti namide;
2-acetamido-N-(3-((3-chloro-5-(trifluoromethyl)pyridin-2-yl)oxy)propyl)-6-methyliso nicotinamide;
N-(343-chloro-5-(trifluoromethyl)pyridin-2-yl)oxy)propyl)-2-(cyclopropanecarboxam ido)-6-methylpyrimidine-4-carboxamide;
2-acetamido-N-(2-(2-methoxy-4-(trifluoromethyl)phenoxy)ethyl)isonicotinamide;
N-(2-(2-methoxy-4-(trifluoromethyl)phenoxy)ethyl)-2-propionamidoisonicotinamide;
2-acetamido-N-(2-(2-methoxy-4-(trifluoromethyl)phenoxy)ethyl)-6-methylisonicotina mide;
N-(2-(2-methoxy-4-(trifluoromethyl)phenoxy)ethyl)-2-methyl-6-propionamidoisonicot inamide;
2-(cyclopropanecarboxamido)-N-(2-(2-methoxy-4-(trifluoromethyl)phenoxy)ethyl)iso nicotinamide;
2-isobutyramido-N-(2-(2-methoxy-4-(trifluoromethyl)phenoxy)ethyl)isonicotinamide;
2-(cyclopropanecarboxamido)-N-(2-(2-methoxy-4-(trifluoromethyl)phenoxy)ethyl)-6-methylisonicotinamide;
2-isobutyramido-N-(2-(2-methoxy-4-(trifluoromethyl)phenoxy)ethyl)-6-methylisonicot inamide;
2-(cyclopropanecarboxamido)-N-(2-(2-methoxy-4-(trifluoromethyl)phenoxy)ethyl)pyri midine-4-carboxamide;
N-(1-(((3-chloro-5-(trifluoromethyl)pyridin-2-yl)oxy)methyl)cyclopropyl)-2-isobutyra mido-6-methylpyrimidine-4-carboxamide;
N-(1-(((3-chloro-5-(trifluoromethyl)pyridin-2-yl)oxy)methyl)cyclopropyl)-2-(cyclopro panecarboxamido)-6-methylpyrimidine-4-carboxamide;
2-butyramido-N-(1-(((3-chloro-5-(trifluoromethyl)pyridin-2-yl)oxy)methyl)cyclopropy l)isonicotinamide;
2-acetamido-N-(2-(2-methyl-4-(trifluoromethyl)phenoxy)ethyl)isonicotinamide;
N-(2-(2-methyl-4-(trifluoromethyl)phenoxy)ethyl)-2-propionamidoisonicotinamide;
2-acetamido-6-methyl-N-(2-(2-methyl-4-(trifluoromethyl)phenoxy)ethyl)isonicotinami de;
2-methyl-N-(2-(2-methyl-4-(trifluoromethyl)phenoxy)ethyl)-6-propionamidoisonicotin amide;
2-(cyclopropanecarboxamido)-N-(2-(2-methyl-4-(trifluoromethyl)phenoxy)ethyl)isoni cotinamide;
2-isobutyramido-N-(2-(2-methyl-4-(trifluoromethyl)phenoxy)ethyl)isonicotinamide;
2-(cyclopropanecarboxamido)-6-methyl-N-(2-(2-methyl-4-(trifluoromethyl)phenoxy)et hyl)isonicotinamide;
2-isobutyramido-6-methyl-N-(2-(2-methyl-4-(trifluoromethyl)phenoxy)ethyl)isonicoti namide;
2-(cyclopropanecarboxamido)-N-(2-(2-methyl-4-(trifluoromethyl)phenoxy)ethyl)pyri midine-4-carboxamide;
N-(2-(3-fluoro-4-(trifluoromethoxy)phenoxy)ethyl)-2-propionamidoisonicotinamide;
N-(2-(3-fluoro-4-(trifluoromethoxy)phenoxy)ethyl)-2-isobutyramidoisonicotinamide;
2-(cyclopropanecarboxamido)-N-(2-(3-fluoro-4-(trifluoromethoxy)phenoxy)ethyl)pyri midine-4-carboxamide;
2-(cyclopropanecarboxamido)-N-(2-(3-fluoro-4-(trifluoromethoxy)phenoxy)ethyl)isoni cotinamide;
2-acetamido-N-(2-(3-fluoro-4-(trifluoromethoxy)phenoxy)ethyl)-6-methylisonicotinam ide;
2-acetamido-N-(2-(3-fluoro-4-(trifluoromethoxy)phenoxy)ethyl)isonicotinamide; and
N-(2-(3-fluoro-4-(trifluoromethyl)phenoxy)ethyl)-2-isobutyramidoisonicotinamide; or a prodrug thereof or a pharmaceutically acceptable salt thereof,

[8] a pharmaceutical composition comprising a compound or a prodrug thereof or a pharmaceutically acceptable salt thereof, as described in any one of [1] to [7], and a pharmaceutically acceptable carrier,

[9] the pharmaceutical composition as described in [8], further comprising another pharmacologically active agent,

[10] a method for the treatment or a condition or disorder in which Nav1.7 and Nav1.8 channel blockers are involved, in an animal, including a human, which comprises administering to the animal in need of such treatment a therapeutically effective amount of a compound or a prodrug thereof or a pharmaceutically acceptable salt thereof, as described in any one of [1] to [7],

[11] the method as described in [10], wherein said condition or disorder is selected from the group consisting of: pain, acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back, pain, head or neck pain, severe or intractable pain, breakthrough pain, postsurgical pain, stroke, cancer pain, seizure disorder, causalgia, and chemo-induced pain; and combinations thereof,

[12] a use of a compound described in any one of [1] to [7] or a pharmaceutically acceptable salt, prodrug, solvate or composition thereof for the manufacture of a medicament for the treatment of a condition or disorder in which Nav1.7 and Nav1.8 channel blockers are involved,

[13] the use as described in [12], wherein said condition or disorder is selected from the group consisting of: pain, acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke, cancer pain, seizure disorder, causalgia, and chemo-induced pain; and combinations thereof,

[14] a compound described in any one of [1] to [7] or a prodrug thereof or a pharmaceutically acceptable salt thereof for use in the treatment of a condition or disorder in which Nav1.7 and Nav1.8 channel blockers are involved, and

[15] a process for preparing a pharmaceutical composition comprising mixing a compound or a prodrug thereof or a pharmaceutically acceptable salt thereof, as described in any one of [1] to [7], and a pharmaceutically acceptable carrier or excipient.

Advantageous Effects of Invention

The amide derivatives of the present invention are sodium channel blockers and have a number of therapeutic applications, particularly in the treatment of pain.

More particularly, the amide derivatives of the invention are selective Nav1.7 and Nav1.8 channel blockers. In the discussion that follows, the invention is exemplified by reference to the inhibition of Nav1.7 and Nav1.8 channel.

They show the affinity for Nav1.7 and Nav1.8 channel which is significantly greater than their affinity for Nav1.5 channel.

The amide derivatives of the invention show good selectivity for the Nav1.7 and Nav1.8 channels as compared with Nav1.5 channel.

In particular, the amide derivatives of the present invention are selective for the Nav1.7 and Nav1.8 channels over the Nav1.5 channel, leading to improvements in the side-effect profile.

The amide derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculo-skeletal system, spine, urogenital system, cardiovascular system and CNS, including cancer pain, back pain, orofacial pain and chemo-induced pain.

Other conditions that may be treated with the amide derivatives of the present invention include pruritus, multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke, cancer pain, seizure disorder and causalgia.

As illustrated in the above formulae (I), (II) and (III), the present invention is characterized by amide moiety in the right part. Bayer CropScience discloses structurally close arts in WO2014/076015, WO2015/144657 and EP2730570. The closest compounds are thought to be a compound of the example No. 1-63 and No. 1-3' in the WO2014/076015. The difference between the present invention and the structurally close art is well brought out as follows.

The Nav1.7 activities of the representative chemical structures in the present invention and the structurally close arts are summarized in the following Table 1. Compound (A) Example 13 and compound (B) Example 35 of the present invention have inhibitory activities against Nav1.7 channel with 0.37 microM and 0.19 microM, respectively. On the contrary, comparative compound.(C) No. 1-63 and comparative compound (D) No. 1-3 of the structurally close arts show the inhibitory activity against Nav1.7 channel with >3 microM. Both the Example 13 and 35 show good activity against Nav1.8 as well. In addition, the compounds of the structurally close arts relate to the use for endoparasiticides and nematicides and controlling harmful microorganisms in plants.

TABLE 1

| Present invention/Literature | Chemical structure | Nav1.7 activity (IC$_{50}$) |
|---|---|---|
| Present invention | compound (A) Example 13 | 0.37 microM |
| Present invention | compound (B) Example 35 | 0.19 microM |

TABLE 1-continued

| Present invention/Literature | Chemical structure | Nav1.7 activity (IC$_{50}$) |
|---|---|---|
| WO2014/076015 | comparative compound (C) No. 1-63 | >3 microM |
| WO2014/076015 | comparative compound (D) No. 1-3 | >3 microM |

In addition, compounds with the amide moiety in the right part are disclosed in the literatures such as WO2015/069593 and WO2012/053186. However, compounds with O-linkage in the middle part are never found in the said literatures.

Examples of conditions or disorders mediated by Nav1.7 and Nav1.8 channels include, but are not limited to, Nav1.7 and Nav1.8 channels related diseases. The compounds of the present invention show the Nav1.7 and Nav1.8 channels blocking activity. The compounds of the present invention may show less toxicity; favorable absorption, distribution, metabolism and excretion; favorable solubility; favorable protein binding affinity other than Nav1.7 and Nav1.8 channels; less drug-drug interaction; reduced inhibitory activity at HERG channel; and/or reduced QT prolongation.

DESCRIPTION OF EMBODIMENTS

As appreciated by those of skill in the art, "halogen" or "halo" as used herein is intended to include fluoro, chloro, bromo and iodo. Similarly, 1-6, as in $C_{1-6}$ is defined to identify the number as having 1, 2, 3, 4, 5 or 6. According to the definition, for example, $C_{1-6}$, as in $C_{1-6}$alkyl is defined to identify the alkyl group as having 1, 2, 3, 4, 5 or 6 carbons. Similarly, $C_{2-6}$ alkenyl is defined to identify the alkenyl group as having 2, 3, 4, 5 or 6 carbons. A group which is designated as being independently substituted with substituents may be independently substituted with multiple numbers of such substituents.

The term "alkyl", as used herein, means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

The term "alkoxy", as used herein, means an —O-alkyl such as, but not limited to, methoxy, ethoxy, propoxy, 2-propoxy, butoxy (including all isomeric forms), and the like.

The term "alkenyl", as used herein, means a hydrocarbon radical having at least one double bond, which may be in a E- or a Z- arrangement, including, but not limited to, ethenyl, propenyl, 1-butenyl, 2-butenyl and the like.

The term "cycloalkyl", as used herein, means a mono-, bi-, or tricyclic ring such as, but not limited to, cyclopropyl, cyclobutyl, cyclopentyl, cyclohexyl, cycloheptyl, norbornyl, adamantyl groups, and the like.

The term "aryl", as used herein, means unsaturated or partially saturated mono- or bicyclic 5-15 membered ring which consists of carbon atoms. Examples of such aryl include, but are not limited to, phenyl, naphthyl, indanyl, indenyl, 1,2,3,4-tetrahydronaphthyl, 1,2-dihydronaphthyl, 2,3-dihydro-1H-indenyl, cyclohexenyl, cyclopentenyl, (1S, 4S)-bicyclo[2.2.2]oct-2-enyl, and (1R,4S)-bicyclo[2.2.1]hept-2-enyl and the like.

The term "heteroaryl" as used herein, means unsaturated and partially saturated mono- or bicyclic 5-15 membered ring, preferably 5-10 membered ring, which may contain 1-4 heteroatoms selected from O, N and S.

Examples of such heteroaryl include, but are not limited to, thiophenyl, thiazolyl, isoxazolyl, pyrazolyl, pyrazyl, tetrazolyl, furanyl, pyrrolyl, imidazolyl, oxazolyl, isothiazolyl, triazolyl, thiadiazolyl, pyridyl, pyrimidyl, pyridazinyl, pyrazinyl, triazinyl, benzofuranyl, benzothiophenyl, benzotriazolyl, indolyl, indazolyl, benzoimidazolyl, pyrrolopyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinoxalyl, quinazolinyl, phthalazinyl, quinoxalinyl, naphthyridinyl, pyridopyrimidinyl, and N-oxides thereof and S-oxides thereof and the like.

The term "treating" or "treatment", as used herein, includes prohibiting, restraining, slowing, stopping, or reversing the progression or severity of an existing symptom or disorder. As used herein, the term "preventing" or "to prevent" includes prohibiting, restraining, or inhibiting the incidence or occurrence of a symptom or disorder.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formulae (I), (II) and (III).

Compounds of formulae (I), (II) and (III) can form acid addition salts thereof. It will be appreciated that for use in medicine the salts of the compounds of formulae (I), (II) and (III) should be pharmaceutically acceptable. Suitable pharmaceutically acceptable salts will be apparent to those skilled in the art and include those described in J. Pharm. Sci, 1977, 66, 1-19, such as acid addition salts formed with, inorganic acids e.g., but not limited to, hydrochloric, hydrobromic, sulfuric, nitric or phosphoric acid; and organic acids e.g., but not limited to, succinic, maleic, formic, acetic, trifluoroacetic, propionic, fumaric, citric, tartaric, benzoic, p-toluenesulfonic, methanesulfonic or naphthalenesulfonic acid. Certain of the compounds of formulae (I), (II) and (III) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases such as choline, arginine, benzamine, diethylamine, glycine, lysine, meglumine, olamine, 2-amino-2-methylpropan-1-ol, benethamine, tert-butylamine, epolamine, ethylenediamine, hydrabamine, morpholine, piperazine, procaine, triethanolamine, diethanolamine, monoethanolamine, triisopropanolamine, and tromethamine.

Also within the scope of the invention are so-called "prodrugs" of the compounds of formulae (I), (II) and (III). Thus certain derivatives of compounds of formulae (I), (II) and (III) which may have little or no pharmacological activity themselves can, when administered into or onto the body, be converted into compounds of formulae (I), (II) and (III) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

Prodrugs in accordance with the invention can, for example, be produced by replacing appropriate' functionalities present in the compounds of formulae (I), (II) and (III) with certain moieties known to those skilled in the art as 'pro-moieties' as described, for example, in Design of Prodrugs by H Bundgaard (Elsevier; 1985). Some examples of prodrugs in accordance with the invention include:

(i) where the compound of formulae (I), (II) and (III) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred the moieties are replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the formulae (I), (II) and (III) contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Compounds of formulae (I), (II) and (III) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formulae (I), (II) and (III) and their pharmaceutically acceptable salts.

Compounds of formulae (I), (II) and (III) may have polymorphs in crystalline form, which are within the scope of the present invention.

Additionally, compounds of formulae (I), (II) and (III) may be administered as prodrugs. As used herein, a "prodrug" of a compound of formulae (I), (II) and (III) is a functional derivative of the compound which, upon administration to a patient, eventually liberates the compound of formulae (I), (II) and (III) in vivo. Administration of a compound of formulae (I), (II) and (III) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formulae (I), (II) and (III), there may be one or more chiral carbon atoms. In such cases, compounds of formulae (I), (II) and (III) exist as stereoisomers. The invention extends to all optical isomers such as stereoisomeric forms of the compounds of formulae (I), (II) and (III) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2$H, $^3$H, $^{11}$C, $^{13}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{123}$I isotopes are particularly useful in SPECT (single photon emission computerized tomography), all useful in brain imaging. Further, substitution with heavier isotopes such as deuterium, i.e., $^3$H, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, certain compounds exhibit unexpected properties, such as with respect to duration of action and/or metabolism, such as increased metabolic stability, enhanced oral bioavailability or absorption, and/or decreased drug-drug interactions.

The compounds of formulae (I), (II) and (III), being Nav1.7 and Nav1.8 channel blockers, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Rouge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back, pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
(i) pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
(ii) heart and vascular pain, including pain caused by angina, myocardial infarction, mitral stenosis, pericarditis, Raynaud's phenomenon, scleredema and skeletal muscle ischemia;
(iii) head pain, such as migraine (including migraine with aura and migraine without aura), cluster headache, tension-type headache mixed headache and headache associated with vascular disorders; and
(vi) orofacial pain, including dental pain, otic pain, burning mouth syndrome and temporomandibular myofascial pain.

Compounds of formulae (I), (II) and (III) are also expected to be useful in the treatment of multiple sclerosis.

The invention also relates to therapeutic use of compounds of formulae (I), (II) and (III) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, and hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

Nav1.7 and Nav1.8 channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with Nav1.7 and Nav1.8 channels, including one or more of the following conditions or diseases: pain, acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, post-surgical pain, stroke, cancer pain, seizure disorder, causalgia, and chemo-induced pain.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A Nav1.7 and Nav1.8 channels blocker may be usefully combined with another pharmacologically active compound, or with two or more other pharmacologically active compounds, particularly in the treatment of inflammatory, pain and urological diseases or disorders. For example, a Nav1.7 and Nav1.8 channels blocker, particularly a compound of formulae (I), (II) and (III), or a prodrug thereof or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal anti-inflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine; —a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphenadrine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2 (1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-me thylphenyl)-7H-[1,4]diazocino[2,1-g][1,7]-naphthyridine-6,13-dione (TAK-637), 5-[[(2R,3S)-2-[(1R)-1-[3,5-bis(trifluoromethyl)phenyl]ethoxy-3-(4-fluorophenyl)-4-m orpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine or ipratropium;

a COX-2 selective inhibitor, e.g. celecoxib, rofecoxib, parecoxib, valdecoxib, deracoxib, etoricoxib, or lumiracoxib;

a coal-tar analgesic, e.g. paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resiniferatoxin) or antagonist (e.g. capsazepine);

a transient receptor potential cation channel subtype (V1, V2, V3, V4, M8, M2, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (registered trademark);

a PDEV inhibitor, such as 5-[2-ethoxy-5-(4-methyl-1-piperazinylsulphonyl)phenyl]-1-methyl-3-n-propyl-1, 6-dih ydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino [2',1':6,1] pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imida zo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyr azolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethy l]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, or 3-(1-methyl-7-oxo-3-propyl-6,7-dihydro-1H-pyrazolo[4,3-d] pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, mirogabalin, (3-(aminomethyl)bicyclic[3.2.0]hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy) proline, (2S,4S)-4-(3-fluorobenzyl)proline, [(1R,5R, 6S)-6-(aminomethyl)bicyclo[3.2.0]hept-6-yl]acetic acid, 3-((1-(aminomethyl)cyclohexyl)methyl)-4H-[1,2,4]oxadiazol-5-one, C-[1-((1H-tetrazol-5-yl)methyl)cycloheptyl]methylamine, (3S,4S)-(1-(aminomethyl)-3,4-dimethylcyclopentyl)acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, or (3R,4R,5R)-3-amino-4,5-dimethyloctanoic acid;

a cannabinoid;

a metabotropic glutamate receptors (mGluRs) antagonist such as mGluR1, mGluR2, mGluR3, mGluR5, or mGluR7;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine or trazodone;

a noradrenaline (norepinephrine) reuptake inhibitor, such as maprotiline, lofepramine, mirtazapine, oxaprotiline, fezolamine, tomoxetine, mianserin, bupropion, bupropion metabolite hydroxybupropion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran or imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarboni trile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridi necarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-car bonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl]phenoxy-methyl]-1-meth yl-2-quinolone (ZD-2138), or 2,3,5-trimethyl-6-(3-pyridylmethyl),1,4-benzoquinone (CV-6504);

a sodium channel blocker, such as lidocaine;

a calcium channel blocker, such as ziconotide, zonisamide, mibefradil;

a 5-HT3 antagonist, such as ondansetron;

a chemotherapy drug such as oxaliplatin, 5-fluorouracil, leucovorin, paclitaxel;

a Janus kinase (JAK) inhibitor such as tofacitinib;

a calcitonin gene related peptide (CGRP) antagonist;

a bradykinin (BK1 and BK2) antagonist;

a voltage gated sodium dependent channel blocker (Nav1.3, Nav1.7, Nav1.8, Nav1.9);

a voltage dependent calcium channel blocker (N-type, T-type);

a P2X (ion channel type ATP receptor) antagonist;

an acid-sensing ion channel (ASIC1,a, ASIC3) antagonist;

an Angiotensin AT2 antagonist;

a Chemokine CCR2B receptor antagonist;

a Cathepsin (B, S, K) inhibitor;

a sigma 1 receptor agonist or antagonist;

a nerve growth factor (NGF) binder or inhibitor such as tanezumab;

a tropomyosin receptor kinase A (TrkA) inhibitor;

a fatty acid amide hydrolase (FAAH) inhibitor;

a monoacylglycerol lipase (MAGL) inhibitor;

a microsomal prostaglandin E synthase type-1 (mPGES-1) inhibitor;

a $GABA_A$ modulator;

a GlyR3 agonist or positive modulator;

an AMPA receptor antagonist such as perampanel;

a potassium channel KCNQ/Kv7 opener or positive modulator such as retigabine or flupirtine;

a G protein-coupled inwardly-rectifying potassium channel (GIRK) opener or positive modulator;

a calcium-activated potassium channel (Kca) opener or positive modulator;

a potassium channel opener or positive modulator of a potassium voltage-gated channel such as a member of subfamily A (e.g. Kv1.1), subfamily B (e.g. Kv2.2) or subfamily K (e.g. TASK, TREK or TRESK);

or the pharmaceutically acceptable salts or the solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Compositions for oral administration are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, micro-crystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilizing a compound of formulae (I), (II) and (III) or pharmaceutically acceptable salt thereof and a sterile vehicle. Formulations for injection may be presented in unit dosage form e.g. in ampoules or in multi-dose, utilizing a compound of formulae (I), (II) and (III) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in, the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

Compounds of formulae (I), (II) and (III) or pharmaceutically acceptable salts thereof may also be formulated in rectal compositions such as suppositories or retention enemas, e.g. containing conventional suppository bases such as cocoa butter or other glycerides.

Compounds of formulae (I), (II) and (III) or pharmaceutically acceptable salts may also be formulated as depot preparations. Such long acting formulations may be administered by implantation (for example subcutaneously or intramuscularly) or by intramuscular injection. Thus, for example, the compounds of formulae (I), (II) and (III) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, compounds of formulae (I), (II) and (III) or pharmaceutically acceptable salts thereof may be formulated as solutions for administration via a suitable metered or unitary dose device or alternatively as a powder mix with a suitable carrier for administration using a suitable delivery device. Thus, compounds of formulae (I), (II) and (III) or pharmaceutically acceptable salts thereof may be formulated for oral, buccal, parenteral, and topical (including dermal, ophthalmic and nasal), depot or rectal administration or in a form suitable for administration by inhalation or insufflation (either through the mouth or nose). The compounds of formulae (I), (II) and (III) and pharmaceutically acceptable salts thereof may be formulated for topical administration in the form of ointments, creams, gels, emulsion, lotions, pack, pessaries, aerosols or drops (e.g. eye, ear or nose drops) and the like. Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

DCM Dichloromethane
DMF N,N-Dimethylformamide
DMA N,N-Dimethylacetamide
DME 1,2-Dimethoxyethane
DMSO Dimethyl sulfoxide
EDC 1-Ethyl-3-(3-dimethylaminopropyl)carbodiimide Hydrochloride
e.e. Enantiomeric Excess
ESI Electrospray Ionization
EtOAc Ethyl acetate
EtOH Ethanol
Ex Example
HOBT 1-Hydroxybenztriazole
HATU O-(7-Azabenzotriazol-1-yl)-N,N,N',N'-tetramethyluronium Hexafluorophosphate
HBTU O-(Benzotriazol-1-yl)-N,N,N',N'-tetramethyluronium Hexafluorophosphate
HPLC High-Performance Liquid Chromatography
LC Liquid Chromatography
LG Leaving Group
tR Retention Time MeCN Acetonitrile
MeOH Methanol
MHz Megahertz
MS Mass Spectrometry
NMR Nuclear Magnetic Resonance
rt Room Temperature
T3P Propylphosphonic Acid Anhydride (Cyclic Trimer, registered trademark)
TFA Trifluoroacetic Acid
THF Tetrahydrofuran
TLC Thin Layer Chromatography
UV Ultraviolet The term of "base" is likewise no particular restriction on the nature of the bases used, and any base commonly used in reactions of this type may equally be used here. Examples of such bases include, but not limited to: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogen-carbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl) amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, DMA, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane and chloroform are preferred.

EXAMPLES

The invention is illustrated in the following non-limiting examples in which, unless stated otherwise: all reagents are commercially available, all operations are carried out at room or ambient temperature, that is, in the range of about 18-25° C.; microwave reactions are carried out using Biotage Initiator or Biotage Initiator+; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography is carried out using Biotage SNAP KP-Sil, Biotage SNAP Isolute NH2, Merck silica gel 60 (230-400 mesh ASTM), Fuji Silysia Chromatorex (registered trademark) NH-DM1020 and NH-DM2035, Wako Wakogel C300-HG, Yamazen Hi-FLASH column, or YMC DispoPack-SIL. Ion-exchange chromatography is carried out using a strong cation exchange cartridge (ISOLUTE (registered trademark) SCX, 1 g/6 mL, Biotage), or strong anion exchange cartridge (ISOLUTE (registered trademark) PE-AX, 1 g/6 mL, Biotage). The purification of compounds using HPLC (preparative LC-MS) is performed by the following apparatus and conditions.

Apparatus; Waters MS-trigger AutoPurification (registered trademark) system

Column; Waters XTerra C18, 19×50 mm, 5 micrometer particle

Condition A: Methanol or acetonitrile/0.01%(v/v) ammonia aqueous solution.

Condition B: Methanol or acetonitrile/0.05%(v/v) formic acid aqueous solution Low-resolution mass spectral data (ESI) are obtained by the following apparatus and conditions: Apparatus; Waters Alliance HPLC system on ZQ or ZMD mass spectrometer and UV detector. NMR data are determined at 270 MHz (JEOL JNM-LA 270 spectrometer), 300 MHz (JEOL JNM-LA300), or 400 MHz (JEOL JNM-ECZ400S) using deuterated chloroform (99.8% D) or dimethyl sulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L(liter(s)), mL (milliliter(s)), g (gram(s)), mg(milligram(s)), mol (moles), mmol (millimoles).

Each prepared compound is generally named by ChemBioDraw (Ultra, version 12.0, CambridgeSoft).

Conditions for determining HPLC retention time:

Method A

Apparatus: Waters Acquity Ultra Performance LC on TUV Detector and ZQ mass spectrometer Column: Waters ACQUITY C18, 2.1×100 mm, 1.7 um particle Column Temperature: 60° C.

PDA detection: 210 nm scan

MS detection: ESI positive/negative mode

Solvents:

A1: 10 mM ammonium acetate aqueous solution

B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| run time | 3 min | |
| Flow rate | 0.7 mL/min | |

Method B

Apparatus: Waters Acquity Ultra Performance LC on PDA Detector and ZQ mass spectrometer Column: Waters ACQUITY C18, 2.1×100 mm, 1.7 um particle Column Temperature: 60° C.

PDA detection: 200-400 nm scan

MS detection: ESI positive/negative mode

Solvents:

A1: 10 mM ammonium acetate aqueous solution

B1: acetonitrile

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| run time | 3 min | |
| Flow rate | 0.7 mL/min | |

Method C

Apparatus: Waters Acquity Ultra Performance LC on PDA Detector and ZQ mass spectrometer Column: YMC Triart C18, 2.1×100 mm, 1.9 um particle Column Temperature: 60° C.

PDA detection: 200-400 nm scan

MS detection: ESI positive/negative mode

Solvents:

A1: 10 mM ammonium acetate aqueous solution

B1: acetonitrile

| Time(min) | A1(%) | B1(%) |
|---|---|---|
| 0 | 90 | 10 |
| 0.05 | 90 | 10 |
| 1.9 | 5 | 95 |
| 2.5 | 5 | 95 |
| 2.51 | 90 | 10 |
| run time | 3 min | |
| Flow rate | 0.75 mL/min | |

All of the amide derivatives of the formulae (I), (II) and (III) can be prepared by the procedures described in the general methods presented below or by the specific methods described in the Example synthesis part and Intermediate synthesis part, or by routine modifications thereof. The present invention also encompasses any one or more of these processes for preparing the amide derivatives of formulae (I), (II) and (III), in addition to any novel intermediates used therein.

In the following general methods, descriptors are as previously defined for the amide derivatives of the formulae (I), (II) and (III) unless otherwise stated. All starting materials in the following general syntheses may be commercially available or obtained by the conventional methods known to those skilled in the art, otherwise noted in the intermediate synthesis part.

<Scheme A>

[Chem.4]

In Step A, a compound of formula (I) can be prepared from a compound of formula (IV-a) by amidation with a compound of formula (IV-b) using a suitable condensation agent such as HBTU, HATU, T3P (registered trademark), and EDC-HOBT, preferably under the presence of a base such as triethylamine and N,N-diisopropylethylamine in a suitable solvent such as DMF, DMA and DCM at a temperature of from about 5 to 60° C. for about 1-24 hours. In addition, a compound of formula (I) can be also prepared from a compound of formula (IV-a) by amidation with an acid halide prepared from a compound of formula (1V-b) using thionyl chloride or oxalyl chloride, preferably under the presence of a base such as triethylamine, pyridine, and N,N-diisopropylethylamine in a suitable solvent such as DCM at a temperature of from about 5 to 40° C. for about 1-24 hours.

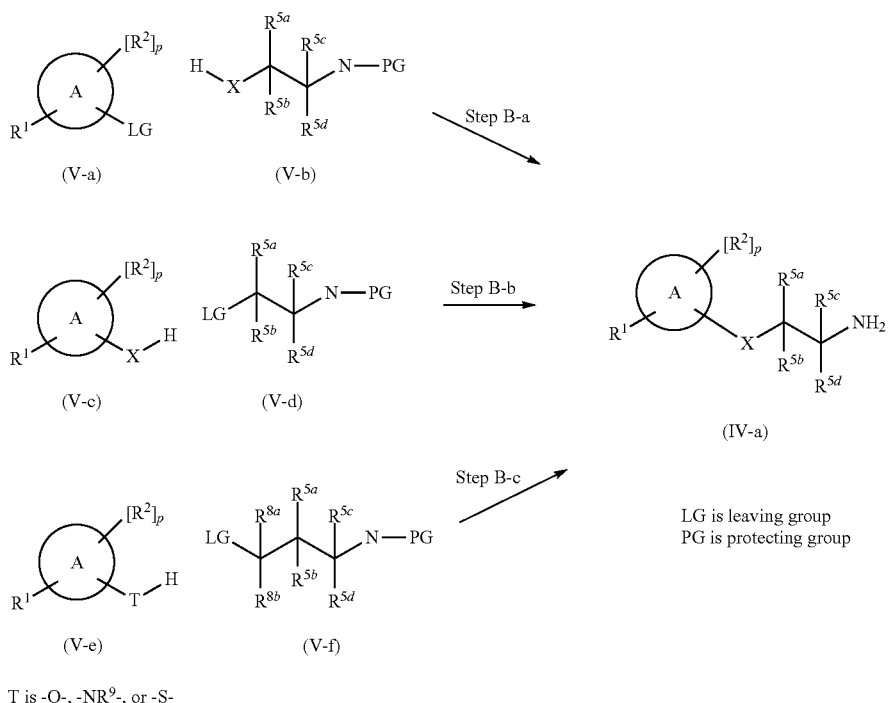

In Step B-a, a compound of formula (IV-a) can be prepared from a compound of formula (V-a) and a compound of formula (V-b) by $S_N$—Ar reaction, preferably under the presence of a base such as sodium hydroxide, potassium hydroxide, potassium carbonate, sodium carbonate, cesium carbonate, potassium tert-butoxide, and sodium hydride in a suitable solvent such as DMF, DMA and DCM at a temperature of from about 5 to 100° C. for about 1-24 hours.

In the case that X is —O—, —NR$^9$—, or —S—, a compound of formula (IV-a) can be prepared in step B-b by alkylation of a compound of formula (V-c) with an alkylating reagent (V-d) using a suitable base such as sodium hydride, potassium carbonate, cesium carbonate, and potassium tert-butoxide in a suitable solvent such as DMF, DMA, THF and DCM at a temperature of from about 5 to 100° C. for about 1-24 hours.

In the case that X is —O—CR$^{8a}$R$^{8b}$—, —NR$^9$—CR$^{8a}$R$^{8b}$—, or —S—CR$^{8a}$R$^{8b}$—, a compound of formula (IV-a) can be prepared in step B-c from a compound of formula (V-e) and an alkylating reagent (V-f) in a similar manner to Step B-b, wherein X in formula (IV-a) is regarded as T-CR$^{8a}$R$^{8b}$.

In Steps B-a, B-b, and B-c, deprotection of the protecting group can be carried out by the conventional methods known to those skilled in the art (typical amino protecting groups described in "Protective Groups in Organic Synthesis Forth Edition" edited by T. W. Greene et al. (John Wiley & Sons, 2007).

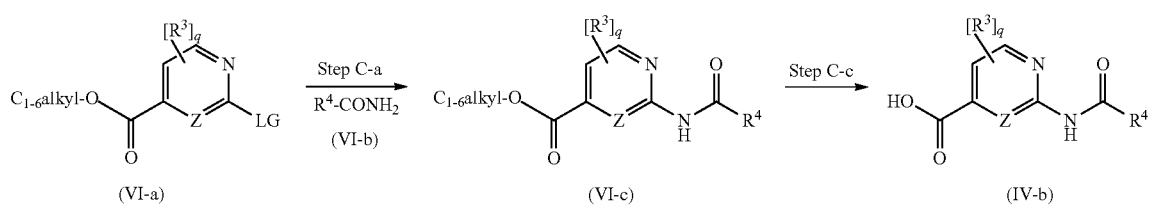

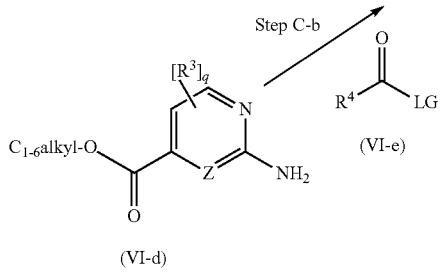

(VI-d)

When a leaving group of formula (VI-a), in Step C-a, is such as O-trifluoromethanesulfonate, O-tosylate, O-mesylate, iodide, bromide, and chloride, a compound of formula (VI-c) can be prepared by coupling of a compound of formula (VI-a) with a suitable carboxamide of formula (VI-b) under coupling conditions in suitable organic solvents in the presence of a suitable transition metal catalyst and in the presence or absence of a base. Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bis(acetonitrile)dichloropalladium(II), bis(dibenzylideneacetone)palladium(0), tis(dibenzylideneacetone)dipalladium(0) and [1,1'-bis(diphenylphosphino)ferrocene]palladium(II) dichloride. Preferred catalysts are tetrakis(triphenylphosphine)palladium(0), bis(triphenylphosphine)palladium(II) chloride, palladium(II) acetate, palladium(II) chloride, bis(acetonitrile)dichloropalladium(0), bis(dibenzylideneacetone)palladium(0), tris(dibenzylideneacetone)dipalladium(0) and [1,1-bis(diphenylphosphino)ferrocene]palladium(II) dichloride. Examples of suitable carboxamide include, but not limited to, carboximides such as acetamide, propionamide, isobutyramide and cyclopropanecarboxamide. Examples of suitable organic solvent include: THF; 1,4-dioxane; DMF; MeCN; alcohols, such as methanol or ethanol; halogenated hydrocarbons, such as DCM, 1,2-dichloroethane, chloroform or carbon tetrachloride; and diethylether; in the presence or absence of base such as tripotassium phosphate, sodium bicarbonate, sodium carbonate or potassium carbonate. This reaction can be carried out in the presence of a suitable additive agent. Examples of such additive agents include: 4,5-Bis(diphenylphosphino)-9,9-dimethylxanthene, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine. The reaction can be carried out at a temperature of from about 50 to 200° C., more preferably from about 80 to 150° C. Reaction times are, in general, from about 5 minutes to 48 hrs, more preferably from about 30 minutes to 24 hrs. In an alternative case, the reaction can be carried out with microwave system. The reaction can be carried out at a temperature in the range from about 100 to 200° C., preferably in the range from about 120 to 160° C. Reaction times are, in general, from about 10 minutes to 3 hrs, preferably from about 15 minutes to 1 hr.

Alternatively, a compound of formula (VI-c) can be prepared, in Step C-b, by acylation with a suitable acid halide of formula (VI-e) using a suitable base such as pyridine and a suitable solvent such as DMA at a temperature of from about 5 to 120° C. for about 1-24 hours. Examples of suitable acid halide include, but not limited to, such as acetyl chloride, propionyl chloride, isobutyryl chloride, and cyclopropanecarbonyl chloride.

In Step C-c, a compound of formula (IV-b) can be prepared by hydrolysis of the ester compound of formula (VI-c). The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, for example: alcohols such as water, methanol, ethanol, propanol, butanol, 2-methoxyethanol, and ethylene glycol; ethers such as THF, DME, and 1,4-dioxane; amides such as DMF and hexamethylphosphorictriamide; and sulfoxides such as DMSO. Preferred solvents are water, methanol, ethanol, propanol, THF, DME, 1,4-dioxane, DMF, and DMSO. This reaction can be carried out at a temperature in the range of from about −20 to 100° C. for from about 30 minutes to 24 hrs.

Intermediate Synthesis Part

All starting materials in the intermediate syntheses may be commercially available or obtained by conventional methods known to those skilled in the art unless otherwise stated.

<Amine Part>

Amine-5: (R)-2-((3-chloro-5-(trifluoromethyl)pyridin-2-yl)oxy)propan-1-amine hydrochloride <Step-1>: tert-butyl (R)-(2-((3-chloro-5-(trifluoromethyl)pyridin-2-yl)oxy)propyl)carbamate To a stirred solution of tert-butyl (R)-(2-hydroxypropyl)carbamate (389 mg, 2.22 mmol) and sodium hydride (60%, 89 mg, 2.22 mmol) in DMF (12 mL) and THF (2 mL) is added 2,3-dichloro-5-(trifluoromethyl)pyridine (400 mg, 1.85 mmol) at 0° C. The resulting mixture is stirred at rt for 1 hour. The reaction mixture, is poured onto ice-water (50 mL), and extracted with EtOAc/hexane (4:1, 50 mL). The organic layer is washed with water (50 mL×2), and dried over sodium sulfate. After removal of the solvent, the residue is purified by column chromatography on silica-gel eluting with n-hexane/EtOAc (100:1 to 20:1) to give 166 mg (25% yield) of the title compound as a colorless oil.

$^1$H-NMR (400 MHz, CDCl$_3$) delta 8.31 (1H, d, J=1.8 Hz), 7.85 (1H, d, J=1.8 Hz), 5.43-5.34 (1H, m), 4.87 (1H, br.s), 3.60-3.50 (1H, m), 3.42-3.32 (1H, m), 1.43 (9H, s), 1.38 (3H, d, J=6.4 Hz), MS (ESI) m/z: 355 (M+H)$^+$.

<Step-2>: (R)-2-((3-chloro-5-(trifluoromethyl)pyridin-2-yl)oxy)propan-1-amine hydrochloride A mixture of tert-butyl (R)-(2-((3-chloro-5-(trifluoromethyl)pyridin-2-yl)oxy)propyl)carbamate (166 mg, 0.47 mmol, Step-1) and 4M hydrogen chloride solution in 1,4-dioxane (8 mL) is stirred at rt for 1 hour. After removal of the solvent, the residual solid is washed with isopropyl ether and hexane to give 134 mg (98% yield) of the title compound as a white solid.

MS (ESI) m/z: 255 (M+H)$^+$.

Amine-10: 2-((3-fluoro-5-(trifluoromethyl)pyridin-2-yl)oxy)ethanamine hydrochloride <Step-1>: 2-(2-((3-fluoro-5-(trifluoromethyl)pyridin-2-yl)oxy)ethyl)isoindoline-1,3-dione To a stirred solution of 2-(2-hydroxyethyl)isoindoline-1,3-dione (459 mg, 2.40 mmol) and sodium hydride (60%, 96 mg, 2.40 mmol) in DMF (8 mL) and THF (2 mL) is added 2,3-difluoro-5-(trifluoromethyl)pyridine (400 mg, 2.19 mmol) at 0° C. The resulting mixture is stirred at rt for 1 hour. The reaction mixture is poured onto ice-water (50 mL), and extracted with EtOAc/hexane (4:1, 50 mL). The organic layer is washed with water (50 mL×2), and dried over sodium sulfate. After removal of the solvent, the residue is purified by column chromatography on silica-gel eluting with n-hexane/EtOAc (4:1) to give 390 mg (50% yield) of the title compound as a white solid.

$^1$H-NMR (400 MHz, CDCl$_3$) delta 8.13-8.12 (1H, m), 7.87-7.82 (2H, m), 7.75-7.71 (2H, m), 7.51 (1H, dd, J=9.1, 1.8 Hz), 4.75 (2H, t, J=5.5 Hz), 4.15 (2H, t, J=5.5 Hz), MS (ESI) m/z: 355 (M+H)$^+$.

<Step-2>: 2-((3-fluoro-5-(trifluoromethyl)pyridin-2-yl)oxy)ethanamine hydrochloride A mixture of 2-(2-((3-fluoro-5-(trifluoromethyl)pyridin-2-yl)oxy)ethyl)isoindoline-1,3-dione (390 mg, 1.10 mmol, Step-1), hydrazine monohydrate (0.17 mL, 5.50 mmol), and methanol (8 mL) is stirred at 50° C. for 4 hours. After cooling to rt, the precipitate is removed by filtration. After evaporation of the filtrate, the residue is dissolved in 1M NaOH (50 mL), and extracted with DCM (50 mL×2). The combined organic fraction is dried over sodium sulfate, and concentrated under reduced pressure. The residue is treated with 2M hydrogen chloride solution in 1,4-dioxane (8 mL) at rt for 5 min. After removal of the solvent, the residual solid is washed with isopropyl ether and hexane to give 185 mg (65% yield) of the title compound as a white solid.

$^1$H-NMR (400 MHz, DMSO-d$_6$) delta 8.43 (1H, s), 8.26 (1H, dd, J=10.5, 1.8 Hz), 8.12 (2H, br.s), 4.64-4.60 (2H, m), 3.27-3.24 (2H, m), MS (ESI) m/z: 225 (M+H)$^+$.

Amine-11: 2-(4-(pentafluorosulfanyl)phenoxy)ethanamine

<Step-1>: tert-butyl (2-(4-(pentafluorosulfanyl)phenoxy)ethyl)carbamate

To a stirred solution of tert-butyl (2-hydroxyethyl)carbamate (419 mg, 2.60 mmol) and sodium hydride (60%, 144 mg, 3.60 mmol) in DMF (10 mL) is added p-fluorophenylsulfur pentafluoride (444 mg, 2.00 mmol) at 0° C. The resulting mixture is stirred at rt overnight. The reaction mixture is poured onto ice-water (50 mL), and extracted with EtOAc/hexane (4:1, 50 mL). The organic layer is washed with water (50 mL×2), and dried over sodium sulfate. The solvent is removed by evaporation to give 727 mg (>99% yield) of the title compound. This material is used for the next reaction (Step-2) without further purification.

MS (ESI) m/z: 408 (M+HCOO)$^-$.

<Step-2>: 2-(4-(pentafluorosulfanyl)phenoxy)ethanamine

A mixture of tert-butyl (2-(4-(pentafluorosulfanyl)phenoxy)ethyl)carbamate (182 mg, 0.50 mmol, Step-1) and 4M hydrogen chloride solution in EtOAc (3 mL) is stirred at rt for 0.5 hour. After removal of the solvent, the residue is diluted with methanol (12 mL) and applied onto a strong cation exchange cartridge (ISOLUTE (registered trademark) SCX, 1 g/6 mL×4, Biotage), and the solid phase matrix is rinsed with methanol (5 mL×4). The material is eluted with 1M ammonia in methanol (5 mL×4), and combined eluate is concentrated under reduced pressure to give 83 mg (63% yield) of the title compound.

MS (ESI) m/z: 264 (M+H)$^+$.

Amine-12: 2-((6-(trifluoromethyl)quinolin-2-yl)oxy)ethanamine hydrochloride

<Step-1>: tert-butyl (2-((6-(trifluoromethyl)quinolin-2-yl)oxy)ethyl)carbamate

The title compound is prepared in 54% yield (167 mg, a white solid) from 2-chloro-6-(trifluoromethyl)quinoline (200 mg, 0.86 mmol) and tert-butyl (2-hydroxyethyl)carbamate (167 mg, 1.04 mmol) by the similar manner in Step-1 of Amine-5.

$^1$H-NMR (400 MHz, CDCl$_3$) delta 8.06 (1H, d, J=8.7 Hz), 8.02 (1H, s), 7.91 (1H, d, J=8.7 Hz), 7.80 (1H, dd, J=8.7; 1.8 Hz), 6.99 (1H, d, J=8.7 Hz), 5.11 (1H, br.s), 4.59-4.56 (2H, m), 3.64-3.58 (2H, m), 1.45 (9H, s), MS (ESI) m/z: 357 (M+H)$^+$.

<Step-2>: 2-((6-(trifluoromethyl)quinolin-2-yl)oxy)ethanamine hydrochloride

The title compound is prepared in >99% yield (137 mg, a white solid) from tert-butyl (2-((6-(trifluoromethyl)quinolin-2-yl)oxy)ethyl)carbamate (167 mg, 0.47 mmol, Step-1) by the similar manner in Step-2 of Amine-5.

MS (ESI) m/z: 257 (M+H)$^+$.

Amine-13: N$^1$-(6-(trifluoromethyl)quinolin-2-yl)ethane-1,2-diamine hydrochloride <Step-1>: tert-butyl(2-((6-(trifluoromethyl)quinolin-2-yl)amino)ethyl)carbamate A mixture of 2-chloro-6-(trifluoromethyl)quinoline (110 mg, 0.48 mmol), tert-butyl (2-aminoethyl)carbamate (91 mg, 0.57 mmol), and potassium carbonate (197 mg, 1.43 mmol) in DMF (3 mL) is stirred at 100° C. for 3 hours. After cooling to rt, the reaction mixture is poured into water (20 mL), and extracted with EtOAc/hexane (4:1, 30 mL). The organic layer is washed with water (20 mL×2), and dried over sodium sulfate. After removal of the solvent, the residue is purified by column chromatography on silica-gel eluting with n-hexane/EtOAc (5:1 to 4:1) to give 50 mg (30% yield) of the title compound as a white foam.

$^1$H-NMR (400 MHz, CDCl$_3$) delta 7.85-7.81 (2H, m), 7.74-7.67 (2H, m), 6.69 (1H, d, J=8.7 Hz), 5.59 br.s), 5.49 (1H, br.s), 3.70-3.65 (2H, m), 3.47-4.42 (2H, m), 1.43 (9H, s), MS (ESI) m/z: 356 (M+H)$^+$.

<Step-2>: N¹-(6-(trifluoromethyl)quinolin-2-yl) ethane-1,2-diamine hydrochloride The title compound is prepared in >99% yield (42 mg, a white solid) from tert-butyl (2-((6-(trifluoromethyl)quinolin-2-yl)amino)ethyl)carbamate (50 mg, 0.14 mmol, Step-1) by the similar manner in Step-2 of Amine-5.
MS (ESI) m/z: 256 (M+H)⁺.

Amine-14: 2-((6-(trifluoromethyl)isoquinolin-1-yl) oxy)ethananine hydrochloride

<Step-1>: tert-butyl (2((6-(trifluoromethyl)isoquinolin-1-yl)oxy)ethyl)carbamate The title compound is prepared in 43% yield (66 mg, a colorless oil) from 1-chloro-6-(trifluoromethyl)isoquinoline (100 mg, 0.43 mmol) and tert-butyl (2-hydroxyethyl)carbamate (84 mg, 0.52 mmol) by the similar manner in Step-1 of Amine-5.
¹H-NMR (400 MHz, CDCl₃) delta 8.38 (1H, d, J=8.7 Hz), 8.07 (1H, dd, J=5.9, 1.8 Hz), 8.04 (1H, s), 7.71 (1H, dd, J=8.7, 1.8 Hz), 7.31 (1H, d, J=5.9 Hz), 5.01 (1H, br.s), 4.62-4.59 (2H, m), 3.70-3.60 (2H, m), 1.45 (9H, s), MS (ESI) m/z: 357 (M+H)⁺.

<Step-2>: 2-((6-(trifluoromethyl)isoquinolin-1-yl) oxy)ethanamine hydrochloride

The title compound is prepared in >99% yield (54 mg, a white solid) from tert-butyl (2-((6-(trifluoromethyl)isoquinolin-1-yl)oxy)ethyl)carbamate (66 mg, 0.19 mmol, Step-1) by the similar manner in Step-2 of Amine-5.
MS (ESI) m/z: 257 (M+H)⁺.

Amine-15: 2-((6-(2,2,2-trifluoroethoxy)naphthalen-2-yl)oxy)ethanamine hydrochloride <Step-1>: 6-(2,2,2-trifluoroethoxy)naphthalen-2-ol A mixture of naphthalene-2,6-diol (500 mg, 3.12 mmol), 2,2,2-trifluoroethyl trifluoromethanesulfonate (797 mg, 3.43 mmol), and potassium carbonate (863 mg, 6.24 mmol) in DMF (10 mL) is stirred at rt for 2 hours. The reaction mixture is diluted with 1M HCl (100 mL), and extracted with EtOAc/hexane (4:1, 100 mL). The organic layer is washed with water (100 mL×2), and dried over sodium sulfate. After removal of the solvent, the residue is purified by column chromatography on silica-gel eluting with n-hexane/EtOAc (4:1) to give 265 mg (35% yield) of the title compound as a white solid.
¹H-NMR (400 MHz, CDCl₃) delta 7.66-7.63 (2H, m), 7.18 (1H, dd, J=9.1, 2.7 Hz), 7.14-7.09 (3H, m), 4.94 (1H, s), 4.44 (2H, q, J=8.2 Hz), MS (ESI) m/z: 241 (M−H)⁻.

<Step-2>: tert-butyl (2-((6-(2,2,2-trifluoroethoxy) naphthalen-2-yl)oxy)ethyl)carbamate A mixture of 6-(2,2,2-trifluoroethoxy)naphthalen-2-ol (265 mg, 1.09 mmol, Step-1), tert-butyl (2-bromoethyl) carbamate (294 mg, 1.31 mmol), and potassium carbonate (454 mg, 3.28 mmol) in DMF (6 mL) is stirred at 60° C. for 4 hours. After cooling to rt, the reaction mixture is poured into water (50 mL), and extracted with EtOAc/hexane (4:1, 50 mL). The organic layer is washed with water (50 mL×2), and dried over sodium sulfate. After removal of the solvent, the residue is purified by column chromatography on silica-gel eluting with n-hexane/EtOAc (4:1) to give 288 mg (68% yield) of the title compound as a white solid.
¹H-NMR (400 MHz, CDCl₃) delta 7.66 (2H, t, J=9.6 Hz), 7.20-7.10 (4H, m), 5.03 (1H, br.s), 4.45 (2H, q, J=8.2 Hz), 4.14-4.10 (2H, m), 3.62-3.58 (2H, m), 1.46 (9H, s), MS (ESI) m/z: 430 (M+HCOO)⁻.

<Step-3>: 24(6-(2,2,2-trifluoroethoxy)naphthalen-2-yl)oxy)ethanamine hydrochloride The title compound is prepared in 93% yield (223 mg, a white solid) from tert-butyl (2-((6-(2,2,2-trifluoroethoxy) naphthalen-2-yl)oxy)ethyl)carbamate (288 mg, 0.75 mmol, Step-2) by the similar manner in Step-2 of Amine-5.
MS (ESI) m/z: 286 (M+H)⁺.

Amine-17: (R)-1-((3-chloro-5-(trifluoromethyl)pyridin-2-yl)oxy)propan-2-amine hydrochloride <Step-1>: tert-butyl (R)-(1-((3-chloro-5-(trifluoromethyl)pyridin-2-yl)oxy)propan-2-yl)carbamate The title compound is prepared in 74% yield (483 mg, a white solid) from 2,3-dichloro-5-(trifluoromethyl)pyridine (400 mg, 1.85 mmol) and tert-butyl (R)-(1-hydroxypropan-2-yl)carbamate (389 mg, 2.22 mmol) by the similar manner in Step-1 of Amine-5.
¹H-NMR (400 MHz, CDCl₃) delta 8.31 (11-1, s), 7.85 (1H, d, J=2.3 Hz), 4.72 (1H, br.s), 4.45-4.34 (2H, m), 4.16 (1H, br.s), 1.44 (9H, s), 1.29 (3H, d, J=6.9 Hz), MS (ESI) m/z: 399 (M+HCOO)⁻.

<Step-2>: (R)-1-((3-chloro-5-(trifluoromethyl)pyridin-2-yl)oxy)propan-2-amine hydrochloride The title compound is prepared in 97% yield (383 mg, a white solid) from tert-butyl (R)-(1-((3-chloro-5-(trifluoromethyl)pyridin-2-yl)oxy)propan-2-yl)carbamate (483 mg, 1.36 mmol, Step-1) by the similar manner in Step-2 of Amine-5.
MS (ESI) m/z: 255 (M+H)⁺.

Amine-18: (S)-2-((3-chloro-5-(trifluoromethyl)pyridin-2-yl)oxy)propan-1-amine hydrochloride <Step-1>: tert-butyl (S)-(2-((3-chloro-5-(trifluoromethyl)pyridin-2-yl)oxy)propyl)carbamate The title compound is prepared in 32% yield (213 mg, a colorless oil) from 2,3-dichloro-5-(trifluoromethyl)pyridine (400 mg, 1.85 mmol) and tert-butyl (S)-(2-hydroxypropyl) carbamate (389 mg, 2.22 mmol) by the similar manner in Step-1 of Amine-5.
¹H-NMR (400 MHz, CDCl₃) delta 8.31 (1H, d, J=1.8 Hz), 7.85 (I H, d, J=1.8 Hz), 5.43-5.34 (1H, m), 4.87 (1H, br.s), 3.60-3.50 (1H, m), 3.42-3.32 (1H, m), 1.43 (9H, s), 1.38 (3H, d, J=6.4 Hz), MS (ESI) m/z: 355 (M+H)⁺.

<Step-2>: (S)-2-((3-chloro-5-(trifluoromethyl)pyridin-2-yl)oxy)propan-1-amine hydrochloride The title compound is prepared in 99% yield (173 mg, a white solid) from tert-butyl (S)-(2-((3-chloro-5-(trifluoromethyl)pyridin-2-yl)oxy)propyl)carbamate (213 mg, 0.60 mmol, Step-1) by the similar manner in Step-2 of Amine-5.
MS (ESI) m/z: 255 (M+H)⁺.

Amine-19: 2-((7-(trifluoromethyl)quinolin-4-yl)oxy)ethanamine trifluoroacetate <Step-1>: tert-butyl (2((7-(trifluoromethyl)quinolin-4-yl)oxy)ethyl)carbamate The title compound is prepared in 8% yield (48 mg, a pale yellow solid) from 4-chloro-7-(trifluoromethyl)quinoline (400 mg, 1.73 mmol) and tert-butyl (2-hydroxyethyl)carbamate (334 mg, 2.07 mmol) by the similar manner in Step-1 of Amine-5.

$^1$H-NMR (400 MHz, CDCl$_3$) delta 8.64 (OH, d, J=5.0 Hz), 8.27 (1H, s), 7.89 (1H, d, J=8.7 Hz), 7.60 (1H, d, J=8.7 Hz), 6.50 (1H, d, J=5.0 Hz), 5.83-5.79 (1H, m), 4.50-4.46 (2H, m), 3.65-3.60 (2H, m), 1.50 (9H, s), MS (ESI) m/z: 357 (M+H)$^+$.

<Step-2>: 2-((7-(trifluoromethyl)quinolin-4-yl)oxy)ethanamine trifluoroacetate

A mixture of tert-butyl (2-((7-(trifluoromethyl)quinolin-4-yl)oxy)ethyl)carbamate (48 mg, 0.14 mmol, Step-1), TFA (2 mL) and DCM (2 mL) is stirred at rt for 1 hour. The solvent is concentrated under reduced pressure to give 50 mg (>99% yield) of the title compound as a colorless oil.

MS (ESI) m/z: 257 (M+H)$^+$.

Amine-20: 2-((5-chloro-3-(trifluoromethyl)pyridin-2-yl)oxy)ethanamine hydrochloride <Step-1>: 2-(2-((5-chloro-3-(trifluoromethyl)pyridin-2-yl)oxy)ethyl)isoindoline-1,3-dione The title compound is prepared in 49% yield (475 mg, a white solid) from 2,5-dichloro-3-(trifluoromethyl)pyridine (570 mg, 2.64 mmol) and 2-(2-hydroxyethyl)isoindoline-1,3-dione (555 mg, 2.90 mmol) by the similar manner in Step-1 of Amine-10.

$^1$H-NMR (400 MHz, CDCl$_3$) delta 8.20 (1H, d, J=1.8 Hz), 7.88-7.82 (2H, m), 7.80 (1H, d, J=1.8 Hz), 7.74-7.70 (2H, m), 4.68 (2H, t, J=5.7 Hz), 4.14 (2H, t, J=5.7 Hz), MS (ESI) m/z: 371 (M+H)$^+$.

<Step-2>: 2-((5-chloro-3-(trifluoromethyl)pyridin-2-yl)oxy)ethanamine hydrochloride The title compound is prepared in >99% yield (355 mg, a white solid) from 2-(2-((5-chloro-3-(trifluoromethyl)pyridin-2-yl)oxy)ethyl)isoindoline-1,3-dione (475 mg, 1.28 mmol, Step-1) by the similar manner in Step-2 of Amine-10.

MS (ESI) m/z: 241 (M+H)$^+$.

Amine-21: 2-((4-(trifluoromethyl)quinolin-2-yl)oxy)ethanamine hydrochloride

<Step-1>: 2-(2-((4-(trifluoromethyl)quinolin-2-yl)oxy)ethyl)isoindoline-1,3-dione The title compound is prepared in 32% yield (213 mg, a white solid) from 2-chloro-4-(trifluoromethyl)quinoline (400 mg, 1.73 mmol) and 2-(2-hydroxyethyl)isoindoline-1,3-dione (363 mg, 1.90 mmol) by the similar manner in Step-1 of Amine-10.

$^1$H-NMR (400 MHz, CDCl$_3$) delta 7.97 (1H, d, J=8.2 Hz), 7.87-7.78 (31-1, m). 7.73-7.61 (3H, m), 7.48-7.43 (1H, m), 7.19 (1H, s), 4.81 4.78 (2H, m), 4.21-4.18 (2H, m), MS (ESI) m/z: 387 (M+H)$^+$.

<Step-2>: 2((4-(trifluoromethyl)quinolin-2-yl)oxy)ethanamine hydrochloride

The title compound is prepared in >99% yield (161 mg, a white solid) from 2-(2-((4-(trifluoromethyl)quinolin-2-yl)oxy)ethyl)isoindoline-1,3-dione (213 mg, 0.55 mmol, Step-1) by the similar manner in Step-2 of Amine-10.

MS (ESI) m/z: 257 (M+H)$^+$.

Amine-25: 2-(2-chloro-4-(trifluoromethoxy)phenoxy)ethanamine hydrochloride

<Step-1>: tert-butyl (2-(2-chloro-4-(trifluoromethoxy)phenoxy)ethyl)carbamate

The title compound is prepared in >99% yield (669 mg, a white solid) from 2-chloro-4-(trifluoromethoxy)phenol (400 mg, 1.88 mmol) and tert-butyl (2-bromoethyl)carbamate (506 mg, 2.26 mmol) by the similar manner in Step-2 of Amine-15.

$^1$H-NMR (400 MHz, CDCl$_3$) delta 7.30-7.28 (1H, m), 7.11-7.08 (1H, m), 6.91 (1H, d, J=8.7 Hz), 5.03 (1H, br.s), 4.09-4.06 (2H, m), 3.61-3.54 (2H, m), 1.45 (9H, s).

<Step-2>: 2-(2-chloro-4-(trifluoromethoxy)phenoxy)ethanamine hydrochloride

The title compound is prepared in 93% yield (510 mg, a white solid) from tert-butyl (2-(2-chloro-4-(trifluoromethoxy)phenoxy)ethyl)carbamate (669 mg, 1.88 mmol, Step-1) by the similar manner in Step-2 of Amine-5.

MS (ESI) m/z: 256 (M+H)$^+$.

Amine-28: 2-(2-aminoethoxy)-5-(trifluoromethyl)nicotinonitrile trifluoroacetate <Step-1>: tert-butyl (2-((3-cyano-5-(trifluoromethyl)pyridin-2-yl)oxy)ethyl)carbamate The title compound is prepared in 66% yield (425 mg, a white solid) from 2-chloro-5-(trifluoromethyl)nicotinonitrile (400 mg, 1.94 mmol) and tert-butyl (2-hydroxyethyl)carbamate (375 mg, 2.32 mmol) by the similar manner in Step-1 of Amine-5.

$^1$H-NMR (400 MHz, CDCl$_3$) delta 8.61 (1H, d, J=1.8 Hz), 8.12 (1H, d, J=1.8 Hz), 4.94 (1H, br.s), 4.57 (2H, t, J=5.3 Hz), 3.62-3.58 (2H, m), 1.45 (9H, s), MS (ESI) m/z: 332 (M±H)$^+$.

<Step-2>: 2-(2-aminoethoxy)-5-(trifluoromethyl)nicotinonitrile trifluoroacetate

The title compound is prepared in >99% yield (443 mg, a white solid) from tert-butyl (2-((3-cyano-5-(trifluoromethyl)pyridin-2-yl)oxy)ethyl)carbamate (425 mg, 1.28 mmol, Step-1) by the similar manner in Step-2 of Amine-19.

MS (ESI) m/z: 232 (M+H)$^+$.

Amine-31:
2-(2-methoxy-4-(trifluoromethyl)phenoxy)ethanamine hydrochloride <Step-1>: tert-butyl (2-(2-methoxy-4-(trifluoromethyl)phenoxy)ethyl)carbamate The title compound is prepared in >99% yield (436 mg, a white solid) front 2-methoxy-4-(trifluoromethyl)phenol (250 mg, 1.30 mmol) and tert-butyl (2-bromoethyl)carbamate (350 mg, 1.56 mmol) by the similar manner in Step-2 of Amine-15.
$^1$H-NMR (400 MHz, CDCl$_3$) delta 7.19 (1H, dd, J=8.2, 1.8 Hz), 7.08 (1H, d, J=1.8 Hz), 6.94 (1H, d, J=8.2 Hz), 5.10 (1H, br.s), 4.11 (2H, t, J=5.0 Hz), 3.91 (3H, s), 3.62-3.54 (2H, m), 1.45 (9H, s).

<Step-2>:
2-(2-methoxy-4-(trifluoromethyl)phenoxy)ethanamine hydrochloride

The title compound is prepared in 98% yield (347 mg, a white solid) from tert-butyl (2-(2-methoxy-4-(trifluoromethyl)phenoxy)ethyl)carbamate (436 mg, 1.30 mmol, Step-1) by the similar manner in Step-2 of Amine-5.
MS (ESI) m/z: 236 (M+H)$^+$.

Amine-32:
2-(2-methyl-4-(trifluoromethyl)phenoxy)ethanamine hydrochloride <Step-1>: tert-butyl (2-(2-methyl-4-(trifluoromethyl)phenoxy)ethyl)carbamate The title compound is prepared in >99% yield (181 mg, a white solid) from 2-methyl-4-(trifluoromethyl)phenol (100 mg, 0.57 mmol) and tert-butyl (2-bromoethyl)carbamate (153 mg, 0.68 mmol) by the similar manner in Step-2 of Amine-15.
$^1$H-NMR (400 MHz, CDCl$_3$) delta 7.43-7.38 (2H, m), 6.84 (1H, d, J=8.2 Hz), 4.94 (1H, br.s), 4.06 (2H, t, J=5.0 Hz), 3.62-3.52 (2H, m), 2.26 (3H, s), 1.46 (9H, s).

<Step-2>:
2-(2-methyl-4-(trifluoromethyl)phenoxy)ethanamine hydrochloride

The title compound is prepared in >99% yield (145 mg, a white solid) from tert-butyl (2-(2-methyl-4-(trifluoromethyl)phenoxy)ethyl)carbamate (181 mg, 0.57 mmol, Step-1) by the similar manner in Step-2 of Amine-5.
MS (ESI) m/z: 220 (M+H)$^+$.

Amine-33:
2-(3-fluoro-4-(trifluoromethoxy)phenoxy)ethanamine hydrochloride <Step-1>: tert-butyl (2-(3-fluoro-4-(trifluoromethoxy)phenoxy)ethyl)carbamate The title compound is prepared in 89% yield (230 mg, a colorless oil) from 3-fluoro-4-(trifluoromethoxy)phenol (150 mg, 0.77 mmol) and tert-butyl (2-bromoethyl)carbamate (206 mg, 0.92 mmol) by the similar manner in Step-2 of Amine-15.
$^1$H-NMR (400 MHz, CDCl$_3$) delta 7.24-7.17 (1H, m), 6.73 (1H, dd, J=11.6, 2.9 Hz), 6.66 (1H, ddd, J=9.0, 2.9, 1.5 Hz), 4.93 (1H, br.s), 4.00 (2H, t, J=5.2 Hz), 3.53 (2H, q, J=5.2 Hz), 1.45 (9H, s), MS (ESI) m/z: 340 (M+H)$^+$.

<Step-2>:
2-(3-fluoro-4-(trifluoromethoxy)phenoxy)ethanamine hydrochloride

The title compound is prepared in 83% yield (156 mg, a white solid) from tert-butyl (2-(3-fluoro-4-(trifluoromethoxy)phenoxy)ethyl)carbamate (230 mg, 0.68 mmol, Step-1) by the similar manner in Step-2 of Amine-5.
$^1$H-NMR (400 MHz, DMSO-d$_6$) delta 8.25 (3H, br.s), 7.57-7.49 (1H, m), 7.18 (1H, dd, J=1 2.3, 3.0 Hz), 6.92 (1H, ddd, J=9.2, 3.0, 1.6 Hz), 4.24 (2H, t, J=5.0 Hz), 3.21 (2H, t, J=5.0 Hz), MS (ESI) m/z: 240 (M+H)$^+$.

Amine-34:
2-(3-fluoro-4-(trifluoromethyl)phenoxy)ethanamine hydrochloride <Step-1>: tert-butyl (2-(3-fluoro-4-(trifluoromethyl)phenoxy)ethyl)carbamate The title compound is prepared in 87% yield (78 mg, a colorless oil) from 3-fluoro-4-(trifluoromethyl)phenol (50 mg, 0.28 mmol) and tert-butyl (2-bromoethyl)carbamate (81 mg, 0.36 mmol) by the similar manner in Step-2 of Amine-15.
$^1$H-NMR (400 MHz, CDCl$_3$) delta 7.50 (1H, t, J=8.4 Hz), 6.79-6.63 (2H, m), 4.94 (1H, br.s), 4.05 (2H, t, J=5.1 Hz), 3.55 (2H, q, J=5.1 Hz), 1.45 (9H, s), MS (ESI) m/z: 324 (M+H)$^+$.

<Step-2>: 2-(3-fluoro-4-(trifluoromethyl)phenoxy)ethanamine hydrochloride

The title compound is prepared in 93% yield (58 mg, a white solid) from tert-butyl (2-(3-fluoro-4-(trifluoromethyl)phenoxy)ethyl)carbamate (78 mg, 0.24 mmol, Step-1) by the similar manner in Step-2 of Amine-5.
$^1$H-NMR (400 MHz, DMSO-d$_6$) delta 8.18 (3H, br.s), 7.73 (1H, t, J=8.8 Hz), 7.18 (1H, dd, J=12.7, 2.2 Hz), 7.00 (1H, dd, J=8.8, 2.2 Hz), 4.29 (2H, t, J=5.1 Hz), 3.24 (2H, t, J=5.1 Hz), MS (ESI) m/z: 224 (M+H)$^+$.

<Carboxylic Acid Part>

Carboxylic acid-1: 2-propionamidoisonicotinic acid

<Step-1>: Methyl 2-propionamidoisonicotinate

To a stirred solution of methyl 2-aminoisonicotinate (1.00 g, 6.57 mmol) in pyridine (22 mL) is added propionyl chloride (0.69 mL, 7.89 mmol) at 0° C. After stirring at 0° C. for 2 hours, the reaction mixture is poured into 2M hydrochloric acid (100 mL) and extracted with EtOAc (100 mL). The organic layer is dried over sodium sulfate, and concentrated under reduced pressure to give 1.07 g (78% yield) of the title compound as a yellow solid. This material is used for the next reaction (Step-2) without further purification.
$^1$H-NMR (300 MHz, DMSO-d$_6$) delta 10.71 (1H, s), 8.60 (1H, s), 8.47 (1H, d, J=5.1 Hz), 7.50 (1H, dd, J=5.1, 1.1 Hz), 3.88 (3H, s), 2.40 (2H, q, J=7.7 Hz), 1.06 (3H, t, J=7.7 Hz), MS (ESI) m/z: 209 (M+H)$^+$.

<Step-2>: 2-propionamidoisonicotinic acid

A mixture of methyl 2-propionamidoisonicotinate (1.07 g, 5.15 mmol), 2M aqueous sodium hydroxide solution (5 mL)

and methanol (25 mL) is stirred at 50° C. for 2 hours. After removal of the methanol by evaporation, the solution is acidified by 2M hydrochloric acid and extracted with EtOAc. The organic layer is dried over sodium sulfate and concentrated in vacuo. The residual solid is washed with tetrahydrofuran and n-hexane to give 0.76 g (76% yield) of the title compound as a white solid.

$^1$H-NMR (300 MHz, DMSO-$d_6$) delta 10.65 (1H, s), 8.57 (1H, s), 8.44 (1H, d, J=5.1 Hz), 7.48 (1H, d, J=5.1 Hz), 2.40 (2H, q, J=7.3 Hz), 1.06 (3H, t, J=7.3 Hz), MS (ESI) m/z: 195 (M+H)$^+$.

Carboxylic acid-2:
2-(cyclopropanecarboxamido)isonicotinic acid

<Step-1>: methyl 2-(cyclopropanecarboxamido)isonicotinate

The title compound is prepared in 92% yield (1.60 g, a yellow solid) from methyl 2-aminoisonicotinate (1.20 g, 7.89 mmol) and cyclopropanecarbonyl chloride by the similar manner in Step-1 of Carboxylic acid-1.

$^1$H-NMR (300 MHz, DMSO-$d_6$) delta 8.73 (1H, s), 8.39 (1H, d, J=4.4 Hz), 8.28 (1H, br.s), 7.59 (1H, dd, J=5.1, 1.4 Hz), 3.93 (3H, s), 1.59-1.50 (1H, m), 1.17-1.12 m), 0.96-0.89 (2H, m), MS (ESI) m/z: 221 (M+H)$^+$, 219 (M–H)$^-$.

<Step-2>: 2-(cyclopropanecarboxamido)isonicotinic acid

The title compound is prepared in 94% yield (1.41 g, a white solid) from methyl 2-(cyclopropanecarboxamido) isonicotinate (1.60 g, 7.27 mmol, Step-1) by the similar manner in Step-2 of Carboxylic acid-1.

$^1$H-NMR (300 MHz, DMSO-$d_6$) delta 11.02 (1H, s), 8.57 (1H, s), 8.47 (1H, d, J=5.1 Hz), 7.49 (1H, dd, J=5.1, 1.5 Hz), 2.07-1.98 (1H, m), 0.85-0.79 (4H, m), MS (ESI) m/z: 207 (M+H)$^+$, 205 (M–H)$^-$.

Carboxylic acid-3: 2-isobutyramidoisonicotinic acid

<Step-1>: methyl 2-isobutyramidoisonicotinate

The title compound is prepared in 93% yield (2.20 g, a yellow solid) from methyl 2-aminoisonicotinate hydrochloride (2.00 g, 10.6 mmol) and isobutyryl chloride by the similar manner in Step-1 of Carboxylic acid-1.

$^1$H-NMR (270 MHz, CDCl$_3$) delta 8.78 (1H, s), 8.39 (1H, d, J=5.3 Hz), 7.99 (1H, br.s), 7.60 (1H, dd, J=5.3, 1.3 Hz), 3.94 (3H, s), 2.58 (1H, septet, J=7.3 Hz), 1.28 (6H, d, J=7.3 Hz), MS (ESI) m/z: 223 (M+H)$^+$.

<Step-2>: 2-isobutyramidoisonicotinic acid

The title compound is prepared in 87% yield (1.79 g, a white solid) from methyl 2-isobutyramidoisonicotinate (2.20 g, 7.27 mmol, Step-1) by the similar manner in Step-2 of Carboxylic acid-1.

$^1$H-NMR (270 MHz, DMSO-$d_6$) delta 10.65 (1H, s), 8.60 (1H, s), 8.47 (1H, d, J=5.3 Hz), 7.50 (1H, dd, J=5.3, 1.3 Hz), 2.77 (1H, septet, J=6.6 Hz), 1.10 (6H, d, J=6.6 Hz), MS (ESI) m/z: 207 (M–H)$^-$.

Carboxylic acid-4:
2-acetamido-6-methylisonicotinic acid

<Step-1>: methyl 2-acetamido-6-methylisonicotinate

A mixture of methyl 2-chloro-6-methylisonicotinate (2.00 g, 10.8 mmol), acetamide (1.27 g, 21.6 mmol), tris(dibenzylideneacetone)dipalladium(0) (0.20 g, 0.22 mmol), 4,5-bis(diphenylphosphino)-9,9-dimethylxanthene (0.37 g, 0.65 mmol), tripotassium phosphate (2.74 g, 12.9 mind) and 1,4-dioxane (26 mL) is heated by microwave irradiation at 150° C. for 1 hr. After cooling to rt, the mixture is filtered through a pad of celite. The filtrate is concentrated under reduced pressure and the residue is purified by column chromatography on silica gel eluting with n-hexane/EtOAc (4:1 to 1:3) to give 1.99 g (89% yield) of the title compound as a yellow solid.

$^1$H-NMR (270 MHz, CDCl$_3$) delta 8.50 (1H, br.s), 8.17 (1H, br.s), 7.47 (1H, br.s), 3.94 (3H, s), 2.50 (3H, s), 2.22 (3H, s), MS (ESI) m/z; 209 (M+H)$^+$.

<Step-2>: 2-acetamido-6-methylisonicotinic acid

A mixture of methyl 2-acetamido-6-methylisonicotinate (1.99 g, 9.56 mmol, Step-1), 0.5M aqueous sodium hydroxide solution (20 mL, 10.0 mmol) and tetrahydrofuran (64 mL) is stirred at rt for 2.5 hours. The mixture is acidified by 2M hydrochloric acid and the organic solvent is removed by evaporation. The precipitate is collected by filtration and washed with diisopropyl ether to give 0.81 g (44% yield) of the title compound as a slight yellow solid.

$^1$H-NMR (270 MHz, DMSO-$d_6$) delta 10.60 (1H, s), 8.34 (1H, s), 7.36 (1H, s), 2.45 (3H, s), 2.08 (3H, s), MS (ESI) m/z: 195 (M+H)$^+$.

Carboxylic acid-5:
2-isobutyramido-6-methylisonicotinic acid

<Step-1>: methyl 2-isobutyramido-6-methylisonicotinate

The title compound is prepared in quantitative yield (1.27 g, yellow syrup) from methyl 2-chloro-6-methylisonicotinate (1.00 g, 5.39 mmol) and isobutyramide by the similar manner in Step-1 of Carboxylic acid-4.

$^1$H-NMR (300 MHz, CDCl3) delta 8.57 (1H, s), 7.89 (1H, br.s), 7.47 (1H, s), 3.93 (3H, s), 2.54 (1H, septet, J=6.6 Hz), 2.51 (3H, s), 1.27 (6H, d, J=6.6 Hz), MS (ESI) m/z: 237 (M+H)$^+$.

<Step-2>: 2-isobutyramido-6-methylisonicotinic acid

The title compound is prepared in 88% yield (1.05 g, a pale pink solid) from methyl 2-isobutyramido-6-methylisonicotinate (1.00 g, 5.39 mmol, Step-1) by the similar manner in Step-2 of Carboxylic acid-1.

$^1$H-NMR (300 MHz, DMSO-$d_6$) delta 10.58 (1H, s), 8.39 (1H, s), 7.37 (1H, s), 2.74 (1H, septet, J=6.6 Hz), 2.46 (3H, s), 1.06 (6H, d, J=6.6 Hz), MS (ESI) m/z: 223 (M+H)$^+$.

Carboxylic acid-6: 2-(cyclopropanecarboxamido)-6-methylpyrimidine-4-carboxylic acid <Step-1>: methyl 2-(cyclopropanecarboxamido)-6-methylpyrimidine-4-carboxylate The title compound is prepared in 71% yield (2.70 g, brown oil) from methyl 2-chloro-6-methylpyrimidine-4-carboxylate (3.00 g, 16.1 mmol) and cyclopropanecarboxamide by the similar manner in Step-1 of Carboxylic acid-4.
MS (ESI) m/z: 236 (M+H)⁺, 234 (M−H)⁻.

<Step-2>: 2-(cyclopropanecarboxamido)-6-methylpyrimidine-4-carboxylic acid

The title compound is prepared in 73% yield (1.85 g, a pale yellow solid) from methyl 2-(cyclopropanecarboxamido)-6-methylpyrimidine-4-carboxylate (2.70 g, 11.5 mmol, Step-1) by the similar manner in Step-2 of Carboxylic acid-4.
$^1$H-NMR (300 MHz, DMSO-d$_6$) delta 11.16 (1H, s), 2.48 (3H, s), 2.18-2.09 (1H, m), 0.86-0.82 (4H, m), MS (ESI) m/z: 222 (M+H)⁺.

Carboxylic acid-7: 2-(cyclopropanecarboxamido)pyrimidine-4-carboxylic acid

<Step-1>: methyl 2-(cyclopropanecarboxamido)pyrimidine-4-carboxylate

The title compound is prepared in quantitative yield (1.93 g, a pale yellow solid) from methyl 2-chloropyrimidine-4-carboxylate (1.50 g, 8.69 mmol) and cyclopropanecarboxamide by the similar manner in Step-1 of Carboxylic acid-4.
$^1$H-NMR (300 MHz, CDCl$_3$) delta 8.86 (1H, d, J=5.1 Hz), 8.38 (1H, br.s), 7.67 (1H, d, J=5.1 Hz), 4.03 (3H, s), 2.20-2.08 (1H, m), 1.23-1.18 (2H, m), 0.99-0.93 (2H, m), MS (ESI) m/z: 222 (M+H)⁺.

<Step-2>: 2-(cyclopropanecarboxamido)pyrimidine-4-carboxylic acid

The title compound is prepared in 66% yield (1.19 g, an off-white solid) from methyl 2-(cyclopropanecarboxamido)pyrimidine-4-carboxylate (1.93 g, 8.72 mmol, Step-1) by the similar manner in Step-2 of Carboxylic acid-4.
$^1$H-NMR (300 MHz, DMSO-d$_6$) delta 11.20 (1H, s), 8.89 (1H, d, J=4.4 Hz), 7.63 (1H, d, J=4.4 Hz), 2.20-2.10 (1H, m), 0.83 (4H, d, J=6.6 Hz), MS (ESI) m/z: 206 (M−H)⁻.

Carboxylic acid-8: 2-butyramidoisonicotinic acid

<Step-1>: methyl 2-butyramidoisonicotinate

The title compound is prepared in 82% yield (1.94 g, a white solid) from methyl 2-aminoisonicotinate hydrochloride (2.00 g, 10.6 mmol) and butyryl chloride by the similar manner in Step-1 of Carboxylic acid-1.
$^1$H-NMR (300 MHz, CDCl$_3$) delta 8.76 (1H, s), 8.39 (1H, d, J=5.1 Hz), 8.08 (1H, br.s), 7.60 (1H, dd, J=5.1, 1.5 Hz), 3.95 (3H, s), 2.41 (2H, t, J=7.3 Hz), 1.80 (2H, sextet, J=7.3 Hz), 1.02 (3H, t, J=7.3 Hz), MS (ESI) m/z: 223 (M+H)⁺.

<Step-2>: 2-butyramidoisonicotinic acid

The title compound is prepared in 76% yield (1.28 g, a white solid) from methyl 2-butyramidoisonicotinate (1.94 g, 8.71 mmol, Step-1) by the similar manner in Step-2 of Carboxylic acid-1.
$^1$H-NMR (300 MHz, DMSO-d$_6$) delta 10.66 (1H, s), 8.58 (1H, s), 8.45 (1H, d, J=5.1 Hz), 7.48 (1H, dd, J=5.1, 1.5 Hz), 2.37 (2H, t, J=7.3 Hz), 1.59 (2H, sextet, J=7.3 Hz), 0.89 (3H, t, J=7.3 Hz), MS (ESI) m/z: 209 (M+H)⁺, 207 (M−H)⁻.

Carboxylic acid-9: 2-pivalamidoisonicotinic acid

<Step-1>: methyl 2-pivalamidoisonicotinate

The title compound is prepared in quantitative yield (1.25 g, colorless syrup) from methyl 2-aminoisonicotinate hydrochloride (1.00 g, 5.30 mmol) and pivaloyl chloride by the similar manner in Step-1 of Carboxylic acid-1.
$^1$H-NMR (270 MHz, CDCl$_3$) delta 8.81 (1H, s), 8.39 (1H, d, J=5.3 Hz), 8.24 (1H, br.s), 7.61 (1H, dd, J=5.3, 1.3 Hz), 3.94 (3H, s), 1.35 (9H, s).

<Step-2>: 2-pivalamidoisonicotinic acid

The title compound is prepared in 61% yield (0.72 g, a white solid) from methyl 2-pivalamidoisonicotinate (1.25 g, 5.30 mmol, Step-1) by the similar manner in Step-2 of Carboxylic acid-1.
$^1$H-NMR (270 MHz, DMSO-d$_6$) delta 10.07 (1H, s), 8.55 (1H, s), 8.49 (1H, d, J=5.3 Hz), 7.53 (1H, d, J=5.3 Hz), 1.25 (9H, s), MS (ESI) m/z: 223 (M+H)⁺.

Carboxylic acid-10: 2-methyl-6-propionamidoisonicotinic acid

<Step-1>: methyl 2-methyl-6-propionamidoisonicotinate

The title compound is prepared in 60% yield (2.16 g, a pale yellow solid) from methyl 2-chloro-6-methylisonicotinate (3.00 g, 16.2 mmol) and propionamide by the similar manner in Step-1 of Carboxylic acid-4.
$^1$H-NMR (300 MHz, CDCl$_3$) delta 8.55 (1H, s), 7.93 (1H, br.s), 7.47 (1H, s), 3.93 (3H, s), 2,51 (3H, s), 2.44 (2H, q, J=7.3 Hz), 1.26 (3H, t, J=7.3 Hz), MS (ESI) m/z: 223 (M+H)⁺.

<Step-2>: 2-methyl-6-propionamidoisonicotinic acid

The title compound is prepared in 96% yield (1.95 g, a white solid) from methyl 2-methyl-6-propionamidoisonicotinate (2.16 g, 9.72 mmol, Step-1) by the similar manner in Step-2 of Carboxylic acid-1.
$^1$H-NMR (300 MHz, DMSO-d$_6$) delta 10.60 (1H, s), 8.40 (1H, s), 7.38 (1H, s), 2.47 (3H, s), 2.40 (2H, q, J=7.3 Hz), 1.06 (3H, t, J=7.3 Hz), MS (ESI) m/z: 209 (M+H)⁺.

Carboxylic acid-11: 2-(cyclopropanecarboxamido)-6-methylisonicotinic acid

<Step-1>: methyl 2-(cyclopropanecarboxamido)-6-methylisonicotinate

The title compound is prepared in 66% yield (1.3 g, a pale yellow solid) from methyl 2-chloro-6-methylisonicotinate (1.5 g, 8.1 mmol) and cyclopropanecarboxamide by the similar manner in Step-1 of Carboxylic acid-4.
$^1$H-NMR (300 MHz, CDCl$_3$) delta 8.52 (1H, s), 8.17 (1H, br.s), 7.46 (1H, s), 3.92 (3H, s), 2.52 (3H, s), 1.60-1.50 (1H, m), 1.15-1.10 (2H, m), 0.93-0.88 (2H, m), MS (ESI) m/z: 235 (M+H)⁺, 233 (M−H)⁻.

\<Step-2\>:
2-(cyclopropanecarboxamido)-6-methylisonicotinic acid

The title compound is prepared in 89% yield (1.1 g, a white solid) from methyl 2-(cyclopropanecarboxamido)-6-methylisonicotinate (1.3 g, 5.3 mmol, Step-1) by the similar manner in Step-2 of Carboxylic acid-1.

$^1$H-NMR (300 MHz, DMSO-d$_6$) delta 10.96 (1H, s), 8.38 (1H, s), 7.37 (1H, s), 2.48 (3H, s), 2.04-1.90 (1H, m), 0.83-0.70 (4H, m), MS (ESI) m/z: 221 (M+H)$^+$, 219 (M−H)$^-$.

Carboxylic acid-12:
2-acetamido-6-methylpyrimidine-4-carboxylic acid

\<Step-1\>: methyl 2-acetamido-6-methylpyrimidine-4-carboxylate

The title compound is prepared in 68% yield (0.76 g, a yellow solid) from methyl 2-chloro-6-methylpyrimidine-4-carboxylate (1.0 g, 5.4 mmol) and acetamide by the similar manner in Step-1 of Carboxylic acid-4.

$^1$H-NMR (300 MHz, CDCl$_3$) delta 8.01 (1H, br.s), 7.54 (1H, s), 4.00 (3H, s), 2.59 (3H, s), 2.53 (3H, s), MS (ESI) m/z: 210 (M+H)$^+$.

\<Step-2\>:
2-acetamido-6-methylpyrimidine-4-carboxylic acid

The title compound is prepared in 30% yield (0.21 g, a yellow solid) from methyl 2-acetamido-6-methylpyrimidine-4-carboxylate (1.3 g, 5.3 mmol, Step-1) by the similar manner in Step-2 of Carboxylic acid-4.

$^1$H-NMR (300 MHz, DMSO-d$_6$) delta 10.76 (1H, s), 7.55 (1H, s), 2.49 (3H, s), 2.20 (3H, s), MS (ESI) m/z: 196 (M+H)$^+$.

Carboxylic acid-13:
6-methyl-2-propionamidopyrimidine-4-carboxylic acid

\<Step-1\>: methyl 6-methyl-2-propionamidopyrimidine-4-carboxylate

The title compound is prepared in 61% yield (0.73 g, a yellow solid) from methyl 2-chloro-6-methylpyrimidine-4-carboxylate (1.0 g, 5.4 mmol) and propionamide by the similar manner in Step-1 of Carboxylic acid-4.

$^1$H-NMR (300 MHz, CDCl$_3$) delta 8.05 (1H, br.s), 7.54 (1H, s), 4.00 (3H, s), 2.77 (2H, q, J=7.3 Hz), 2.59 (3H, s), 1.24 (3H, t, J=7.3 Hz), MS (ESI) m/z: 224 (M+H)$^+$.

\<Step-2\>:
6-methyl-2-propionamidopyrimidine-4-carboxylic acid

The title compound is prepared in 19% yield (0.13 g, a yellow solid) from methyl 6-methyl-2-propionamidopyrimidine-4-carboxylate (0.73 g, 3.3 mmol, Step-1) by the similar manner in Step-2 of Carboxylic acid-4.

$^1$H-NMR (300 MHz, CDCl$_3$) delta 8.10 (1H, br.s), 7.68 (1H, s), 2.66 (2H, q, J=7.3 Hz), 2.60 (3H, s), 1.26 (3H, t, J=7.3 Hz), MS (ESI) m/z: 210 (M+H)$^+$.

Carboxylic acid-14:
2-isobutyramido-6-methylpyrimidine-4-carboxylic acid

\<Step-1\>: methyl 2-isobutyramido-6-methylpyrimidine-4-carboxylate

The title compound is prepared in 88% yield (1.1 g, a yellow solid) from methyl 2-chloro-6-methylpyrimidine-4-carboxylate (1.0 g, 5.4 mmol) and isobutyramide by the similar manner in Step-1 of Carboxylic acid-4.

$^1$H-NMR (300 MHz, CDCl$_3$) delta 8.22 (1H, br.s), 7.56 (1H, s), 4.01 (3H, s), 2.90 (1H, sep, J=7.3 Hz), 2.61 (3H, s), 1.26 (6H, d, J=7.3 Hz), MS (ESI) m/z: 238 (M+H)$^+$, 236 (M−H)$^-$.

\<Step-2\>:
2-isobutyramido-6-methylpyrimidine-4-carboxylic acid

The title compound is prepared in 46% yield (0.49 g, a yellow solid) from methyl 2-isobutyramido-6-methylpyrimidine-4-carboxylate (1.1 g, 4.7 mmol, Step-1) by the similar manner in Step-2 of Carboxylic acid-4.

$^1$H-NMR (270 MHz, DMSO-d$_6$) delta 10.89 (1H, br.s), 7.55 (1H, s), 2.84 (1H, septet, J=7.3 Hz), 2.47 (3H, s), 1.10 (6H, d, J=7.3 Hz), MS (ESI) m/z: 224 (M+H)$^+$.

Carboxylic acid-15: 2-(2-hydroxy-2-methylpropanamido)-6-methylisonicotinic acid

\<Step-1\>: methyl 2-(2-acetoxy-2-methylpropanamido)-6-methylisonicotinate

The title compound is prepared in 80% yield (0.89 g, a yellow solid) from methyl 2-chloro-6-methylisonicotinate (0.70 g, 3.8 mmol) and 1-amino-2-methyl-1-oxopropan-2-yl acetate by the similar manner in Step-1 of Carboxylic acid-4.

$^1$H-NMR (300 MHz, CDCl$_3$) delta 8.58 (1H, s), 8.34 (1H, br.s), 7.50 (1H, s), 3.93 (3H s), 2.52 (3H, s), 2.16 (3H, s), 1.73 (6H, s), MS (ESI) m/z: 295 (M+H)$^+$.

\<Step-2\>: 2-(2-hydroxy-2-methylpropanamido)-6-methylisonicotinic acid

The title compound is prepared in 80% yield (0.54 g, a white solid) from methyl 2-(2-acetoxy-2-methylpropanamido)-6-methylisonicotinate (0.83 g, 2.8 mmol, Step-1) by the similar manner in Step-2 of Carboxylic acid-4.

$^1$H-NMR (300 MHz, DMSO-d$_6$) delta 9.50 (1H, br.s), 8.39 (1H, s), 7.45 (1H, s), 6.07 (1H, br.s), 2.48 (3H, s), 1.37 (6H, s), MS (ESI) m/z: 239 (M+H)$^+$.

EXAMPLE SYNTHESIS PART

Example 1

2-(cyclopropanecarboxamido)-N-(2-(4-(trifluoromethyl)phenoxy)propyl)isonicotinami de To a mixture of 2-(4-(trifluoromethyl)phenoxy)propan-1-amine (15 mg, 0.068 mmol, Amine-1), 2-(cyclopropanecarboxamido)isonicotinic acid (14 mg, 0.068 mmol, Carboxylic acid-2) and N,N-diisopropylethylamine (0.047 mL, 0.27 mmol) in DMF (1 mL) is added HBTU (39 mg, 0.10 mmol) at rt. After stifling at 60° C. for 2 hours, the mixture is diluted with EtOAc (6 mL), washed with water, and dried over sodium sulfate. The organic layer is purified by column chromatography on NH-silica gel eluting with EtOAc and then by preparative LC-MS to give 8.6 mg of the title compound.

Other examples are prepared according to the procedure similar to that described in Example 1, using the appropriate amine and the carboxylic acid (see Table 2). The reactants are commercially available materials or obtained by conventional methods known to those skilled in the art, otherwise noted in the intermediate synthesis part.

The observed MS (positive or negative mode) and retention time by LC-MS of all examples are described in Table 3. Each chemical structure of Amine part for synthesis of Example is described as a free-base in Table 2. $^1$H-NMR of Examples 2, 7, 13, 15, 22, 35, 42, 53, 68 and 96 are described in Table 4.

TABLE 2-1

| Example | Reactant | Reactant |
|---|---|---|
| 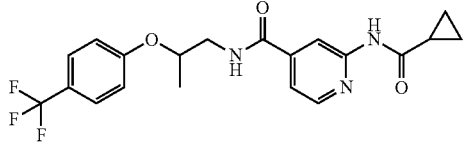<br>Example 1<br>2-(cyclopropanecarboxamido)-N-(2-(4-(trifluoromethyl)phenoxy)propyl)isonicotinamide | 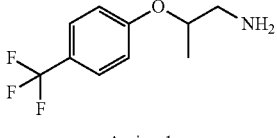<br>Amine-1 | 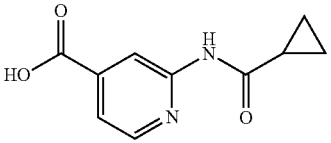<br>Carboxylic acid-2 |
| 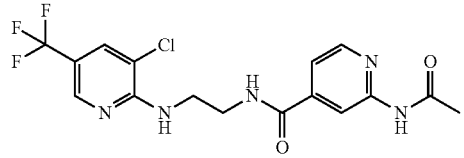<br>Example 2<br>2-acetamido-N-(2-((3-chloro-5-(trifluoromethyl)pyridin-2-yl)amino)ethyl)isonicotinamide | 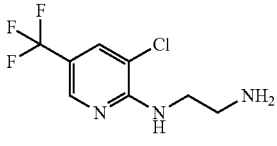<br>Amine-2 | 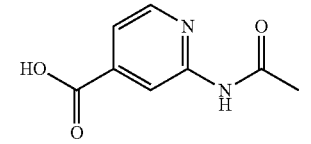<br>Carboxylic acid-16 |
| 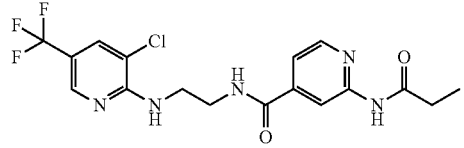<br>Example 3<br>N-(2-((3-chloro-5-(trifluoromethyl)pyridin-2-yl)amino)ethyl)-2-propionamidoisonicotinamide | 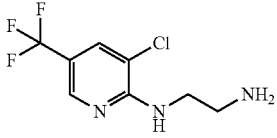<br>Amine-2 | 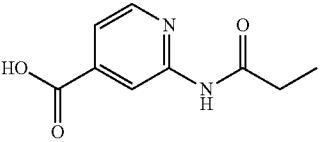<br>Carboxylic acid-1 |
| 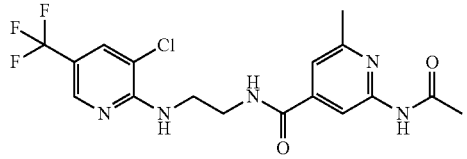<br>Example 4<br>2-acetamido-N-(2-((3-chloro-5-(trifluoromethyl)pyridin-2-yl)amino)ethyl)-6-methylisonicotinamide | 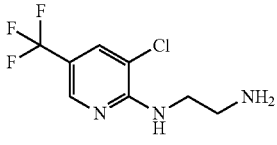<br>Amine-2 | 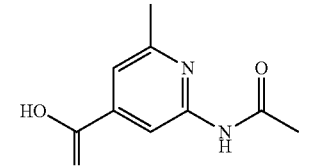<br>Carboxylic acid-4 |
| 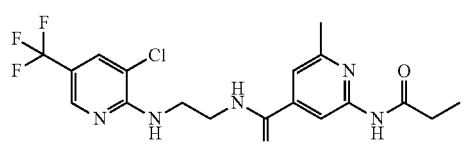<br>Example 5<br>N-(2-((3-chloro-5-(trifluoromethyl)pyridin-2-yl)amino)ethyl)-2-methyl-6-propionamidoisonicotinamide | 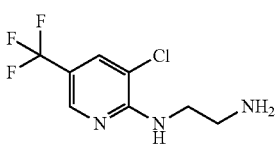<br>Amine-2 | 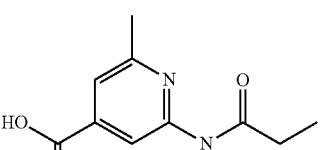<br>Carboxylic acid-10 |

TABLE 2-1-continued

| Example | Reactant | Reactant |
|---|---|---|
| 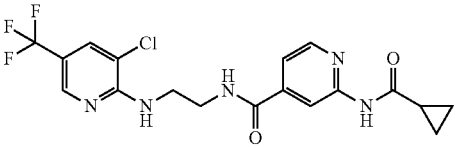<br>Example 6<br>N-(2-((3-chloro-5-(trifluoromethyl)pyridin-2-yl)amino)ethyl)-2-(cyclopropanecarboxamido)isonicotinamide | 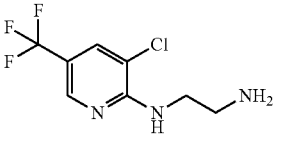<br>Amine-2 | 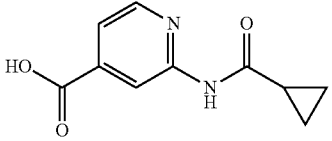<br>Carboxylic acid-2 |
| 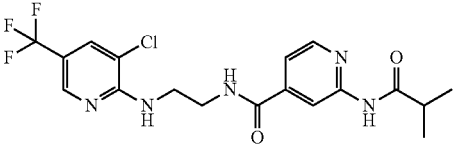<br>Example 7<br>N-(2-((3-chloro-5-(trifluoromethyl)pyridin-2-yl)amino)ethyl)-2-isobutyramidoisonicotinamide | 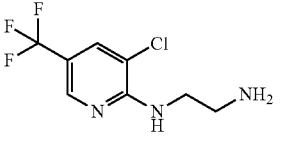<br>Amine-2 | 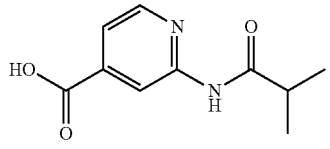<br>Carboxylic acid-3 |
| 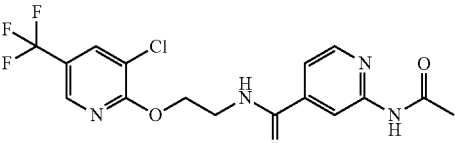<br>Example 8<br>2-acetamido-N-(2-((3-chloro-5-(trifluoromethyl)pyridin-2-yl)oxy)ethyl)isonicotinamide | 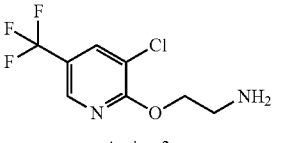<br>Amine-3 | 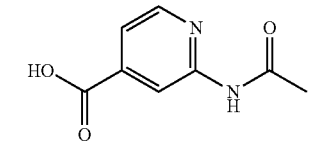<br>Carboxylic acid-16 |
| 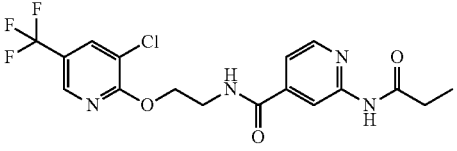<br>Example 9<br>N-(2-((3-chloro-5-(trifluoromethyl)pyridin-2-yl)oxy)ethyl)-2-propionamidoisonicotinamide | 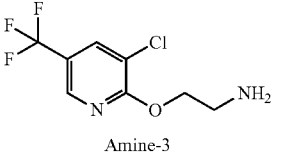<br>Amine-3 | 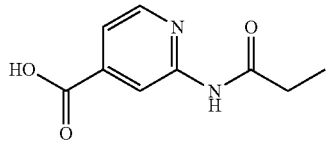<br>Carboxylic acid-1 |
| 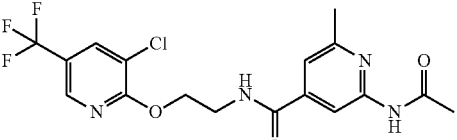<br>Example 10<br>2-acetamido-N-(2-((3-chloro-5-(trifluoromethyl)pyridin-2-yl)oxy)ethyl)-6-methylisonicotinamide | 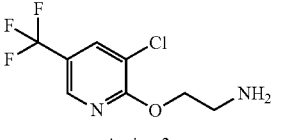<br>Amine-3 | 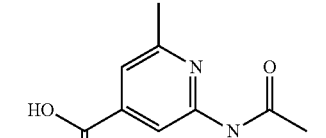<br>Carboxylic acid-4 |
| 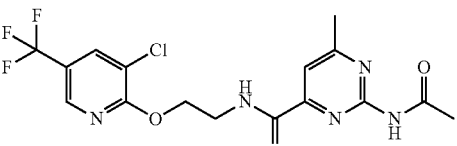<br>Example 11<br>2-acetamido-N-(2-((3-chloro-5-(trifluoromethyl)pyridin-2-yl)oxy)ethyl)-6-methylpyrimidine-4-carboxamide | 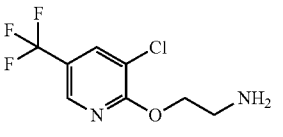<br>Amine-3 | 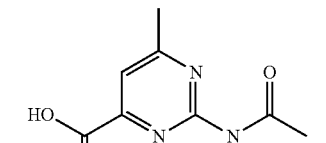<br>Carboxylic acid-12 |

TABLE 2-1-continued

| Example | Reactant | Reactant |
|---|---|---|
| 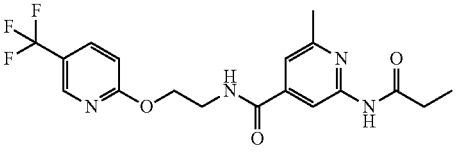<br>Example 12<br>2-methyl-6-propionamido-N-(2-((5-(trifluoromethyl)pyridin-2-yl)oxy)ethyl)isonicotinamide | 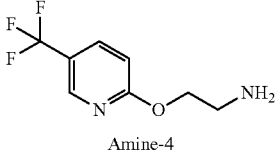<br>Amine-4 | 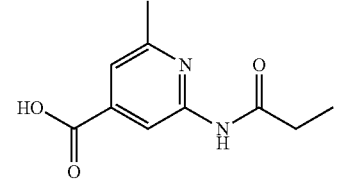<br>Carboxylic acid-10 |
| 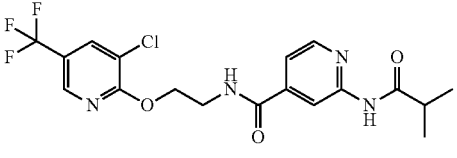<br>Example 13<br>N-(2-((3-chloro-5-(trifluoromethyl)pyridin-2-yl)oxy)ethyl)-2-isobutyramidoisonicotinamide | 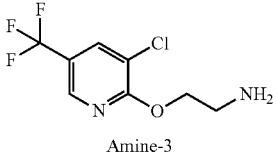<br>Amine-3 | 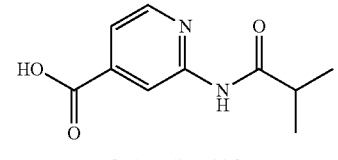<br>Carboxylic acid-3 |
| 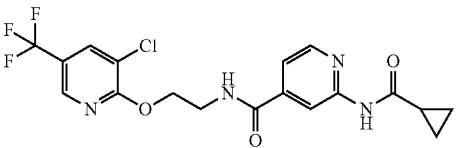<br>Example 14<br>N-(2-((3-chloro-5-(trifluoromethyl)pyridin-2-yl)oxy)ethyl)-2-(cyclopropanecarboxamido)isonicotinamide | 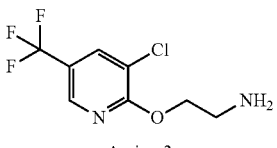<br>Amine-3 | <br>Carboxylic acid-2 |
| 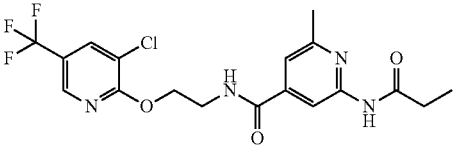<br>Example 15<br>N-(2-((3-chloro-5-(trifluoromethyl)pyridin-2-yl)oxy)ethyl)-2-methyl-6-propionamidoisonicotinamide | 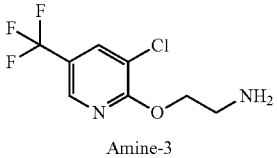<br>Amine-3 | 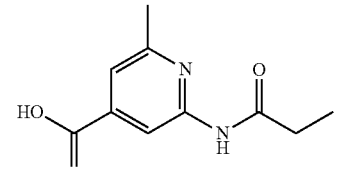<br>Carboxylic acid-10 |
| 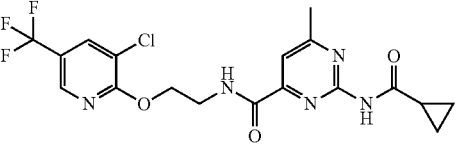<br>Example 16<br>N-(2-((3-chloro-5-(trifluoromethyl)pyridin-2-yl)oxy)ethyl)-2-(cyclopropanecarboxamido)-6-methylpyrimidine-4-carboxamide | 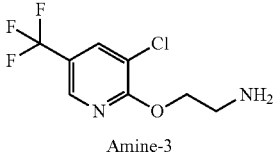<br>Amine-3 | 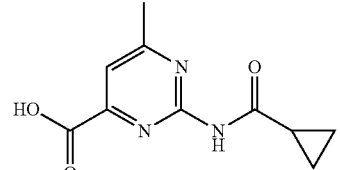<br>Carboxylic acid-6 |
| 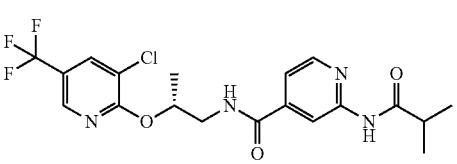<br>Example 17<br>(R)-N-(2-((3-chloro-5-(trifluoromethyl)pyridin-2-yl)oxy)propyl)-2-isobutyramidoisonicotinamide | 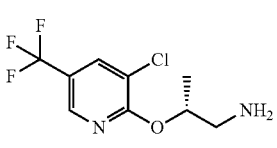<br>Amine-5 | 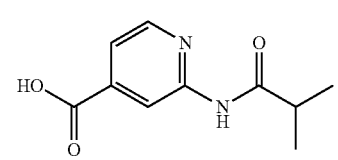<br>Carboxylic acid-3 |

TABLE 2-1-continued

| Example | Reactant | Reactant |
|---|---|---|
| 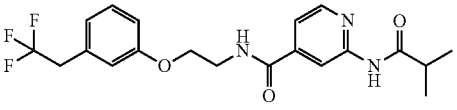 Example 18<br>2-isobutyramido-N-(2-(3-(trifluoromethoxy)phenoxy)ethyl)isonicotinamide | 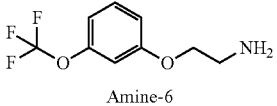 Amine-6 | 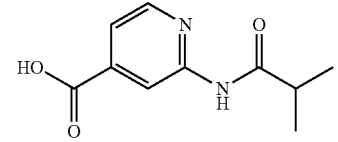 Carboxylic acid-3 |
| 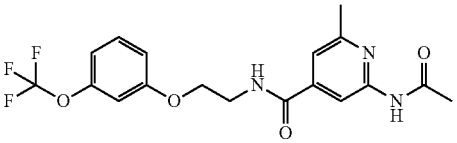 Example 19<br>2-acetamido-6-methyl-N-(2-(3-(trifluoromethoxy)phenoxy)ethyl)isonicotinamide | 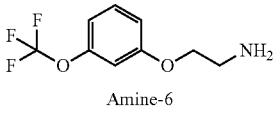 [SMILES: NCCOc1cccc(OC(F)(F)F)c1] Amine-6 | 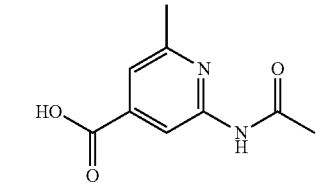 Carboxylic acid-3 |
| 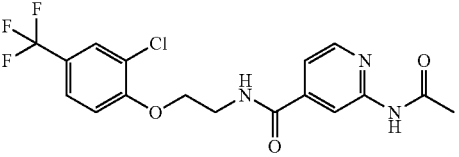 Example 20<br>2-acetamido-N-(2-(2-chloro-4-(trifluoromethyl)phenoxy)ethyl)isonicotinamide | 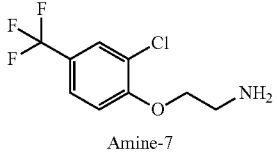 [SMILES: NCCOc1ccc(C(F)(F)F)cc1Cl] Amine-7 | 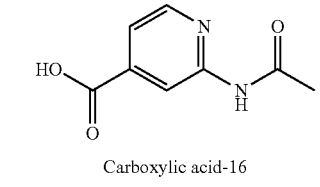 Carboxylic acid-16 |
| 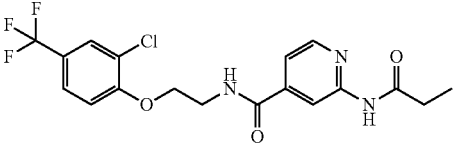 Example 21<br>N-(2-(2-chloro-4-(trifluoromethyl)phenoxy)ethyl)-2-propionamidoisonicotinamide | 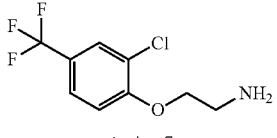 Amine-7 | 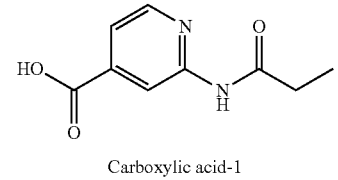 Carboxylic acid-1 |
| 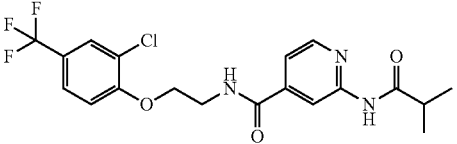 Example 22<br>N-(2-(2-chloro-4-(trifluoromethyl)phenoxy)ethyl)-2-isobutyramidoisonicotinamide | 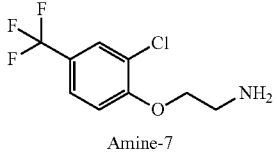 [SMILES: NCCOc1ccc(C(F)(F)F)cc1Cl] Amine-7 | 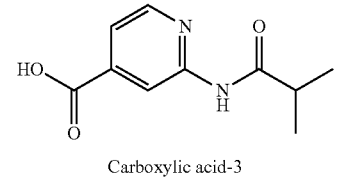 Carboxylic acid-3 |
| 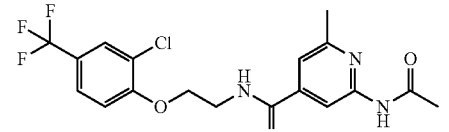 Example 23<br>2-acetamido-N-(2-(2-chloro-4-trifluoromethyl)phenoxy)ethyl)-6-methylisonicotinamide | 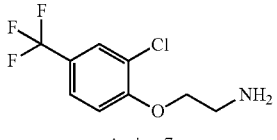 Amine-7 | 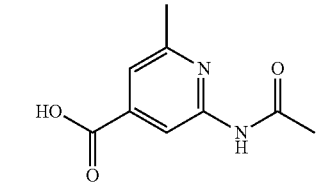 Carboxylic acid-4 |

TABLE 2-1-continued

| Example | Reactant | Reactant |
|---|---|---|
| 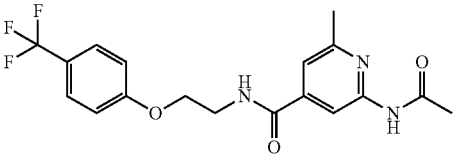<br>Example 24<br>2-acetamido-6-methyl-N-(2-(4-(trifluoromethyl)phenoxy)ethyl)isonicotinamide | 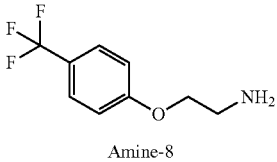<br>Amine-8 | 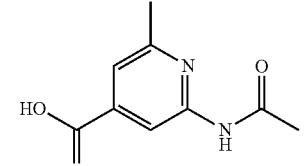<br>Carboxylic acid-4 |
| 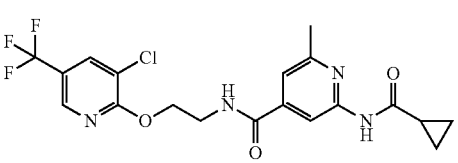<br>Example 25<br>N-(2-((3-chloro-5-(trifluoromethyl)pyridin-2-yl)oxy)ethyl)-2-(cyclopropanecarboxamido)-6-methylisonicotinamide | 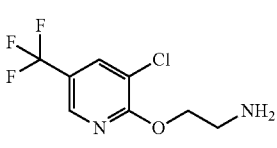<br>Amine-3 | 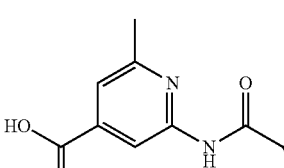<br>Carboxylic acid-11 |
| 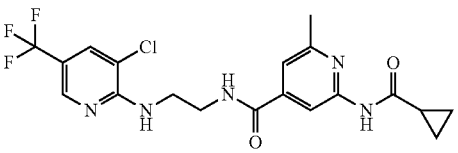<br>Example 26<br>N-(2-((3-chloro-5-(trifluoromethyl)pyridin-2-yl)amino)ethyl)-2-(cyclopropanecarboxamido)-6-methylisonicotinamide | 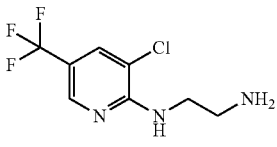<br>Amine-2 | 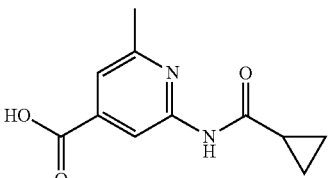<br>Carboxylic acid-11 |
| 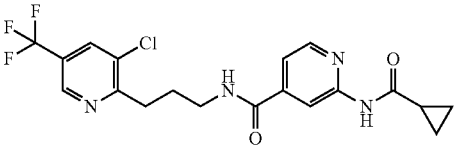<br>Example 27<br>N-(3-(3-chloro-5-(trifluoromethyl)pyridin-2-yl)propyl)-2-(cyclopropanecarboxamido)isonicotinamide | 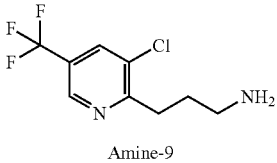<br>Amine-9 | 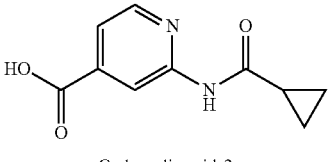<br>Carboxylic acid-2 |
| 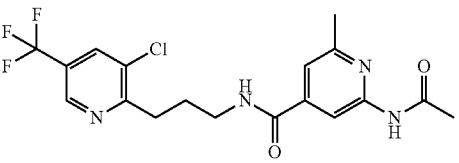<br>Example 28<br>2-acetamido-N-(3-(3-chloro-5-(trifluoromethyl)pyridin-2-yl)propyl)-6-methylisonicotinamide | 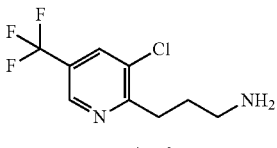<br>Amine-9 | 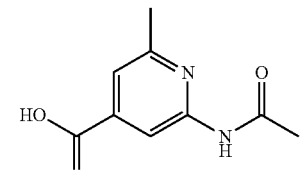<br>Carboxylic acid-4 |
| 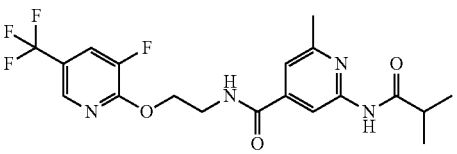<br>Example 29<br>N-(2-((3-fluoro-5-(trifluoromethyl)pyridin-2-yl)oxy)ethyl)-2-isobutyramido-6-methylisonicotinamide | 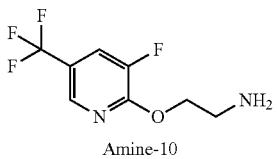 [SMILES: NCCOc1ncc(C(F)(F)F)cc1F]<br>Amine-10 | 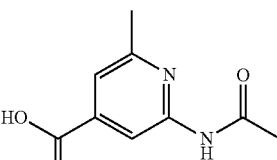<br>Carboxylic acid-5 |

TABLE 2-1-continued

| Example | Reactant | Reactant |
|---|---|---|
| 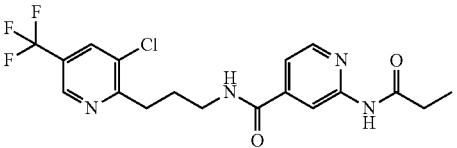<br>Example 30<br>N-(3-(3-chloro-5-(trifluoromethyl)pyridin-2-yl)propyl)-2-propionamidoisonicotinamide | 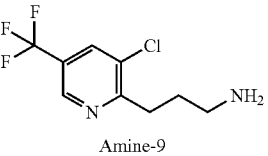 [SMILES: NCCCc1ncc(C(F)(F)F)cc1Cl]<br>Amine-9 | <br>Carboxylic acid-1 |
| 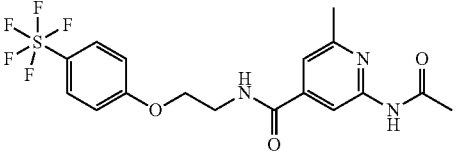<br>Example 31<br>2-acetamido-6-methyl-N-(2-(4-(pentafluorosulfanyl)phenoxy)ethyl)isonicotinamide | 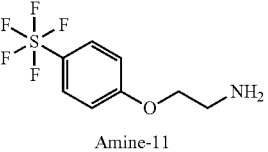 [SMILES: NCCOc1ccc(S(F)(F)(F)(F)F)cc1]<br>Amine-11 | 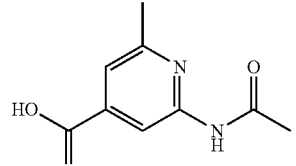<br>Carboxylic acid-4 |
| 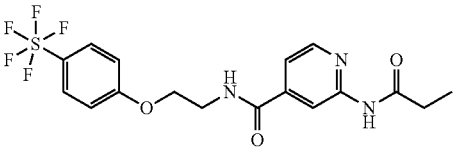<br>Example 32<br>2-propionamido-N-(2-(4-(pentafluorosulfanyl)phenoxy)ethyl)isonicotinamide | 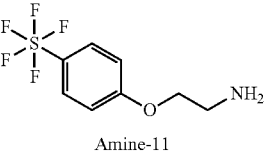<br>Amine-11 | <br>Carboxylic acid-1 |
| 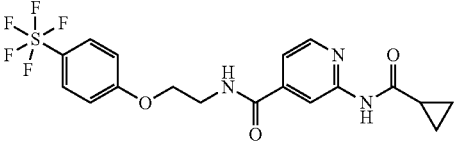<br>Example 33<br>2-(cyclopropanecarboxamido)-N-(2-(4-(pentafluorosulfanyl)phenoxy)ethyl)isonicotinamide | 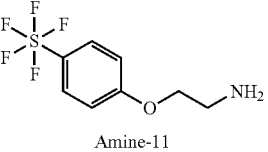 [SMILES: NCCOc1ccc(S(F)(F)(F)(F)F)cc1]<br>Amine-11 | <br>Carboxylic acid-2 |
| 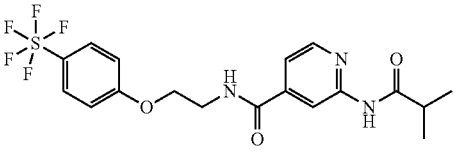<br>Example 34<br>2-isobutyramido-N-(2-(4-(pentafluorosulfanyl)phenoxy)ethyl)isonicotinamide | 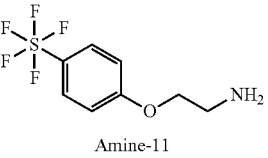 [SMILES: NCCOc1ccc(S(F)(F)(F)(F)F)cc1]<br>Amine-11 | 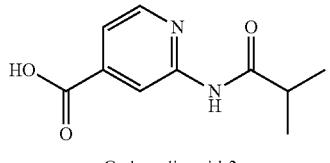<br>Carboxylic acid-3 |
| 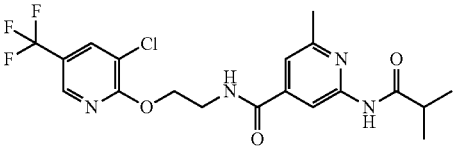<br>Example 35<br>N-(2-((3-chloro-5-(trifluoromethyl)pyridin-2-yl)oxy)ethyl)-2-isobutyramido-6-methylisonicotinamide | 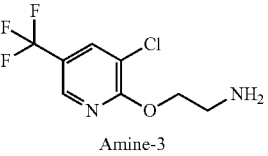 [SMILES: NCCOc1ncc(C(F)(F)F)cc1Cl]<br>Amine-3 | 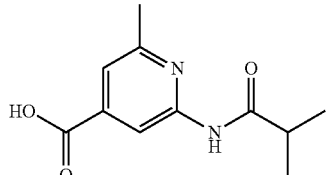<br>Carboxylic acid-5 |

TABLE 2-1-continued

| Example | Reactant | Reactant |
|---|---|---|
| 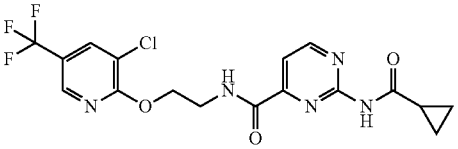<br>Example 36<br>N-(2-((3-chloro-5-(trifluoromethyl)pyridin-2-yl)oxy)ethyl)-2-(cyclopropanecarboxamido)pyrimidine-4-Carboxamide | 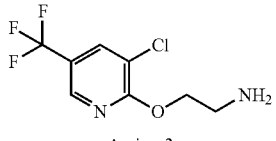<br>Amine-3 | 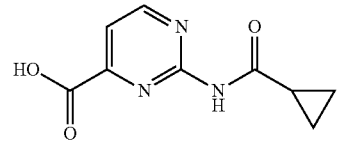<br>Carboxylic acid-7 |
| 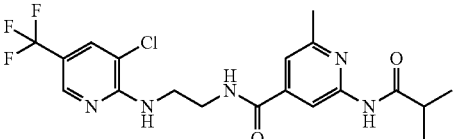<br>Example 37<br>N-(2-((3-chloro-5-(trifluoromethyl)pyridin-2-yl)amino)ethyl)-2-isobutyramido-6-methylisonicotinamide | 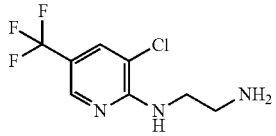<br>Amine-2 | 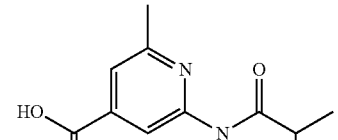<br>Carboxylic acid-5 |
| 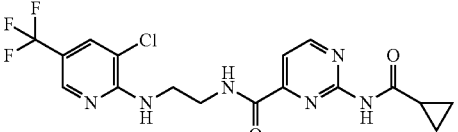<br>Example 38<br>N-(2-((3-chloro-5-(trifluoromethyl)pyridin-2-yl)amino)ethyl)-2-(cyclopropanecarboxamido)pyrimidlne-4-carboxamide | 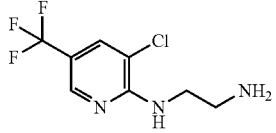<br>Amine-2 | 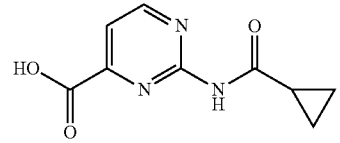<br>Carboxylic acid-7 |
| 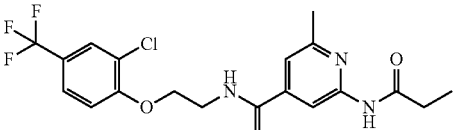<br>Example 39<br>N-(2-(2-chloro-4-(trifluoromethyl)phenoxy)ethyl)-2-methyl-6-propionamidoisonicotinamide | 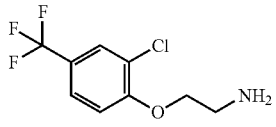<br>Amine-7 | 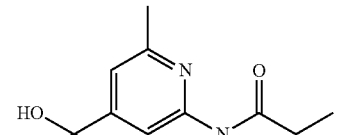<br>Carboxylic acid-10 |
| 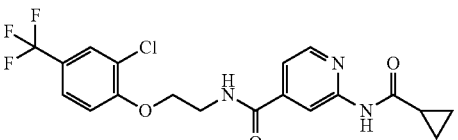<br>Example 40<br>N-(2-(2-chloro-4-(trifluoromethyl)phenoxy)ethyl)-2-(cyclopropanecarboxamido)isonicotinamide | 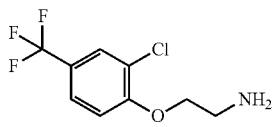<br>Amine-7 | 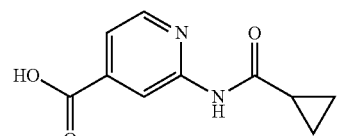<br>Carboxylic acid-2 |
| 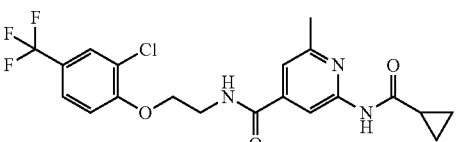<br>Example 41<br>N-(2-(2-chloro-4-(trifluoromethyl)phenoxy)ethyl)-2-(cyclopropanecarboxamido)-6-methylisonicotinamide | 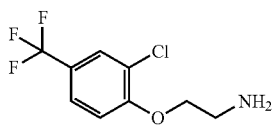<br>Amine-7 | 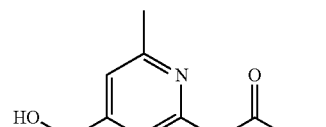<br>Carboxylic acid-11 |

TABLE 2-1-continued

| Example | Reactant | Reactant |
|---|---|---|
| 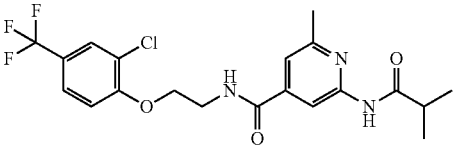<br>Example 42<br>N-(2-(2-chloro-4-(trifluoromethyl)phenoxy)ethyl)-<br>2-isobutyramido-6-methylisonicotinamide | 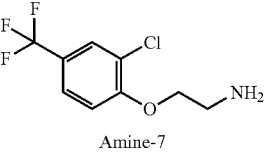 [SMILES: NCCOc1ccc(C(F)(F)F)cc1Cl]<br>Amine-7 | 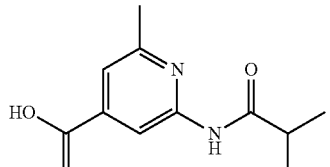<br>Carboxylic acid-5 |
| 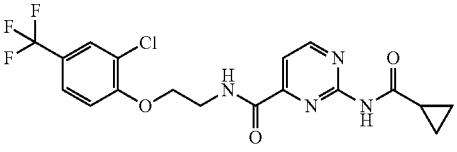<br>Example 43<br>N-(2-(2-chloro-4-(trifluoromethyl)phenoxy)ethyl)-<br>2-(cyclopropanecarboxamido)pyrimidine-4-carboxamide | 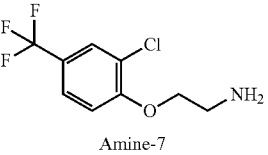 [SMILES: NCCOc1ccc(C(F)(F)F)cc1Cl]<br>Amine-7 | 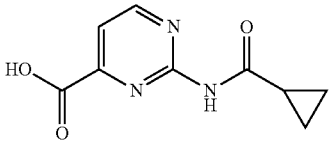<br>Carboxylic acid-7 |
| 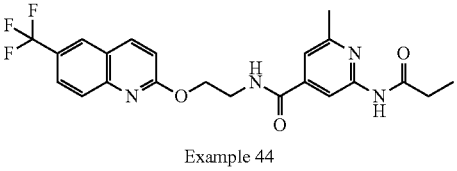<br>Example 44<br>2-methyl-6-propionamido-N-(2-((6-(trifluoromethyl)<br>quinolin-2-yl)oxy)ethyl)isonicotinamide | 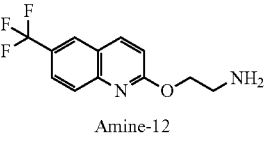 [SMILES: NCCOc1ccc2cc(C(F)(F)F)ccc2n1]<br>Amine-12 | 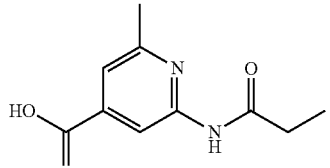<br>Carboxylic acid-10 |
| 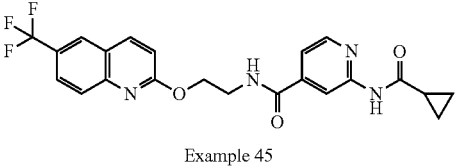<br>Example 45<br>2-(cyclopropanecarboxamido)-N-(2-((6-(trifluoromethyl)<br>quinolin-2-yl)oxy)ethyl)isonicotinamide | 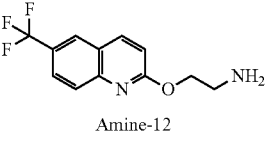 [SMILES: NCCOc1ccc2cc(C(F)(F)F)ccc2n1]<br>Amine-12 | 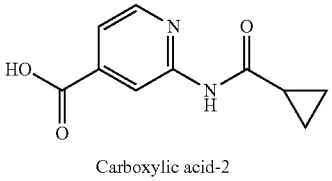 [SMILES: O=C(O)c1ccnc(NC(=O)C2CC2)c1]<br>Carboxylic acid-2 |
| 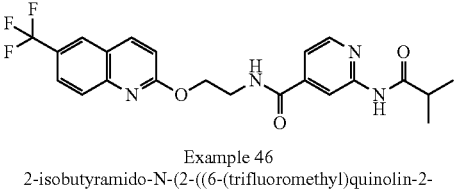<br>Example 46<br>2-isobutyramido-N-(2-((6-(trifluoromethyl)quinolin-2-<br>yl)oxy)ethyl)isonicotinamide | 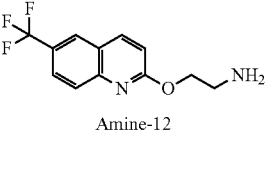 [SMILES: NCCOc1ccc2cc(C(F)(F)F)ccc2n1]<br>Amine-12 | 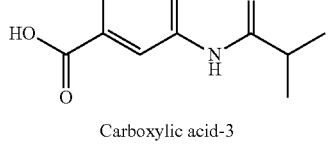<br>Carboxylic acid-3 |
| 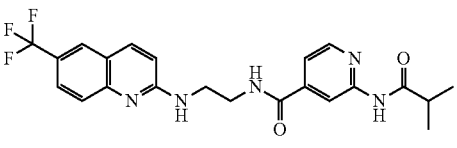<br>Example 47<br>2-isobutyramido-N-(2-((6-(trifluoromethyl)quinolin-2-<br>yl)amino)ethyl)isonicotinamide | 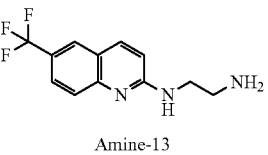 [SMILES: NCCNc1ccc2cc(C(F)(F)F)ccc2n1]<br>Amine-13 | 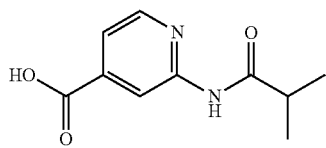<br>Carboxylic acid-3 |

TABLE 2-1-continued

| Example | Reactant | Reactant |
|---|---|---|
| 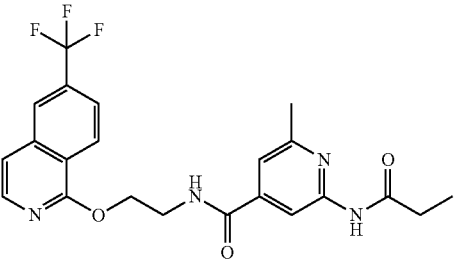<br>Example 48<br>2-methyl-6-propionamido-N-(2-((6-(trifluoromethyl)isoquinolin-1-yl)oxy)ethyl)isonicotinamida | 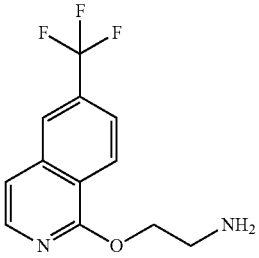<br>Amine-14 | 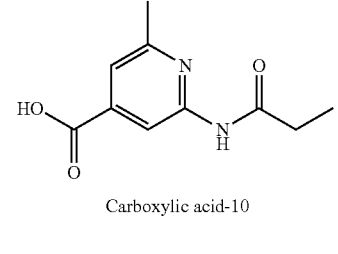<br>Carboxylic acid-10 |
| 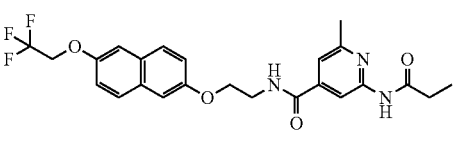<br>Example 49<br>2-methyl-6-propionamido-N-(2-((6-(2,2,2-trifluoroethoxy)naphthalen-2-yl)oxy)ethyl)isonicotinamide | 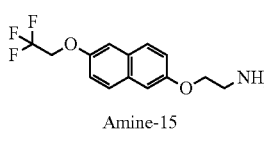<br>Amine-15 | 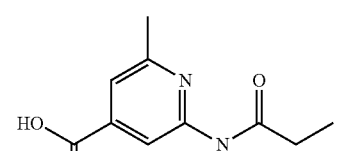<br>Carboxylic acid-10 |
| 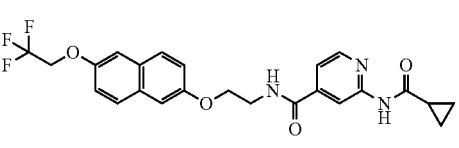<br>Example 50<br>2-(cyclopropanecarboxamido)-N-(2-((6-(2,2,2-trifluoroethoxy)naphthalen-2-yl)oxy)ethyl)isonicotinamide | 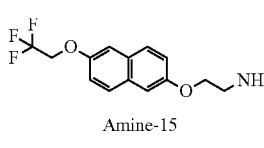<br>Amine-15 | 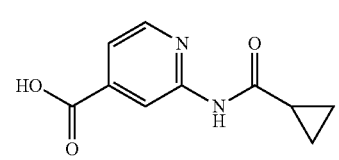<br>Carboxylic acid-2 |
| 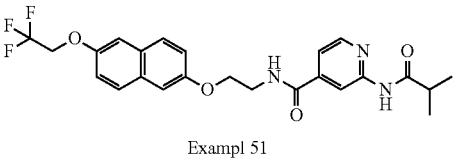<br>Exampl 51<br>2-isobutyramido-N-(2-((6-(2,2,2-trifluoroethoxy)naphthalen-2-yl)oxy)ethyl)isonicotinamide | 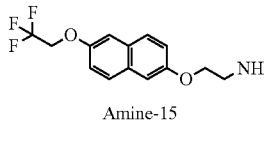<br>Amine-15 | 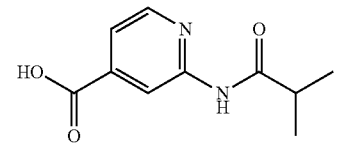<br>Carboxylic acid-3 |
| 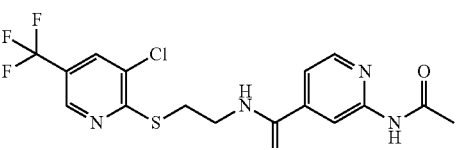<br>Example 52<br>2-acetamido-N-(2-((3-chloro-5-(trifluoromethyl)pyridin-2-yl)thio)ethyl)isonicotinamide | 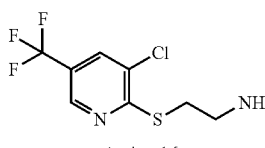<br>Amine-16 | 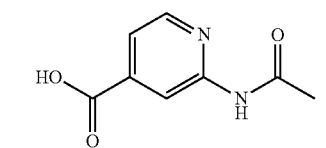<br>Carboxylic acid-16 |
| 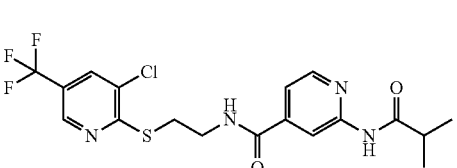<br>Example 53<br>N-(2-((3-chloro-5-(trifluoromethyl)pyridin-2-yl)thio)ethyl)-2-isobutyramidoisonicotinamide | 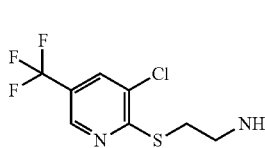<br>Amine-16 | 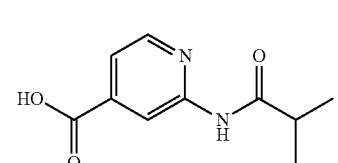<br>Carboxylic acid-3 |

TABLE 2-1-continued

| Example | Reactant | Reactant |
|---|---|---|
| Example 54<br>2-acetamido-N-(2-((3-chloro-5-(trifluoromethyl)pyridin-2-yl)thio)ethyl)-6-methylisonicotinamide | Amine-16 | Carboxylic acid-4 |
| Example 55<br>N-(2-((3-chloro-5-(trifluoromethyl)pyridin-2-yl)thio)ethyl)-2-methyl-6-propionamidoisonicotinamide | Amine-16 | Carboxylic acid-10 |
| Exampl 56<br>2-acetamido-N-(2-((6-(trifluoromethyl)quinolin-2-yl)oxy)ethyl)isonicotinamide | Amine-12 | Carboxylic acid-16 |
| Exampl 57<br>2-propionamido-N-(2-((6-(trifluoromethyl)quinolin-2-yl)oxy)ethyl)isonicotinamide | Amine-12 | Carboxylic acid-1 |
| Example 58<br>2-acetamido-6-methyl-N-(2-((6-(trifluoromethyl)quinolin-2-yl)oxy)ethyl)isonicotinamide | Amine-12 | Carboxylic acid-4 |
| Example 59<br>2-(cyclopropanecarboxamido)-6-methyl-N-(2-((6-(trifluoromethyl)quinolin-2-yl)oxy)ethyl)isonicotinamide | Amine-12 | Carboxylic acid-11 |

TABLE 2-1-continued

| Example | Reactant | Reactant |
|---|---|---|
| 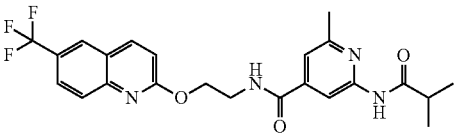<br>Example 60<br>2-isobutyramido-6-methyl-N-(2-((6-(trifluoromethyl)quinolin-2-yl)oxy)ethyl)isonicotinamide | 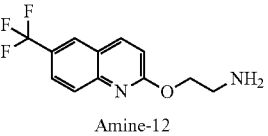 [SMILES: NCCOc1ccc2cc(C(F)(F)F)ccc2n1]<br>Amine-12 | 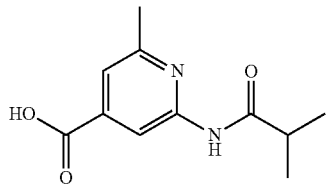<br>Carboxylic acid-5 |
| 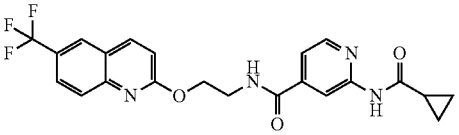<br>Example 61<br>2-(cyclopropanecarboxamido)-N-(2-((6-(trifluoromethyl)quinolin-2-yl)oxy)ethyl)pyrimidine-4-carboxamide | 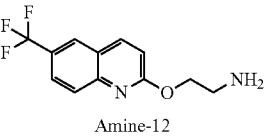 [SMILES: NCCOc1ccc2cc(C(F)(F)F)ccc2n1]<br>Amine-12 | 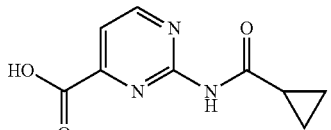<br>Carboxylic acid-7 |
| 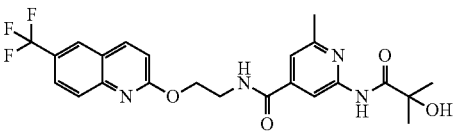<br>Example 62<br>2-(2-hydroxy-2-methylpropanamido)-6-methyl-N-(2-((6-(trifluoromethyl)quinolin-2-yl)oxy)ethyl)isonicotinamide | 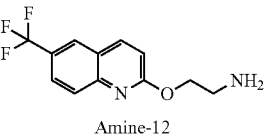 [SMILES: NCCOc1ccc2cc(C(F)(F)F)ccc2n1]<br>Amine-12 | 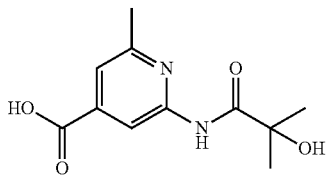<br>Carboxylic acid-15 |
| 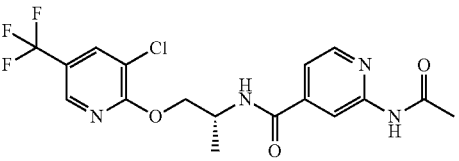<br>Example 63<br>(R)-2-acetamido-N-(1-((3-chloro-5-(trifluoromethyl)pyridin-2-yl)oxy)propan-2-yl)isonicotinamide | 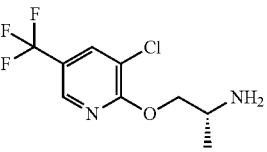<br>Amine-17 | 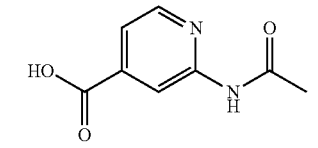<br>Carboxylic acid-16 |
| 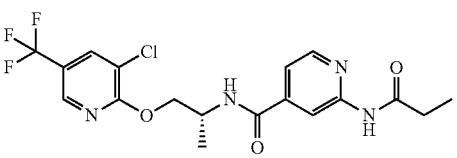<br>Example 64<br>(R)-N-(1-((3-chloro-5-(trifluoromethyl)pyridin-2-yl)oxy)propan-2-yl)-2-propionamidoisonicotinamide | 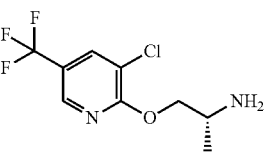<br>Amine-17 | 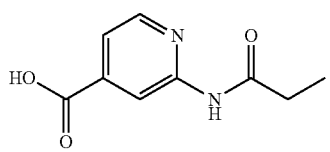<br>Carboxylic acid-1 |
| 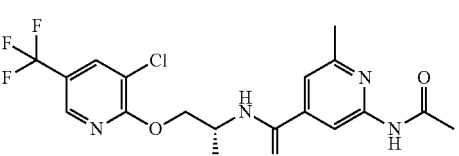<br>Example 65<br>(R)-2-acetamido-N-(1-((3-chloro-5-(trifluoromethyl)pyridin-2-yl)oxy)propan-2-yl)-6-methylisonicotinamide | 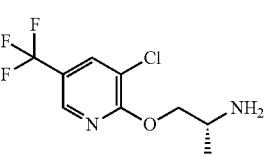<br>Amine-17 | 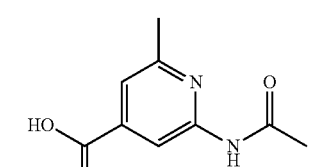<br>Carboxylic acid-4 |

TABLE 2-1-continued

| Example | Reactant | Reactant |
|---|---|---|
| 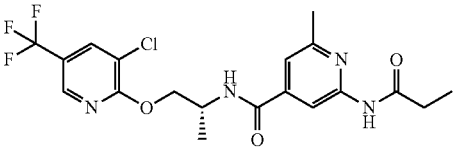<br>Example 66<br>(R)-N-(1-((3-chloro-5-(trifluoromethyl)pyridin-2-yl)oxy)propan-2-yl)-2-methyl-6-propionamidoisonicotinamide | 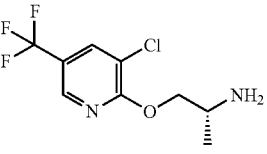<br>Amine-17 | 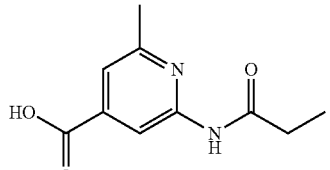<br>Carboxylic acid-10 |
| 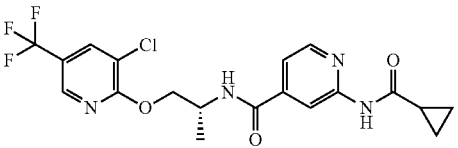<br>Example 67<br>(R)-N-(1-((3-chloro-5-(trifluoromethyl)pyridin-2-yl)oxy)propan-2-yl)-2-(cyclopropanecarboxamido)isonicotinamide | 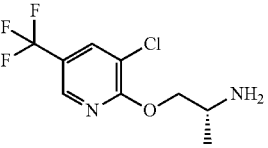<br>Amine-17 | 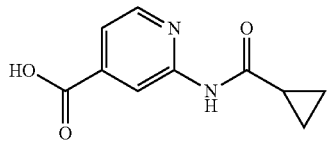<br>Carboxylic acid-2 |
| 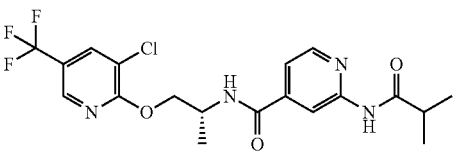<br>Example 68<br>(R)-N-(1-((3-Chloro-5-(trifluoromethyl)pyridin-2-yl)oxy)propan-2-yl)-2-isobutyramidoisonicotinamide | 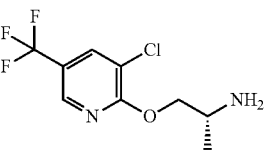<br>Amine-17 | 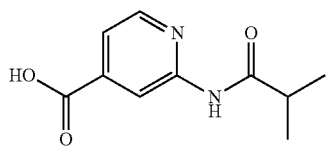<br>Carboxylic acid-3 |
| 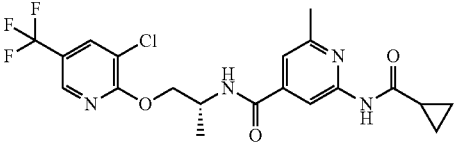<br>Example 69<br>(R)-N-(1-((3-chloro-5-(trifluoromethyl)pyridin-2-yl)oxy)propan-2-yl)-2-(cyclopropanecarboxamido)-6-methylisonicotinamide | 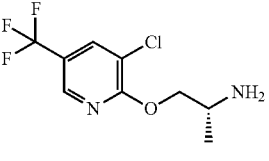<br>Amine-17 | 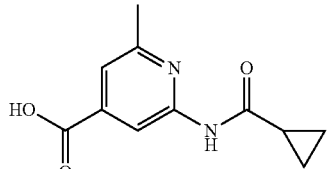<br>Carboxylic acid-11 |
| 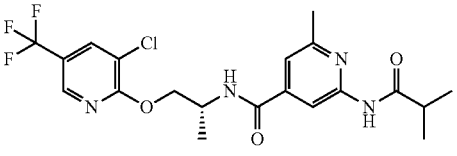<br>Example 70<br>(R)-N-(1-((3-chloro-5-(trifluoromethyl)pyridin-2-yl)oxy)propan-2-yl)-2-isobutyramido-6-methylisonicotinamide | <br>Amine-17 | 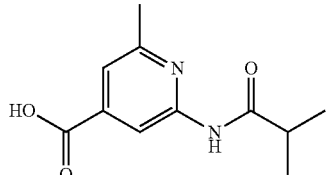<br>Carboxylic acid-5 |
| 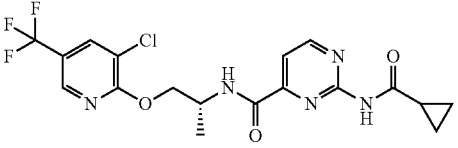<br>Example 71<br>(R)-N-(1-((3-chloro-5-(trifluoromethyl)pyridin-2-yl)oxy)propan-2-yl)-2-(cyclopropanecarboxamido)pyrimidine-4-Carboxamide | 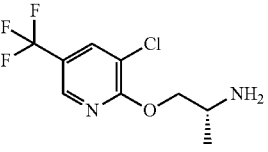<br>Amine-17 | 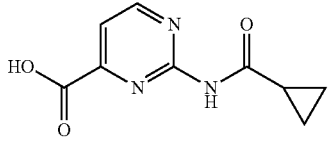<br>Carboxylic acid-7 |

TABLE 2-1-continued

| Example | Reactant | Reactant |
|---|---|---|
| 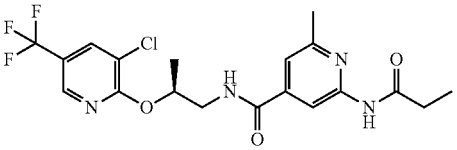<br>Example 72<br>(S)-N-(2-((3-chloro-5-(trifluoromethyl)pyridin-2-yl)<br>oxy)propyl)-2-<br>methyl-6-propionamidoisonicotinamide | 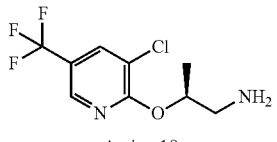<br>Amine-18 | 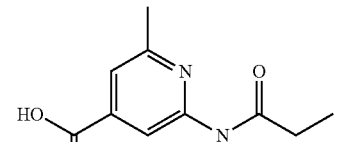<br>Carboxylic acid-10 |
| 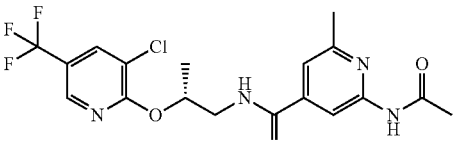<br>Example 73<br>(R)-2-acetamido-N-(2-((3-chloro-5-(trifluoromethyl)<br>pyridin-2-yl)oxy)propyl)-6-methylisonicotinamide | 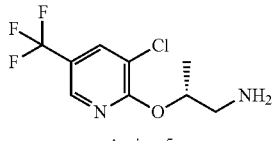<br>Amine-5 | 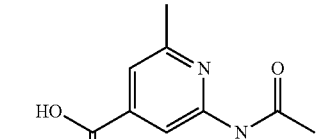<br>Carboxylic acid-4 |
| 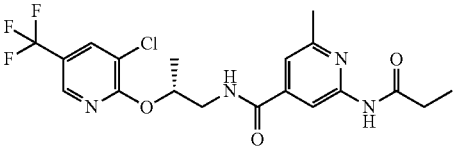<br>Example 74<br>(R)-N-(2-((3-chloro-5-(trifluoromethyl)pyridin-2-yl)<br>oxy)propyl)-2-methyl-6-propionamidoisonicotinamide | 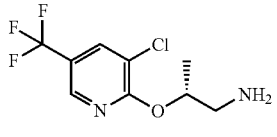<br>Amine-5 | 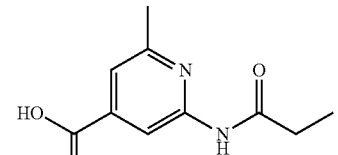<br>Carboxylic acid-10 |
| 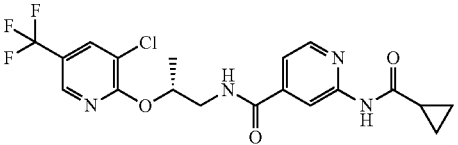<br>Example 75<br>(R)-N-(2-((3-chloro-5-(trifluoromethyl)pyridin-2-yl)oxy)<br>propyl)-2-(cyclopropanecarboxamido)isonicotinamide | 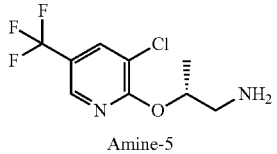 [SMILES: C[C@H](CN)Oc1ncc(C(F)(F)F)cc1Cl]<br>Amine-5 | 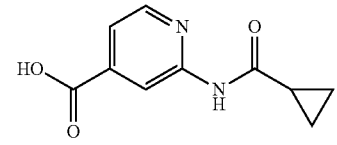<br>Carboxylic acid-2 |
| 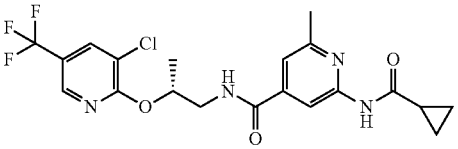<br>Example 76<br>(R)-N-(2-((3-chloro-5-(trifluoromethyl)pyridin-2-yl)<br>oxy)propyl)-2-(cyclopropanecarboxamido)-6-<br>methylisonicotinamide | 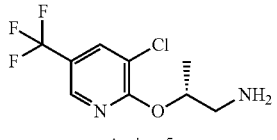<br>Amine-5 | 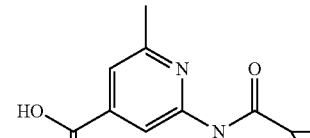<br>Carboxylic acid-11 |
| 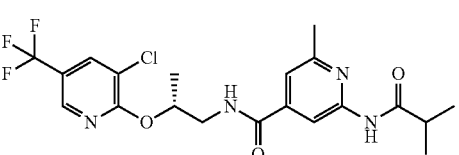<br>Example 77<br>(R)-N-(2-((3-chloro-5-(trifluoromethyl)pyridin-2-yl)oxy)<br>propyl)-2-isobutyramido-6-methylisonicotinamide | 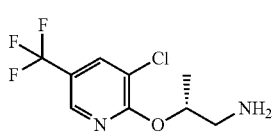<br>Amine-5 | 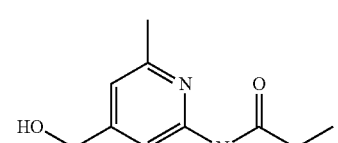<br>Carboxylic acid-5 |

TABLE 2-1-continued

| Example | Reactant | Reactant |
|---|---|---|
| 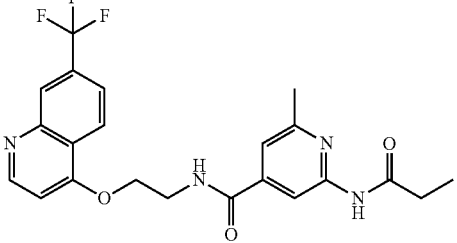<br>Example 78<br>2-methyl-6-propionamido-N-(2-((7-(trifluoromethyl)quinolin-4-yl)oxy)ethyl)isonicotinamide | 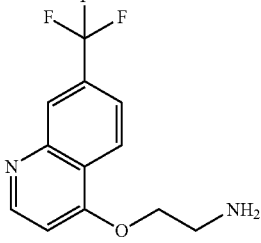<br>Amine-19 | 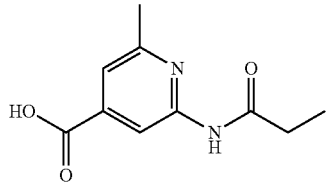<br>Carboxylic acid-10 |
| 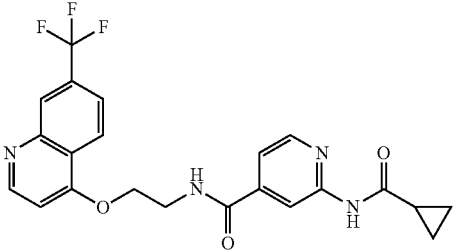<br>Example 79<br>2-(cyclopropanecarboxamido)-N-(2-((7-(trifluoromethyl)quinolin-4-yl)oxy)ethyl)isonicotinamide | 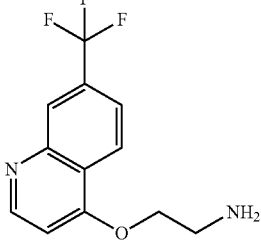<br>Amine-19 | 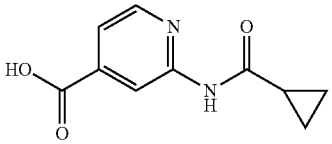<br>Carboxylic acid-2 |
| 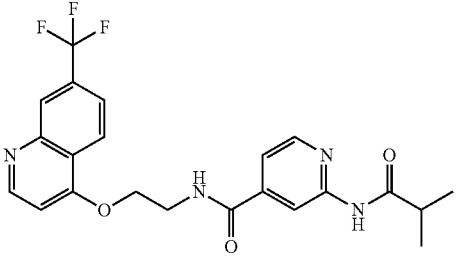<br>Example 80<br>2-isobutyramido-N-(2-((7-(trifluoromethyl)quinolin-4-yl)oxy)ethyl)isonicotinamide | 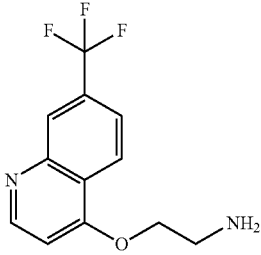<br>Amine-19 | 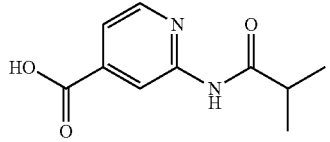<br>Carboxylic acid-3 |
| 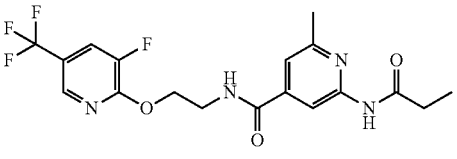<br>Example 81<br>N-(2-((3-fluoro-5-(trifluoromethyl)pyridin-2-yl)oxy)ethyl)-2-methyl-6-propionamidoisonicotinamide | 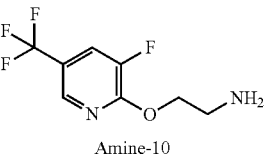 [SMILES: NCCOc1ncc(C(F)(F)F)cc1F]<br>Amine-10 | 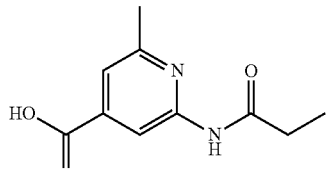<br>Carboxylic acid-10 |
| 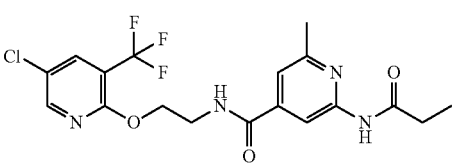<br>Example 82<br>N-(2-((5-chloro-3-(trifluoromethyl)pyridin-2-yl)oxy)ethyl)-2-methyl-6-propionamidoisonicotinamide | 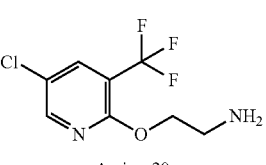<br>Amine-20 | 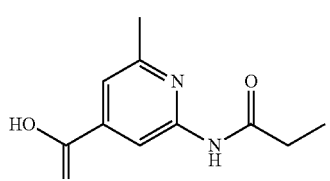<br>Carboxylic acid-10 |

TABLE 2-1-continued

| Example | Reactant | Reactant |
|---|---|---|
| Example 83<br>2-propionamido-N-(2-((4-(trifluoromethyl)quinolin-2-yl)oxy)ethyl)isonicotinamide | Amine-21 | Carboxylic acid-1 |
| Example 84<br>2-methyl-6-propionamido-N-(2-((4-(trifluoromethyl)quinolin-2-yl)oxy)ethyl)isonicotinamide | Amine-21 | Carboxylic acid-10 |
| Example 85<br>2-isobutyramido-N-(2-((4-(trifluoromethyl)quinolin-2-yl)oxy)ethyl)isonicotinamide | Amine-21 | Carboxylic acid-3 |
| Example 86<br>2-(cyclopropanecarboxamido)-N-(2-((4-(trifluoromethyl)quinolin-2-yl)oxy)ethyl)pyrimidine-4-carboxamide | Amine-21 | Carboxylic acid-7 |
| Example 87<br>2-butyramido-N-(2-((3-chloro-5-(trifluoromethyl)pyridin-2-yl)oxy)ethyl)isonicotinamide | Amine-3 | Carboxylic acid-8 |
| Example 88<br>N-(2-((3-chloro-5-(trifluoromethyl)pyridin-2-yl)oxy)ethyl)-2-pivalamidoisonicotinamide | Amine-3 | Carboxylic acid-8 |

TABLE 2-1-continued

| Example | Reactant | Reactant |
|---|---|---|
| 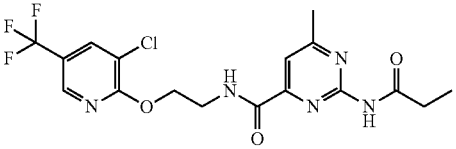<br>Example 89<br>N-(2-((3-chloro-5-(trifluoromethyl)pyridin-2-yl)oxy)<br>ethyl)-6-methyl-2-propionamidopyrimidine-4-<br>carboxamide | 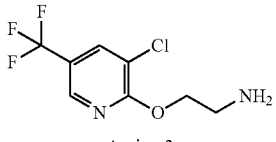<br>Amine-3 | 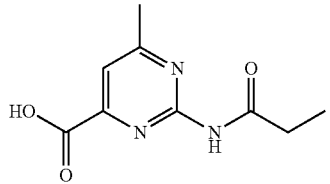<br>Carboxylic acid-13 |
| 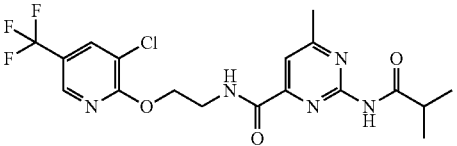<br>Example 90<br>N-(2-((3-chloro-5-(trifluoromethyl)pyridin-2-yl)oxy)<br>ethyl)-2-methyl-2-isobutyramido-6-methylpyrimidine-4-<br>carboxamide | 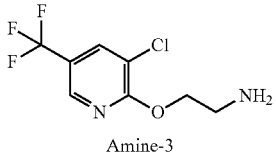<br>Amine-3 | 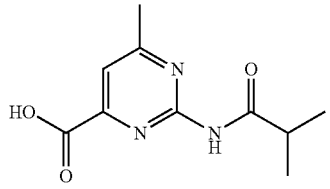<br>Carboxylic acid-14 |
| 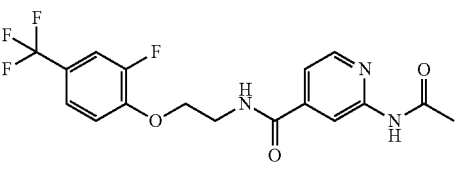<br>Example 91<br>2-acetamido-N-(2-(2-fluoro-4-<br>(trifluoromethyl)phenoxy)ethyl)isonicotinamide | 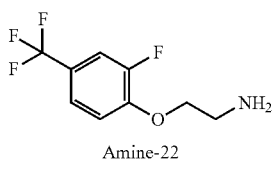 [SMILES: NCCOc1ccc(C(F)(F)F)cc1F]<br>Amine-22 | 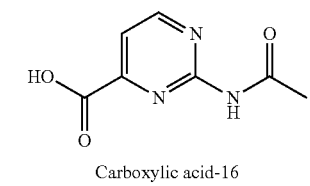<br>Carboxylic acid-16 |
| 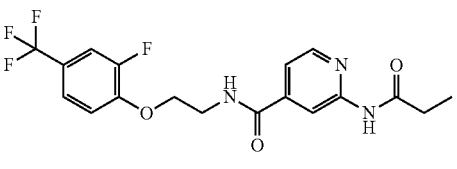<br>Example 92<br>N-(2-(2-fluoro-4-(trifluoromethyl)phenoxy)ethyl-2-<br>propionamidoisonicotinamide | 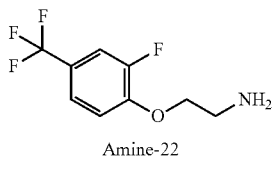 [SMILES: NCCOc1ccc(C(F)(F)F)cc1F]<br>Amine-22 | 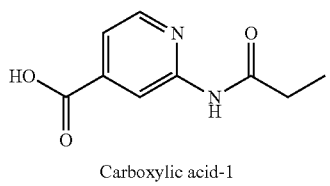<br>Carboxylic acid-1 |
| 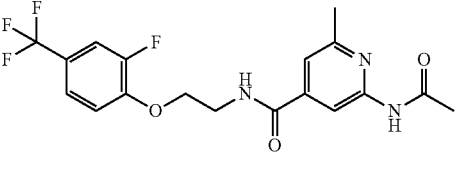<br>Example 93<br>2-acetamido-N-(2-(2-fluoro-4-(trifluoromethyl)<br>phenoxy)ethyl)-6-methylisonicotinamide | 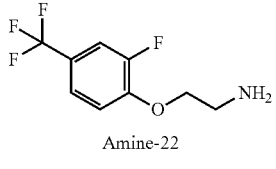 [SMILES: NCCOc1ccc(C(F)(F)F)cc1F]<br>Amine-22 | 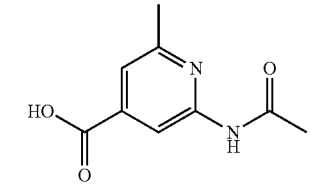<br>Carboxylic acid-4 |
| 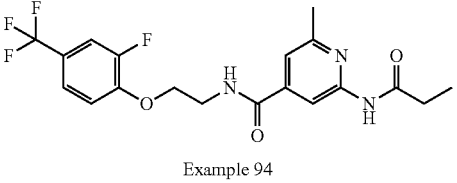<br>Example 94<br>N-(2-(2-fluoro-4-(trifluoromethyl)phenoxy)ethyl)-2-<br>methyl-6-propionamidoisonicotinamide | 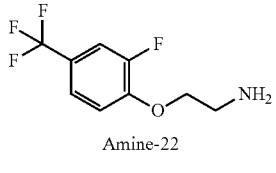 [SMILES: NCCOc1ccc(C(F)(F)F)cc1F]<br>Amine-22 | 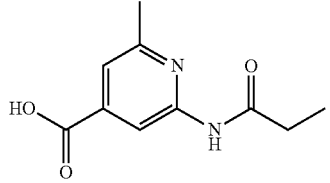<br>Carboxylic acid-10 |

TABLE 2-1-continued

| Example | Reactant | Reactant |
|---|---|---|
| Example 95<br>2-(cyclopropanecarboxamido)-N-(2-(2-fluoro-4-(trifluoromethyl)phenoxy)ethyl)isonicotinamide | Amine-22 | Carboxylic acid-2 |
| Example 96<br>N-(2-(2-fluoro-4-(trifluoromethyl)phenoxy)ethyl)-2-isobutyramidoisonicotinamide | Amine-22 | Carboxylic acid-3 |
| Example 97<br>2-(cyclopropanecarboxamido)-N-(2-(2-fluoro-4-(trifluoromethyl)phenoxy)ethyl)-6-methylisonicotinamide | Amine-22 | Carboxylic acid-11 |
| Example 98<br>N-(2-(2-fluoro-4-(trifluoromethyl)phenoxy)ethyl)-2-isobutyramido-6-methylisonicotinamide | Amine-22 | Carboxylic acid-5 |
| Example 99<br>2-(cyclopropanecarboxamido)-N-(2-(2-fluoro-4-(trifluoromethyl)phenoxy)ethyl)pyrimidine-4-carboxamide | Amine-22 | Carboxylic acid-7 |
| Example 100<br>N-(2-(4-chloro-3-(trifluoromethyl)phenoxy)ethyl)-2-methyl-6-propionamidoisonicotinamide | Amine-23 | Carboxylic acid-10 |

TABLE 2-1-continued

| Example | Reactant | Reactant |
|---|---|---|
| 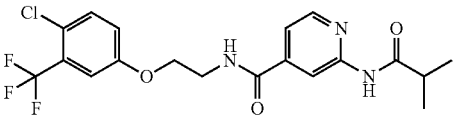<br>Example 101<br>N-(2-(4-chloro-3-(trifluoromethyl)phenoxy)ethyl)-2-isobutyramidoisonicotinamide | 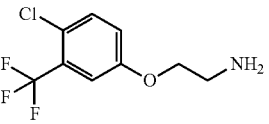<br>Amine-23 | 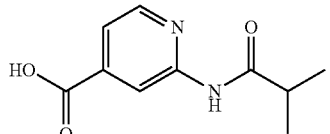<br>Carboxylic acid-3 |
| 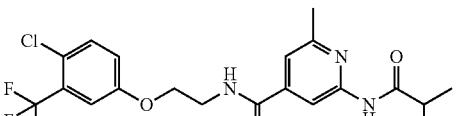<br>Example 102<br>N-(2-(4-chloro-3-(trifluoromethyl)phenoxy)ethyl)-2-isobutyramido-6-methylisonicotinamide | 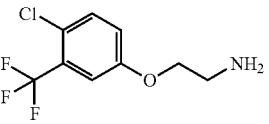<br>Amine-23 | 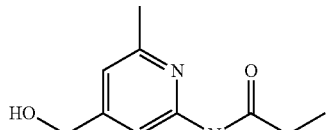<br>Carboxylic acid-5 |
| 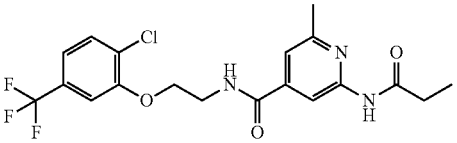<br>Example 103<br>N-(2-(2-chloro-5-(trifluoromethyl)phenoxy)ethyl)-2-methyl-6-propionamidoisonicotinamide | 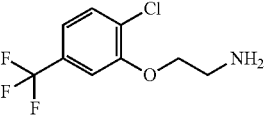<br>Amine-24 | 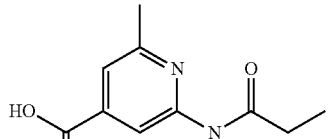<br>Carboxylic acid-10 |
| 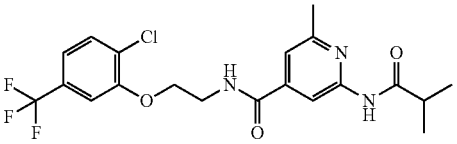<br>Example 104<br>N-(2-(2-chloro-5-(trifluoromethyl)phenoxy)ethyl)-2-isobutyramido-6-methylisonicotinamide | 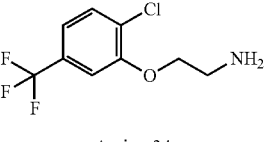<br>Amine-24 | 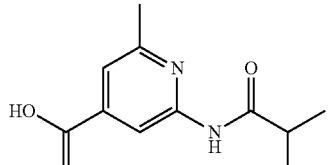<br>Carboxylic acid-5 |
| 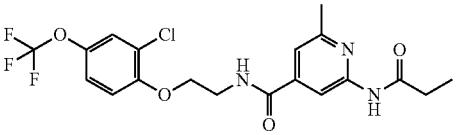<br>Example 105<br>N-(2-(2-chloro-4-(trifluoromethoxy)phenoxy)ethyl)-2-methyl-6-propionamidoisonicotinamide | 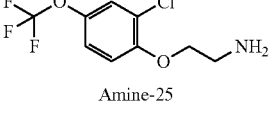<br>Amine-25 | 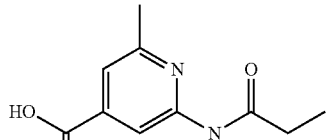<br>Carboxylic acid-10 |
| 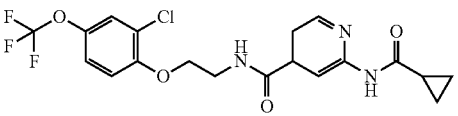<br>Example 106<br>N-(2-(2-chloro-4-(trifluoromethoxy)phenoxy)ethyl)-2-(cyclopropanecarboxamido)isonicotinamide | 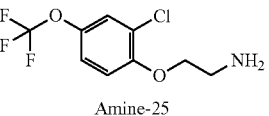 [SMILES: NCCOc1ccc(OC(F)(F)F)cc1Cl]<br>Amine-25 | 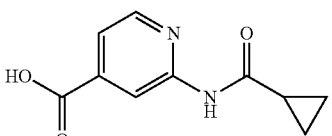<br>Carboxylic acid-2 |
| 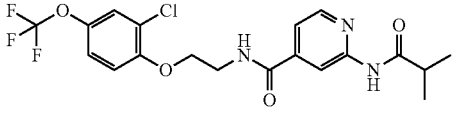<br>Example 107<br>N-(2-(2-chloro-4-(trifluoromethoxy)phenoxy)ethyl)-2-isobutyramidoisonicotinamide | 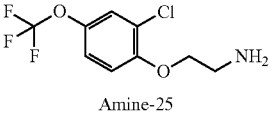 [SMILES: NCCOc1ccc(OC(F)(F)F)cc1Cl]<br>Amine-25 | 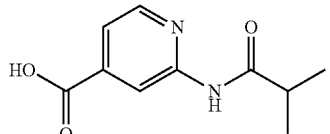<br>Carboxylic acid-3 |

TABLE 2-1-continued

| Example | Reactant | Reactant |
|---|---|---|
| 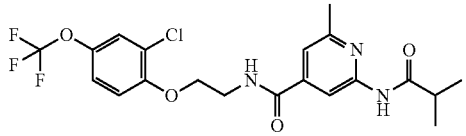<br>Example 108<br>N-(2-(2-chloro-4-(trifluoromethoxy)phenoxy)ethyl)-2-isobutyramido-6-methylisonicotinamide | 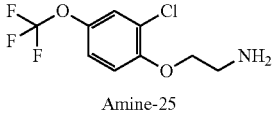 [SMILES: NCCOc1ccc(OC(F)(F)F)cc1Cl]<br>Amine-25 | 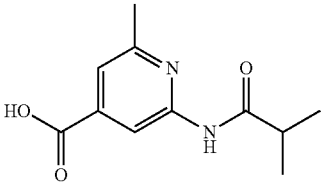<br>Carboxylic acid-5 |
| 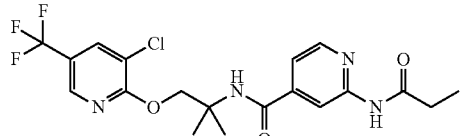<br>Example 109<br>N-(1-((3-chloro-5-(trifluoromethyl)pyridin-2-yl)oxy)-2-methylpropan-2-yl)-2-propionamidoisonicotinamide | 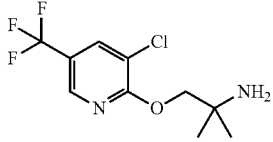<br>Amine-26 | 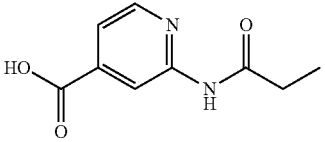<br>Carboxylic acid-1 |
| 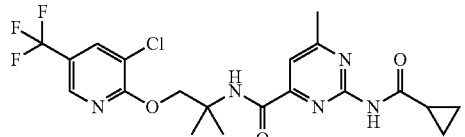<br>Example 110<br>N-(1-((3-chloro-5-(trifluoromethyl)pyridin-2-yl)oxy)-2-methylpropan-2-yl)-2-(cyclopropanecarboxamido)-6-methylpyrimidine-4-carboxamide | 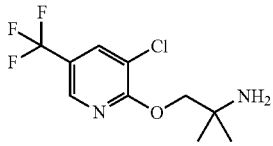<br>Amine-26 | 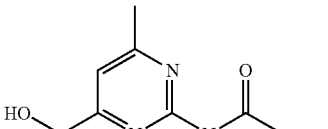<br>Carboxylic acid-6 |
| 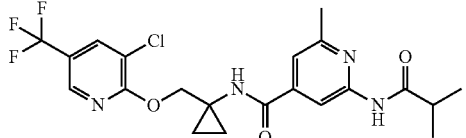<br>Example 111<br>N-(1-(((3-chloro-5-(trifluoromethyl)pyridin-2-yl)oxy)methyl)cyclopropyl)-2-isobutyramido-6-methylisonicotinamide | 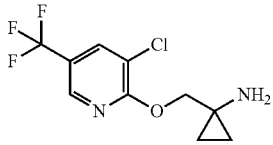<br>Amine-27 | 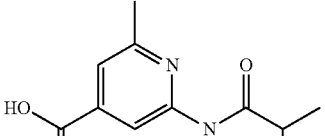<br>Carboxylic acid-5 |
| 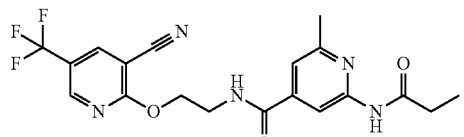<br>Example 112<br>N-(2-((3-cyano-5-(trifluoromethyl)pyridin-2-yl)oxy)ethyl)-2-methyl-6-propionamidoisonicotinamide | 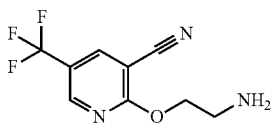<br>Amine-28 | 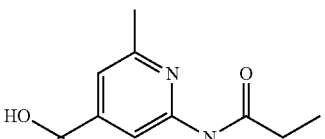<br>Carboxylic acid-10 |
| 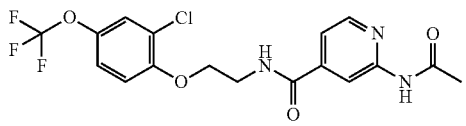<br>Example 113<br>2-acetamido-N-(2-(2-chloro-4-trifluoromethoxy)phenoxy)ethyl)isonicotinamide | 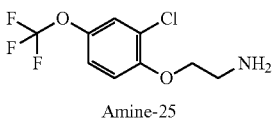<br>Amine-25 | 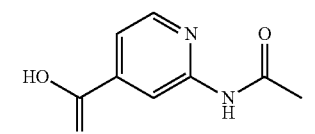<br>Carboxylic acid-16 |

TABLE 2-1-continued

| Example | Reactant | Reactant |
|---|---|---|
| 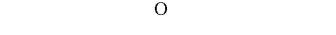<br>Example 114<br>N-(2-(2-chloro-4-(trifluoromethoxy)phenoxy)ethyl)-2-propionamidoisonicotinamide | 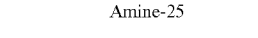<br>Amine-25 | <br>Carboxylic acid-1 |
| <br>Example 115<br>N-(2-(2-chloro-4-(trifluoromethoxy)phenoxy)ethyl)-2-(cyclopropanecarboxamido)-6-methylisonicotinamide | 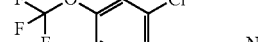<br>Amine-25 | <br>Carboxylic acid-11 |
| <br>Example 116<br>2-acetamido-N-(2-(2-chloro-4-(trifluoromethoxy)phenoxy)ethyl)-6-methylisonicotinamide | 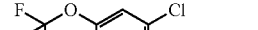<br>Amine-25 | <br>Carboxylic acid-4 |
| <br>Example 117<br>N-(2-(2-chloro-4-(trifluoromethoxy)phenoxy)ethyl)-2-(cyclopropanecarboxamido)pyrimidine-4-carboxamide | <br>Amine-25 | <br>Carboxylic acid-7 |
| <br>Example 118<br>2-acetamido-N-(3-((3-chloro-5-(trifluoromethyl)pyridin-2-yl)amino)propyl)isonicotinamide | <br>Amine-29 | <br>Carboxylic acid-16 |
| 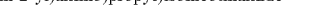<br>Example 119<br>N-(3-((3-chloro-5-(trifluoromethyl)pyridin-2-yl)amino)propyl)-2-propionamidoisonicotinamide | <br>Amine-29 | <br>Carboxylic acid-1 |

TABLE 2-1-continued

| Example | Reactant | Reactant |
|---|---|---|
| 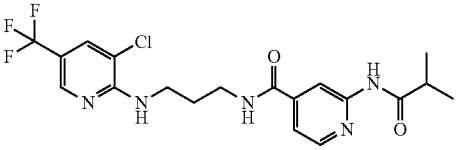<br>Example 120<br>N-(3-((3-chloro-5-(trifluoromethyl)pyridin-2-yl)amino)propyl)-2-isobutyramidoisonicotinamide | 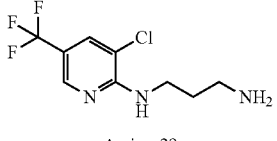<br>Amine-29 | 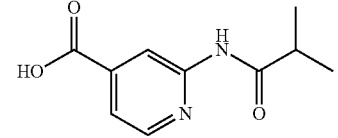<br>Carboxylic acid-3 |
| 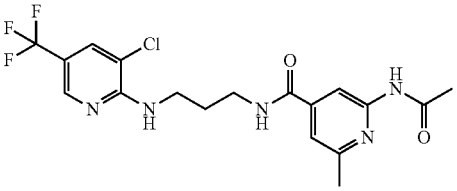<br>Example 121<br>2-acetamido-N-(3-((3-chloro-5-(trifluoromethyl)pyridin-2-yl)amino)propyl)-6-methylisonicotinamide | 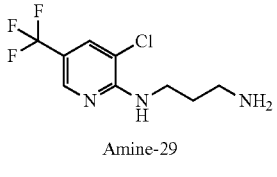 [SMILES: NCCCNc1ncc(C(F)(F)F)cc1Cl]<br>Amine-29 | 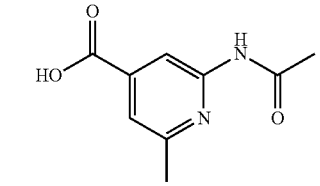<br>Carboxylic acid-4 |
| 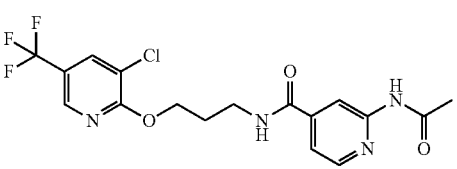<br>Example 122<br>2-acetamido-N-(3-((3-chloro-5-(trifluoromethyl)pyridin-2-yl)oxy)propyl)isonicotinamide | 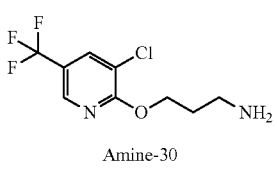 [SMILES: NCCCOc1ncc(C(F)(F)F)cc1Cl]<br>Amine-30 | 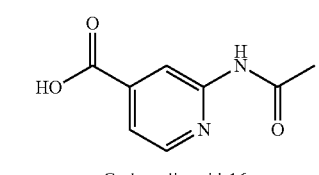<br>Carboxylic acid-16 |
| 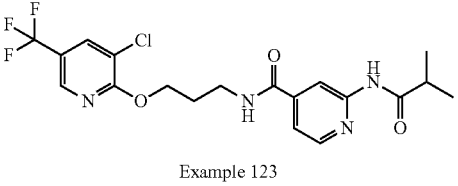<br>Example 123<br>N-(3-((3-chloro-5-(trifluoromethyl)pyridin-2-yl)oxy)propyl)-2-isobutyramidoisonicotinamide | 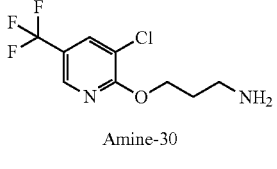 [SMILES: NCCCOc1ncc(C(F)(F)F)cc1Cl]<br>Amine-30 | <br>Carboxylic acid-3 |
| 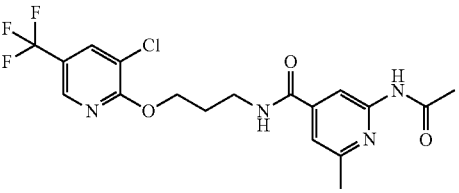<br>Example 124<br>2-acetamido-N-(3-((3-chloro-5-(trifluoromethyl)pyridin-2-yl)oxy)propyl)-6-methylisonicotinamide | 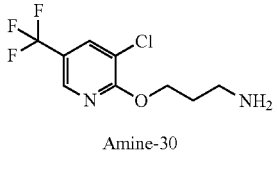 [SMILES: NCCCOc1ncc(C(F)(F)F)cc1Cl]<br>Amine-30 | 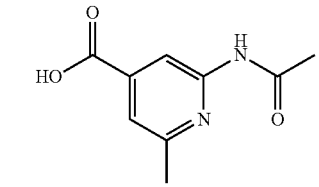<br>Carboxylic acid-4 |
| 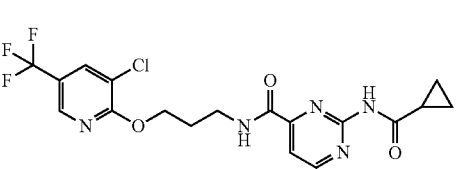<br>Example 125<br>N-(3-((3-chloro-5-(trifluoromethyl)pyridin-2-yl)oxy)propyl)-2-(cyclopropanecarboxamido)-6-methylpyrimidine-4-carboxamide | 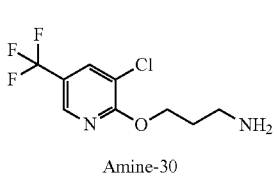 [SMILES: NCCCOc1ncc(C(F)(F)F)cc1Cl]<br>Amine-30 | 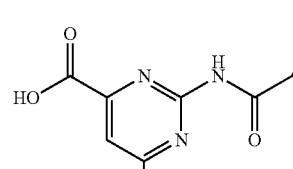<br>Carboxylic acid-6 |

TABLE 2-1-continued

| Example | Reactant | Reactant |
|---|---|---|
| 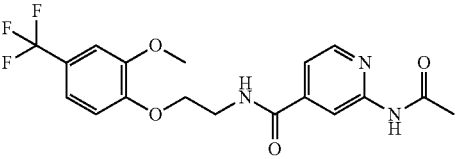<br>Example 126<br>2-acetamido-N-(2-(2-methoxy-4-(trifluoromethyl)phenoxy)ethyl)isonicotinamide | 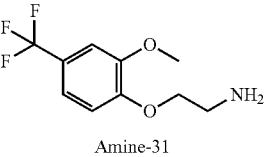 [SMILES: COc1cc(C(F)(F)F)ccc1OCCN]<br>Amine-31 | 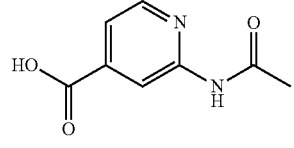<br>Carboxylic acid-16 |
| 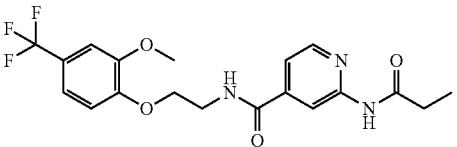<br>Example 127<br>N-(2-(2-methoxy-4-(trifluoromethyl)phenoxy)ethyl)-2-propionamidoisonicotinamide | 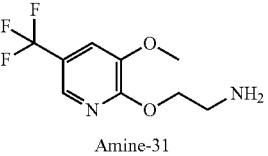 [SMILES: COc1cc(C(F)(F)F)cnc1OCCN]<br>Amine-31 | 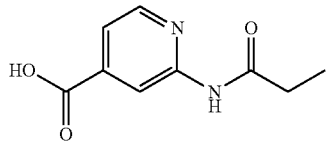<br>Carboxylic acid-1 |
| 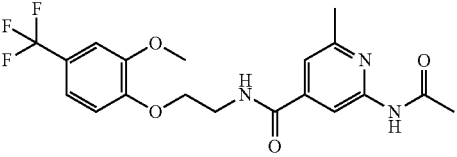<br>Example 128<br>2-acetamido-N-(2-(2-methoxy-4-(trifluoromethyl)phenoxy)ethyl)-6-methylisonicotinamide | 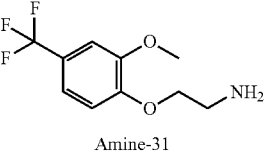 [SMILES: COc1cc(C(F)(F)F)ccc1OCCN]<br>Amine-31 | 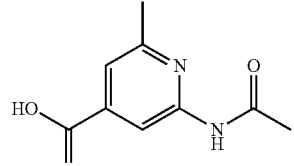<br>Carboxylic acid-4 |
| 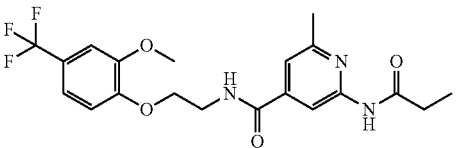<br>Example 129<br>N-(2-(2-methoxy-4-(trifluoromethyl)phenoxy)ethyl)-2-methyl-6-propionamidoisonicotinamide | 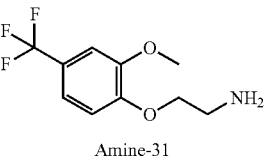 [SMILES: COc1cc(C(F)(F)F)ccc1OCCN]<br>Amine-31 | 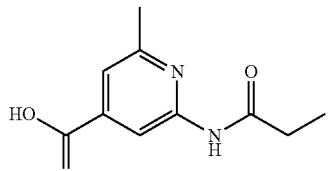<br>Carboxylic acid-10 |
| 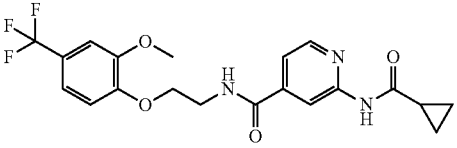<br>Example 130<br>2-(cyclopropanecarboxamido)-N-(2-(2-methoxy-4-(trifluoromethyl)phenoxy)ethyl)isonicotinamide | 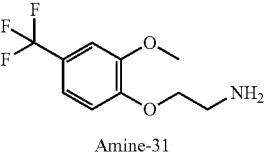 [SMILES: COc1cc(C(F)(F)F)ccc1OCCN]<br>Amine-31 | 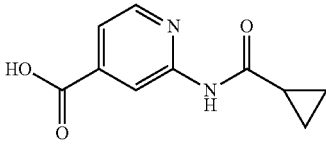<br>Carboxylic acid-2 |
| 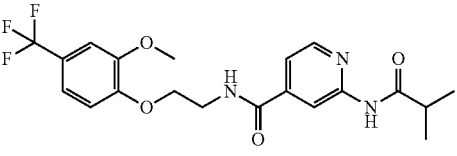<br>Example 131<br>2-isobutyramido-N-(2-(2-methoxy-4-(trifluoromethyl)phenoxy)ethyl)isonicotinamide | 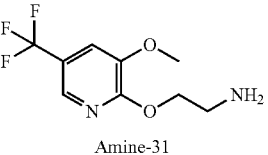 [SMILES: COc1cc(C(F)(F)F)cnc1OCCN]<br>Amine-31 | 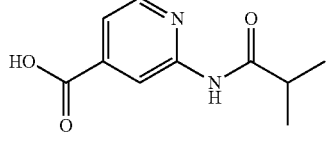<br>Carboxylic acid-3 |

TABLE 2-1-continued

| Example | Reactant | Reactant |
|---|---|---|
| 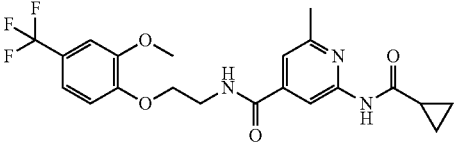<br>Example 132<br>2-(cyclopropanecarboxamido)-N-(2-(2-methoxy-4-(trifluoromethyl)phenoxy)ethyl)-6-methylisonicotinamide | 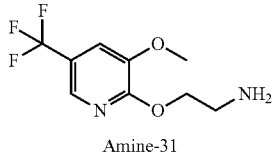 [SMILES: COc1cc(C(F)(F)F)cnc1OCCN]<br>Amine-31 | 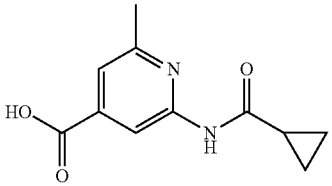<br>Carboxylic acid-11 |
| 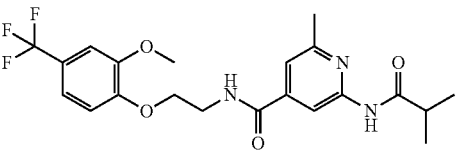<br>Example 133<br>2-isobutyramido-N-(2-(2-methoxy-4-(trifluoromethyl)phenoxy)ethyl)-6-methylisonicotinamide | 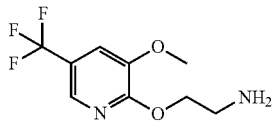<br>Amine-31 | 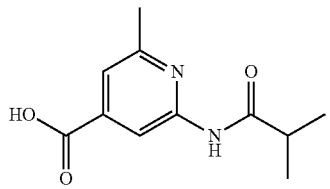<br>Carboxylic acid-5 |
| 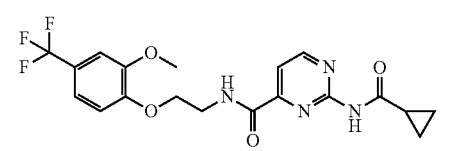<br>Example 134<br>2-(cyclopropanecarboxamido)-N-(2-(2-methoxy-4-(trifluoromethyl)phenoxy)ethyl)pyrimidine-4-carboxamide | 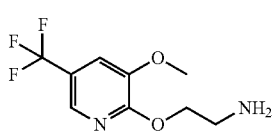<br>Amine-31 | 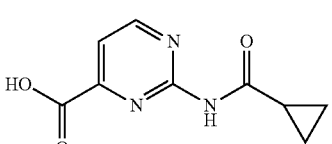<br>Carboxylic acid-7 |
| 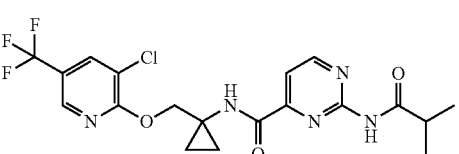<br>Example 135<br>N-(1-(((3-chloro-5-(trifluoromethyl)pyridin-2-yl)oxy)methyl)cyclopropyl)-2-isobutyramido-6-methylpyrimidine-4-carboxamide | 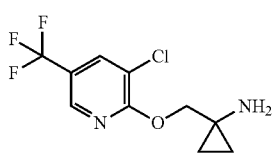<br>Amine-27 | 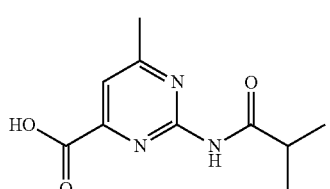<br>Carboxylic acid-14 |
| 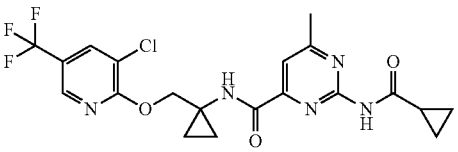<br>Example 136<br>N-(1-(((3-chloro-5-(trifluoromethyl)pyridin-2-yl)oxy)methyl)cyclopropyl)-2-(cyclopropanecarboxamido)-6-methylpyrimidine-4-carboxamide | 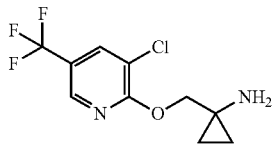<br>Amine-27 | 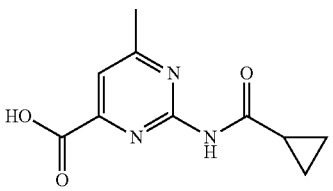<br>Carboxylic acid-6 |
| 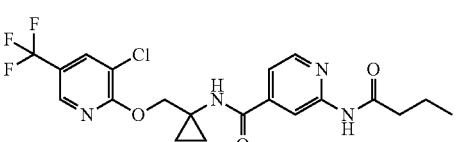<br>Example 137<br>2-butyramido-N-(1-(((3-chloro-5-(trifluoromethyl)pyridin-2-yl)oxy)methyl)cyclopropyl)isonicotinamide | 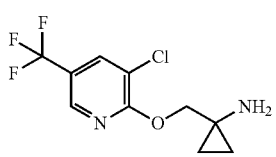<br>Amine-27 | 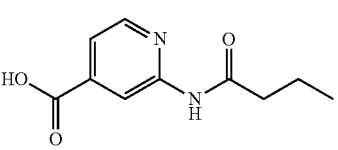<br>Carboxylic acid-8 |

TABLE 2-1-continued

| Example | Reactant | Reactant |
|---|---|---|
| 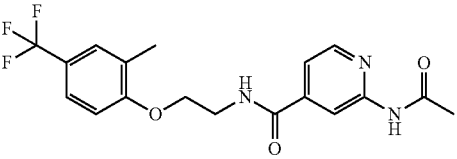<br>Example 138<br>2-acetamido-N-(2-(2-methyl-4-(trifluoromethyl)phenoxy)ethyl)isonicotinamide | 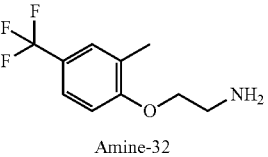<br>Amine-32 | 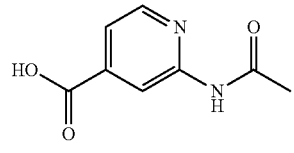<br>Carboxylic acid-16 |
| 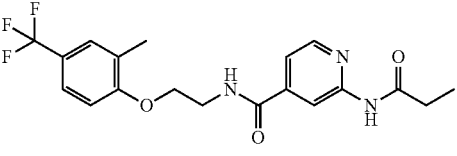<br>Example 139<br>N-(2-(2-methy-4-(trifluoromethyl)phenoxy)ethyl)-2-propionamidoisonicotinamide | 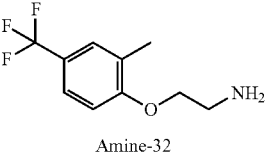<br>Amine-32 | 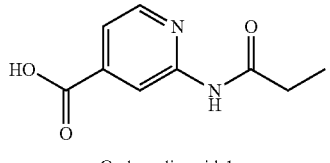<br>Carboxylic acid-1 |
| 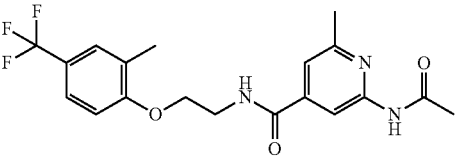<br>Example 140<br>2-acetamido-6-methyl-N-(2-(2-methyl-4-(trifluoromethyl)phenoxy)ethyl)isonicotinamide | 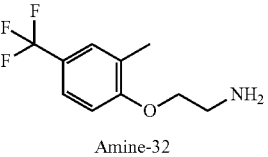<br>Amine-32 | 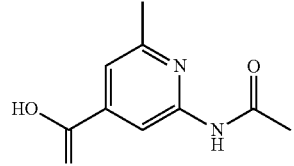<br>Carboxylic acid-4 |
| 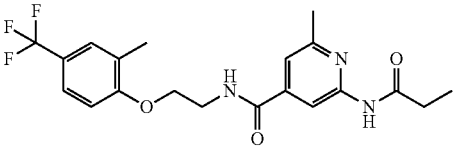<br>Example 141<br>2-methyl-N-(2-(2-methyl-4-(trifluoromethyl)phenoxy)ethyl)-6-propionamidoisonicotinamide | 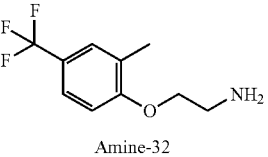<br>Amine-32 | 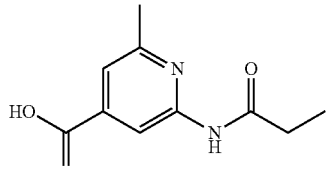<br>Carboxylic acid-10 |
| 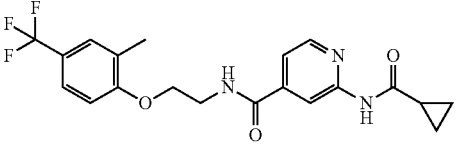<br>Example 142<br>2-(cyclopropanecarboxamido)-N-(2-(2-methyl-4-(trifluoromethyl)phenoxy)ethyl)isonicotinamide | 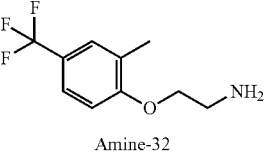<br>Amine-32 | 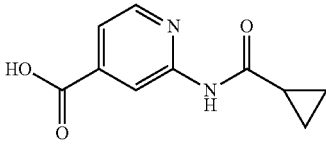<br>Carboxylic acid-2 |
| 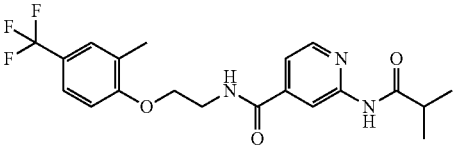<br>Example 143<br>2-isobutyramido-N-(2-(2-methyl-4-(trifluoromethyl)phenoxy)ethyl)isonicotinamide | 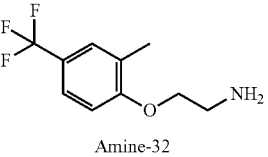<br>Amine-32 | 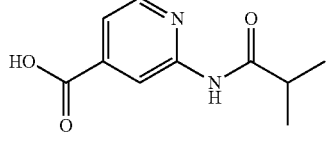<br>Carboxylic acid-3 |

TABLE 2-1-continued

| Example | Reactant | Reactant |
|---|---|---|
| 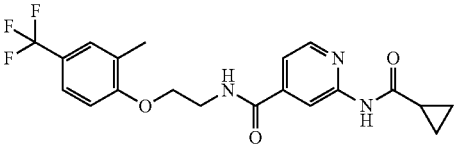<br>Example 144<br>2-(cyclopropanecarboxamido)-6-methyl-N-(2-(2-methyl-4-(trifluoromethyl)phenoxy)ethyl)isonicotinamide | 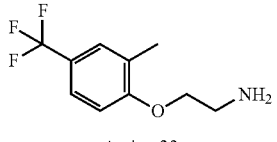<br>Amine-32 | 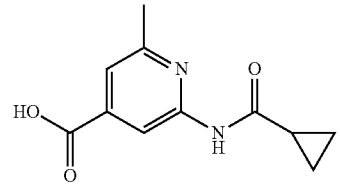<br>Carboxylic acid-11 |
| 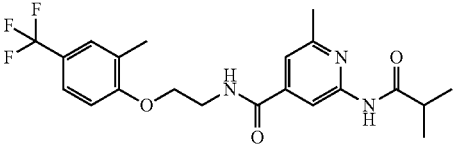<br>Example 145<br>2-isobutyramido-6-methyl-N-(2-(2-methyl-4-(trifluoromethyl)phenoxy)ethyl)isonicotinamide | 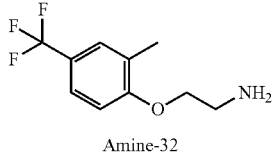<br>Amine-32 | 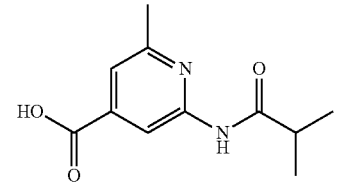<br>Carboxylic acid-5 |
| 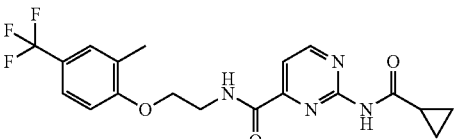<br>Example 146<br>2-(cyclopropanecarboxamido)-N-(2-(2-methyl-4-(trifluoromethyl)phenoxy)ethyl)pyrimidine-4-carboxamide | 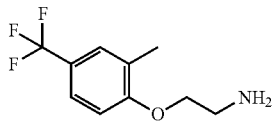<br>Amine-32 | 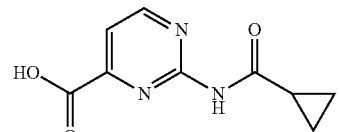<br>Carboxylic acid-7 |
| 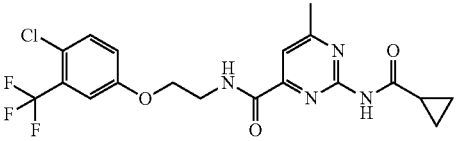<br>Example 147<br>N-(2-(4-chloro-3-(trifluoromethyl)phenoxy)ethyl)-2-cyclopropanecarboxamido)-6-methylpyrimidine-4-carboxamide | 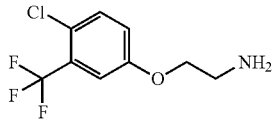<br>Amine-23 | 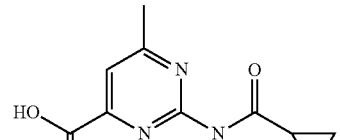<br>Carboxylic acid-6 |
| 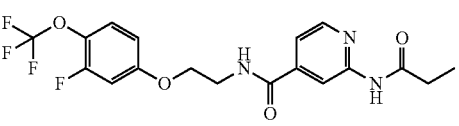<br>Example 148<br>N-(2-(3-fluoro-4-(trifluoromethoxy)phenoxy)ethyl)-2-propionamidoisonicotinamide | 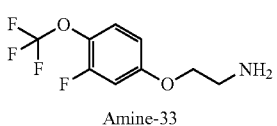 [SMILES: NCCOc1ccc(OC(F)(F)F)c(F)c1]<br>Amine-33 | 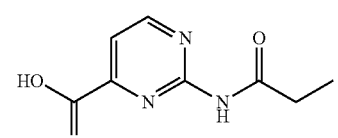<br>Carboxylic acid-1 |
| 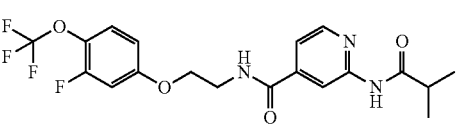<br>Example 149<br>N-(2-(3-fluoro-4-(trifluoromethoxy)phenoxy)ethyl)-2-isobutyramidoisonicotinamide | 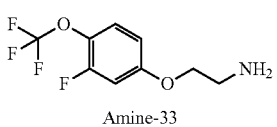 [SMILES: NCCOc1ccc(OC(F)(F)F)c(F)c1]<br>Amine-33 | 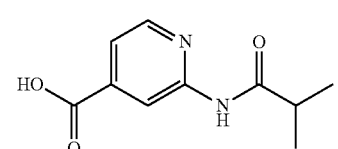<br>Carboxylic acid-3 |

TABLE 2-1-continued

| Example | Reactant | Reactant |
|---|---|---|
| 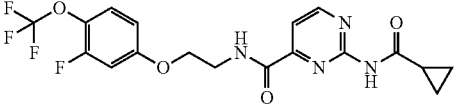 Example 150 2-(cyclopropanecarboxamido)-N-(2-(3-fluoro-4-(trifluoromethoxy)phenoxy)ethyl)pyrimidine-4-carboxamide | 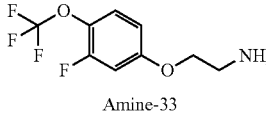 Amine-33 | 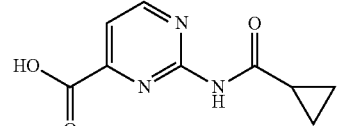 Carboxylic acid-7 |
| 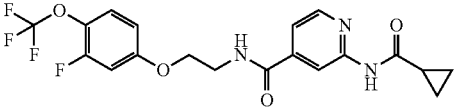 Example 151 2-(cyclopropanecarboxamido)-N-(2-(3-fluoro-4-(trifluoromethoxy)phenoxy)ethyl)isonicotinamide | 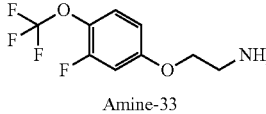 Amine-33 | 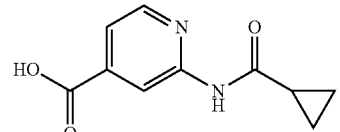 Carboxylic acid-2 |
| 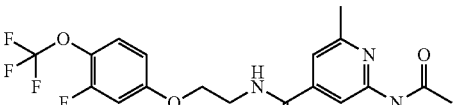 Example 152 2-acetamido-N-(2-(3-fluoro-4-(trifluoromethoxy)phenoxy)ethyl)-6-methylisonicotinamide | 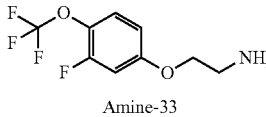 Amine-33 | 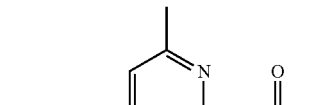 Carboxylic acid-4 |
| 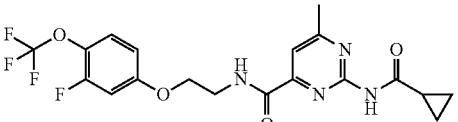 Example 153 2-(cyclopropanecarboxamido)-N-(2-(3-fluoro-4-(trifluoromethoxy)phenoxy)ethyl)-6-methylpyrimidine-4-carboxamide | 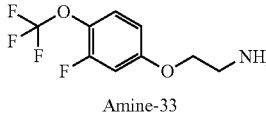 Amine-33 | 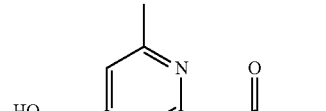 Carboxylic acid-6 |
| 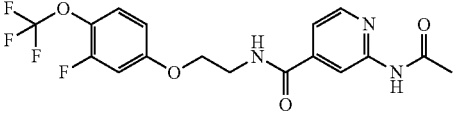 Example 154 2-acetamido-N-(2-(3-fluoro-4-(trifluoromethoxy)phenoxy)ethyl)isonicotinamide | 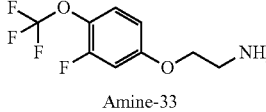 Amine-33 | 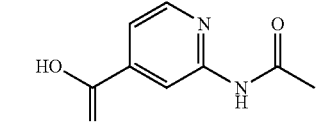 Carboxylic acid-16 |
| 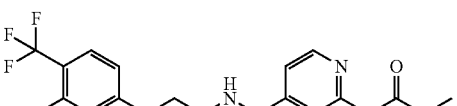 Example 155 N-(2-(3-fluoro-4-(trifluoromethyl)phenoxy)ethyl)-2-isobutyramidoisonicotinamide | 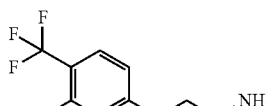 Amine-34 | 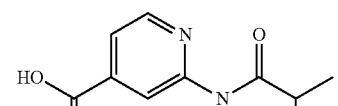 Carboxylic acid-3 |

| | LC-MS | | |
|---|---|---|---|
| Ex | tR (min) | m/z | Method |
| 1 | 1.70 | 408.0 | A |
| 2 | 1.51 | 400.2 | A |
| 3 | 1.60 | 414.2 | A |
| 4 | 1.57 | 414.1 | A |
| 5 | 1.66 | 428.1 | A |
| 6 | 1.64 | 426.1 | A |

-continued

| Ex | tR (min) | m/z | Method |
|---|---|---|---|
| 7 | 1.69 | 428.1 | A |
| 8 | 1.54 | 403.0 | A |
| 9 | 1.63 | 417.0 | A |
| 10 | 1.60 | 417.0 | A |
| 11 | 1.58 | 418.0 | A |
| 12 | 1.58 | 397.0 | A |
| 13 | 1.71 | 430.9 | A |
| 14 | 1.67 | 428.9 | A |
| 15 | 1.69 | 430.9 | A |
| 16 | 1.69 | 443.9 | A |
| 17 | 1.85 | 445.0 | C |
| 18 | 1.74 | 412.1 | A |
| 19 | 1.64 | 398.0 | A |
| 20 | 1.61 | 402.0 | A |
| 21 | 1.70 | 416.0 | A |
| 22 | 1.77 | 430.0 | A |
| 23 | 1.67 | 416.0 | A |
| 24 | 1.60 | 382.1 | A |
| 25 | 1.68 | 443.3 | B |
| 26 | 1.66 | 442.3 | B |
| 27 | 1.59 | 427.3 | B |
| 28 | 1.52 | 415.3 | B |
| 29 | 1.76 | 429.1 | C |
| 30 | 1.54 | 415.3 | B |
| 31 | 1.60 | 440.2 | B |
| 32 | 1.62 | 440.2 | B |
| 33 | 1.65 | 452.2 | B |
| 34 | 1.69 | 454.2 | B |
| 35 | 1.85 | 445.0 | C |
| 36 | 1.66 | 430.0 | C |
| 37 | 1.82 | 444.0 | C |
| 38 | 1.62 | 429.0 | C |
| 39 | 1.80 | 430.0 | C |
| 40 | 1.77 | 428.0 | C |
| 41 | 1.85 | 442.0 | C |
| 42 | 1.89 | 444.0 | C |
| 43 | 1.72 | 429.0 | C |
| 44 | 1.83 | 447.0 | C |
| 45 | 1.80 | 445.0 | C |
| 46 | 1.84 | 447.0 | C |
| 47 | 1.72 | 446.1 | C |
| 48 | 1.83 | 447.0 | C |
| 49 | 1.83 | 476.0 | C |
| 50 | 1.80 | 474.0 | C |
| 51 | 1.84 | 476.0 | C |
| 52 | 1.66 | 418.9 | C |
| 53 | 1.87 | 447.0 | C |
| 54 | 1.74 | 433.0 | C |
| 55 | 1.85 | 447.0 | C |
| 56 | 1.65 | 419.0 | C |
| 57 | 1.75 | 433.0 | C |
| 58 | 1.72 | 433.0 | C |
| 59 | 1.87 | 459.0 | C |
| 60 | 1.91 | 461.0 | C |
| 61 | 1.75 | 446.0 | C |
| 62 | 1.78 | 477.0 | C |
| 63 | 1.63 | 417.0 | C |
| 64 | 1.75 | 431.0 | C |
| 65 | 1.71 | 431.0 | C |
| 66 | 1.83 | 445.0 | C |
| 67 | 1.80 | 443.0 | C |
| 68 | 1.83 | 445.0 | C |
| 69 | 1.87 | 457.0 | C |
| 70 | 1.92 | 459.0 | C |
| 71 | 1.76 | 444.0 | C |
| 72 | 1.84 | 445.0 | C |
| 73 | 1.72 | 431.0 | C |
| 74 | 1.83 | 445.0 | C |
| 75 | 1.81 | 443.0 | C |
| 76 | 1.88 | 457.0 | C |
| 77 | 1.93 | 459.0 | C |
| 78 | 1.74 | 447.0 | C |
| 79 | 1.70 | 445.0 | C |
| 80 | 1.75 | 447.0 | C |
| 81 | 1.67 | 415.1 | C |
| 82 | 1.75 | 431.0 | C |
| 83 | 1.81 | 433.1 | C |
| 84 | 1.89 | 447.0 | C |
| 85 | 1.90 | 447.0 | C |
| 86 | 1.81 | 446.0 | C |
| 87 | 1.76 | 431.1 | C |
| 88 | 1.88 | 445.1 | C |
| 89 | 1.72 | 432.0 | C |
| 90 | 1.80 | 446.0 | C |
| 91 | 1.55 | 386.1 | C |
| 92 | 1.65 | 400.1 | C |
| 93 | 1.62 | 400.1 | C |
| 94 | 1.72 | 414.1 | C |
| 95 | 1.69 | 412.1 | C |
| 96 | 1.74 | 414.1 | C |
| 97 | 1.77 | 426.1 | C |
| 98 | 1.81 | 428.1 | C |
| 99 | 1.64 | 413.1 | C |
| 100 | 1.81 | 430.1 | C |
| 101 | 1.82 | 430.1 | C |
| 102 | 1.90 | 444.1 | C |
| 103 | 1.79 | 430.0 | C |
| 104 | 1.87 | 444.0 | C |
| 105 | 1.83 | 446.2 | C |
| 106 | 1.79 | 444.2 | C |
| 107 | 1.84 | 446.2 | C |
| 108 | 1.91 | 460.2 | C |
| 109 | 1.84 | 445.1 | A |
| 110 | 1.93 | 472.1 | A |
| 111 | 1.90 | 471.0 | C |
| 112 | 1.60 | 422.1 | C |
| 113 | 1.65 | 418.0 | C |
| 114 | 1.75 | 432.1 | C |
| 115 | 1.87 | 458.1 | C |
| 116 | 1.73 | 432.0 | C |
| 117 | 1.75 | 445.0 | C |
| 118 | 1.57 | 414.3 | A |
| 119 | 1.66 | 428.3 | A |
| 120 | 1.74 | 442.2 | A |
| 121 | 1.63 | 428.3 | A |
| 122 | 1.60 | 417.0 | A |
| 123 | 1.77 | 445.0 | A |
| 124 | 1.66 | 431.0 | A |
| 125 | 1.74 | 456.1 | A |
| 126 | 1.49 | 398.2 | C |
| 127 | 1.60 | 412.2 | C |
| 128 | 1.57 | 412.2 | C |
| 129 | 1.67 | 426.2 | C |
| 130 | 1.65 | 424.2 | C |
| 131 | 1.69 | 426.2 | C |
| 132 | 1.72 | 438.2 | C |
| 133 | 1.76 | 440.2 | C |
| 134 | 1.59 | 425.1 | C |
| 135 | 1.87 | 472.1 | C |
| 136 | 1.82 | 470.1 | C |
| 137 | 1.81 | 457.1 | C |
| 138 | 1.63 | 382.2 | C |
| 139 | 1.74 | 396.2 | C |
| 140 | 1.71 | 396.2 | C |
| 141 | 1.81 | 410.2 | C |
| 142 | 1.78 | 408.2 | C |
| 143 | 1.82 | 410.2 | C |
| 144 | 1.86 | 422.2 | C |
| 145 | 1.90 | 424.2 | C |
| 146 | 1.74 | 409.2 | C |
| 147 | 1.83 | 443.0 | C |
| 148 | 1.72 | 416.1 | C |
| 149 | 1.81 | 430.1 | C |
| 150 | 1.72 | 429.1 | C |
| 151 | 1.76 | 428.1 | C |
| 152 | 1.69 | 416.1 | C |
| 153 | 1.80 | 443.1 | C |
| 154 | 1.61 | 402.0 | C |
| 155 | 1.77 | 414.1 | C |

TABLE 4-1

| Example | salt | data |
|---|---|---|
| 2 | free | $^1$H-NMR (270 MHz, DMSO-$d_6$) delta 10.61 (1H, s), 8.82-8.77 (1H, m), 8.43-3.38 (2H, m), 8.32 (1H, s), 7.97 (1H, s), 7.47-7.37 (2H, m), 3.66-3.57 (2H, m), 3.52-3.40 (2H, m), 2.11 (3H, s). |
| 7 | free | $^1$H-NMR (400 MHz, CDCl$_3$) delta 8.54 (1H, d, J = 0.9 Hz), 8.49 (1H, d, J = 1.4 Hz), 8.36 (1H, dd, J = 5.0, 0.9 Hz), 8.13 (1H, br. s), 8.01-7.96 (1H, m), 7.64 (1H, d, J = 1.8 Hz), 7.54 (1H, dd, J = 5.0, 1.4 Hz), 5.97-5.90 (1H, m), 3.88-3.80 (2H, m), 3.76-3.69 (2H, m), 2.59 (1H, septet, J = 6.9 Hz), 1.29 (6H, d, J = 6.9 Hz). |
| 13 | free | $^1$H-NMR (400 MHz, CDCl$_3$) delta 8.54 (1H, d, J = 0.9 Hz), 8.49 (1H, dd, J = 2.2, 0.9 Hz), 8.38 (1H, d, J = 6.0 Hz), 8.17 (1H, br. s), 7.87 (1H, d, J = 2.2 Hz), 7.56-7.53 (1H, m), 7.45-7.37 (1H, m), 4.70 (2H, t, J = 5.0 Hz), 3.95-3.89 (2H, m), 2.58 (1H, septet, J = 6.9 Hz), 1.28 (6H, d, J = 6.9 Hz). |
| 15 | free | $^1$H-NMR (400 MHz, DMSO-$d_6$) delta 10.51 (1H, s), 8.84-8.78 (1H, m), 8.57-8.54 (1H, m), 8.38 (1H, d, J = 1.8 Hz), 8.23 (1H, s), 7.23 (1H, s), 4.61 (2H, t, J = 5.5 Hz), 3.71-3.64 (2H, m), 2.44 (3H, s), 2.38 (1H, q, J = 7.3 Hz), 1.06 (3H, t, J = 7.3 Hz). |
| 22 | free | $^1$H-NMR (400 MHz, CDCl$_3$) delta 8.54 (1H, d, J = 0.9 Hz), 8.38 (1H, d, J = 4.6 Hz), 8.17 (1H, br. s), 7.63 (1H, d, J = 2.3 Hz), 7.50-7.47 (2H, m), 7.13-7.08 (1H, m), 7.02 (1H, d, J = 8.7 Hz), 4.27 (2H, t, J = 5.0 Hz), 3.96-3.91 (2H, m), 2.58 (1H, septet, J = 6.9 Hz), 1.27 (6H, d, J = 6.9 Hz). |
| 35 | free | $^1$H-NMR (400 MHz, DMSO-$d_6$) delta 10.51 (1H, s), 8.84-8.80 (1H, m), 8.55 (1H, d, J = 0.9 Hz), 8.38 (1H, d, J = 2.3 Hz), 8.25 (1H, s), 7.24 (1H, s), 4.61 (2H, t, J = 5.5 Hz), 3.71-3.64 (2H, m), 2.76 (1H, septet, J = 6.9 Hz), 2.44 (3H, s), 1.08 (6H, d, J = 6.9 Hz). |
| 42 | free | $^1$H-NMR (400 MHz, DMSO-$d_6$) delta 10.52 (1H, s), 8.88-8.84 (1H, m), 8.28 (1H, s), 7.83 (1H, d, J = 1.8 Hz), 7.69 (1H, dd, J = 8.7, 1.8 Hz), 7.41 (1H, d, J = 8.7 Hz), 7.28 (1H, d, J = 0.9 Hz), 4.33 (2H, t, J = 5.5 Hz), 3.71-3.64 (2H, m), 2.76 (1H, septet, J = 6.9 Hz), 2.45 (3H, s), 1.08 (6H, d, J = 6.9 Hz). |
| 53 | free | $^1$H-NMR (400 MHz, CDCl$_3$) delta 8.74 (1H, dd, J = 1.8, 0.9 Hz), 8.48 (1H, d, J = 0.9 Hz), 8.35 (1H, dd, J = 5.0, 0.9 Hz), 8.20 (1H, br. s), 7.75 (1H, d, J = 1.4 Hz), 7.53-7.50 (1H, m), 7.50-7.47 (1H, m), 3.87-3.80 (2H, m), 3.57-3.50 (2H, m), 2.59 (1H, septet, J = 6.9 Hz), 1.28 (6H, d, J = 6.9 Hz). |
| 68 | free | $^1$H-NMR (400 MHz, CDCl$_3$) delta 8.49 (1H, d, J = 0.9 Hz), 8.46-8.45 (1H, m), 8.37 (1H, d, J = 5.0 Hz), 8.16 (1H, br. s), 7.85 (1H, d, J = 2.3 Hz), 7.53 (1H, dd, J = 5.0, 1.4 Hz), 7.20-7.15 (1H, m), 4.68-4.51 (3H, m), 2.58 (1H, septet, J = 6.9 Hz), 1.40 (3H, d, J = 6.9 Hz), 1.28 (6H, d, J = 6.9 Hz). |
| 96 | free | $^1$H-NMR (400 MHz, CDCl$_3$) delta 8.52 (1H, d, J = 0.9 Hz), 8.38 (1H, d, J = 4.6 Hz), 8.13 (1H, br. s), 7.50 (1H, dd, J = 5.0, 1.4 Hz), 7.39-7.30 (2H, m), 7.11-7.02 (2H, m), 4.27 (2H, t, J = 5.0 Hz), 3.96-3.89 (2H, m), 2.58 (1H, septet, J = 6.9 Hz), 1.27 (6H, d, J = 6.9 Hz). |

Pharmacological Assays

In Vitro Activities Against Human Voltage Gated Sodium Channels

The inhibitory activities of compounds against voltage gated sodium channels are determined by methodology well known in the art.

The ability of the amide derivatives of the formulae (I), (II) and (III) to inhibit the Nav1.7, Nav1.8 and Nav1.5 channels is measured by Fluorescence Resonance Energy Transfer (FRET) assay and electrophysiology assay described below.

EFS-FRET Assay

This screen is used to determine the effects of compounds on human Nav1.7 channels, utilizing electrical field stimulation (EFS) system in 96-well plate format on FDSS (Hamamatsu Photonics) platform. The change of membrane potential is monitored with FRET dye pair, DiSBAC2(3) and PTS 18.

Cell Maintenance:

CHO (Chinese hamster ovary) cells expressing human Nav1.7 channels are grown in T225 flasks, in a 5% $CO_2$ humidified incubator to about 80% confluence. Media composition consists of HAM/F·12 with Glutamax I, 10% FCS, 100 units/mL penicillin and 100 microgram/mL hygromycin.

Protocol:

Seed each cell lines (1×10$^5$ cells/well) into 96-well plates prior to experimentation.

Incubate at 37° C. in 5% CO, for 24 hours.

Wash each well with assay buffer (140 mM NaCl, 4:5 mM KCl, 10 mM D-Glucose, 2 mM $CaCl_2$, 1 mM $MgCl_2$, 10 mM HEPES, pH 7.4 adjusted with NaOH) twice.

Add 1st loading solution containing 10 microM PTS18 and 0.06% Pluronic F-127 in assay buffer.

Incubate the plate at rt in dark for 1 hour.

Remove 1st loading solution and add 2nd loading solution containing 12.5 microM DiSBAC2(3), 1.25 mM Xylene Fast Yellow and 0.0075% Pluronic F-127 in assay buffer.

Place the plate under the dark at rt for 25 minutes.

Add compound solutions into the assay plate.

Set the assay plate in FDSS and place an EFS device on the plate.

Measure EFS-induced fluorescent response by FDSS.

The data are analyzed and reported as normalized ratios of intensities measured at 440 nm. The process of calculating these ratios is performed as follows:

$$\% \text{ inhibition} = 1 - \frac{(FIR \text{ of each well} - \text{median } FIR \text{ in } 100\% \text{ Inhibition})}{(\text{median } FIR \text{ in } 0\% \text{ Inhibition} - \text{median } FIR \text{ in } 100\% \text{ inhibition})} \times 100 \quad \text{[Math. 1]}$$

"$FIR$" = Flourescence Integration Ratio
= the integral of the radio normalized by base (before $EFS$)

This analysis is performed using a computerized specific program designed for

FDSS generated data. Fluorescence ratio values are plotted using XLfit to determine an $IC_{50}$ value for each, compound.

All tested compounds of Examples show less than about 1 microM of $IC_{50}$ against Nav1.7 in the above assays. Preferable compounds show less than about 0.5 microM of $IC_{50}$ against Nav1.7 in the above assays.

Compounds with $IC_{50}$ against Nav1.7<0.5 microM are:

Examples 2, 3, 4, 5, 6, 7, 9, 10, 12, 13, 14, 15, 16, 19, 21, 22, 23, 25, 26, 28, 30, 31, 32, 33, 34, 35, 36, 37, 38, 39, 40, 41, 42, 43, 44, 45, 46, 49, 54, 56, 57, 58, 59, 60, 61, 64, 65, 66, 67, 68, 69, 70, 71, 73, 74, 76, 77, 80, 87, 89,90, 93, 94, 96, 97, 98, 105, 106, 107, 108, 113, 114, 115, 116, 117, 119, 123, 126, 127, 128, 129, 130, 131, 132, 133, 134, 138, 139, 140, 141, 142, 143, 144, 145, 146, 148, 149, 150, 151, 152, and 154.

FRET Assay

This screen is used to determine the effects of compounds on human Nav1.8, and human Nav1.5 channels, utilizing the cell imaging technology by Hamamatsu Photonics's Functional Drug Screening System (FDSS). The changes of membrane potential are monitored with fluorescent membrane potential dye pair, DiSBAC2(3) and CC2-DMPE, using FRET technology.

Cell Maintenance:

HEK293 cells expressing human Nav1.8 channels or human Nav1.5 channels are grown in T225 flasks, in a 5% $CO_2$ humidified incubator to about 80% confluence. Media composition of HEK293 cells expressing human Nav1.8 channels consists of Dulbecco's Modified Eagle Medium (high glucose), 10% fetal calf serum (FCS), 100 units/mL Penicillin, 100 microgram/mL Streptomycin, 200 microgram/mL Zeocin and 500 microgram/mL Geneticine. HEK293 cells expressing human Nav1.5 channels are maintained in Dulbecco's Modified Eagle Medium (high glucose) supplemented with 10% fetal calf serum (FCS), 100 units/mL Penicillin, 100 microgram/mL Streptomycin and 500 microgram/mL Geneticine.

Protocol:

Seed each cell lines ($1.5 \times 10^4$ cells/well) into 384-well plates prior to experimentation.

Incubate at 37° C. in 5% $CO_2$ for 24 hours.

Wash each well with buffer #1 (140 mM NaCl, 4.5 mM KCl, 10 mM D-Glucose, 2 mM $CaCl_2$, 1 mM $MgCl_2$, 10 mM HEPES, pH 7.4 adjusted with. NaOH) twice using plate washer.

Add 1st loading solution containing 7.5 microM CC2-DMPE and 0.06% Pluronic F-127 in buffer #1.

Incubate the plate at rt in dark for 0.5 hours.

Wash each well with buffer #2 (160 mM Choline, 10 mM D-Glucose, 0.1 mM $CaCl_2$, 1 mM $MgCl_2$, 1.0 mM HEPES, pH 7.4 adjusted with KOH) twice using plate washer.

Add 2nd loading solution containing 75 microM DiSBAC2(3), 2.5 mM Xylene Fast Yellow, 10 microM Deltamethrin or 100 microM veratridine and 0.02% Pluronic F-127 in buffer #2.

Add compound solutions into the assay plate and leave the plate for 30 minutes under the dark at rt.

Monitor the fluorescent membrane potentials before and after the addition of buffer #2 by FDSS.

The data is analyzed and reported as normalized ratios of intensities measured in the 465 nm and 575 nm channels. The process of calculating these ratios is performed as follows:

$$FR = (FI465Max/FI575Min) - (FI465B/FI575B) \quad [Math.2]$$

"FR"=fluorescence ratio

"FI465B"=the mean of fluorescence intensity as baseline (before $Na^+$ ligand addition) at 465 nm "FI575B"=the mean of fluorescence intensity as baseline (before $Na^+$ ligand addition) at 575 nm "FI465Max"=maximum fluorescence intensity at 465 nm after $Na^+$ stimulation "FI575Min"=minimum fluorescence intensity at 575 nm after $Na^+$ stimulation $$\text{Inhibition (\%)} = 100 - \frac{(FR \text{ of each well}) - (\text{median } FR \text{ in positive controls})}{(\text{median } FR \text{ in negative controls}) - (\text{median } FR \text{ in positive controls})} \times 100 \quad [Math.3]$$

This analysis is performed using a computerized specific program designed for FDSS generated data. Fluorescence ratio values are plotted using XLfit to determine an $IC_{50}$ value for each compound.

All tested compounds of Examples show less than about 5 microM of $IC_{50}$ against Nav1.7 and/or Nav1.8 in the above assays. Preferable compounds show less than about 3 microM of $IC_{50}$ against Nav1.7 and/or Nav1.8 in the above assays.

Compound of Example 1 is 0.65 microM of $IC_{50}$ against Nav1.8.

Regarding all tested compounds, the ratio of activities against Nav1.5 vs. Nav1.7 or Nav1.8 is more than three times. For example, the activities of Example 1 against Nav1.5 and Nav1.8 are more than 30 microM and 0.65 microM, respectively.

Electrophysiology Assay

Whole cell patch clamp recording is used to assess the efficacy or selectivity of Na channel blocker on human voltage gated sodium channels. Na channel expressing cells are dissociated by 0.05% Trypsine-EDTA or Accutase, and then seeded on cover glass for 2-24 hrs.

Manual patch clamp recordings are conducted at rt using the voltage-clamp amplifier (Axon Instruments or HEKA electronik). Electrodes are pulled with P-97 electrode puller (Sutter Instrument). The electrode resistances are 1-3 MOhm when intracellular solution is filled. Currents are lowpass filtered between 2-5 kHz and digitally sampled at 10 kHz.

The extracellular and intercellular solutions for human Nav1.7 and Nav1.5 consist of the following composition:

Extracellular recording solution (mM): 135 NaCl, 5 KCl, 2 $CaCl_2$, 1 $MgCl_2$, 10 HEPES, and 10 Glucose, pH 7.4 adjusted with NaOH; and Intercellular solution (mM): 120 CsF, 15 NaCl, 10 EGTA, and 10 HEPES, pH 7.2 adjusted with CsOH.

The extracellular and intercellular solutions for human Nav1.8 consist of the following composition:

Extracellular recording solution (mM): 160 NaCl, 1 KCl, 2 $CaCl_2$, 1 $MgCl_2$, 10 HEPES, and 10 Glucose, pH 7.4 adjusted with NaOH; and Intercellular solution (mM): 120 CsF, 30 CsCl, 1 NaCl, 10 EGTA, and 10 HEPES, pH 7.2 adjusted with CsOH.

Two Pulse Protocol

After whole-cell configuration is achieved, cell is monitored at least 10 minutes to allow cell dialysis with pipette solution. To evaluate of inhibitory effects of test compounds, the cells are clamped at −100 or −120 mV. First test pulse to 0 mV (Test 1 pulse) is applied following conditioning pulse for 8 sec, at which approximately 50% channels are inactivated, followed by 10 or 20 msec recovery period at −100 or −120 mV and second pulse to 0 mV (Test 2 pulse). Command pulses are delivered at interval of 30 sec. Test compound solutions are consecutively applied.

Peak currents evoked by Test 1 and Test 2 pulses are sampled with Clampex (Axon Instruments) or Pulse+Pulse Fit (HEKA). Averaged peak currents under vehicle or test compounds are calculated from 3 data points at end of each condition. Inhibitory effect (% inhibition) of test compound is calculated as bellow;

$$\% \text{ inhibition} = [1 - \text{Averaged peak current (Compound)}/\text{Averaged peak current (Vehicle)}] \times 100 \quad [Math.4]$$

Inhibitory effects (% inhibition) on peak currents at Test 1 or Test 2 pulse are plotted against test concentration and $IC_{50}$ values at Test 1 (Closed $IC_{50}$) or Test 2 (Inactivated $IC_{50}$) are calculated with Hill equation, respectively. Data analyses are performed using XLfit (Version 5.2.0.0.).

Use-Dependent Inhibition of Test Compounds

After whole-cell configuration is achieved, the cell is monitored at least 10-15 min to allow cell dialysis with pipette solution. The cells are hold at membrane potential at which approximately 10 to 20% channels are inactivated. Test pulses of 0 mV with 10 msec duration are applied at 10 Hz for 100 times in the absence or presence test compounds. Data acquisition is implemented with Clampex (Axon Instruments) or Pulse+Pulse Fit (HEKA) programs.

Use-dependent activities of test compound are shown as "Tonic inhibition" and "Phasic inhibition".

Tonic inhibition is calculated by following equation:

$$\text{Tonic inhibition (\%)} = (1 - I_{100th/cpd}/I_{100th/control}) \times 100\% \quad [\text{Math.6}]$$

where $I_{1st/control}$ and $I_{100th/cpd}$ are the peak current amplitude elicited by $1^{st}$ pulse in vehicle control and in the presence of test compound, respectively.

Phasic inhibition is defined as total current reduction in the presence of test compound during repetitive pulse application and calculated by following equation:

$$\text{Phasic inhibition (\%)} = (1 - I_{100thcpd}/I_{100th/control}) \times 100\% \quad [\text{Math.6}]$$

where $I_{100th/control}$ and $I_{100th/cpd}$ are the peak current amplitude elicited by 100th pulse in vehicle control and in the presence of test compound, respectively.

Estimated $IC_{50}$ (Est. $IC_{50}$) is calculated by following equation assuming that compounds interact with Na channels via a conventional 1:1 binding model.

$$\text{Estimated } IC_{50} = (100/\% \text{ inhibition} - 1) \times [\text{test dose}] \quad [\text{Math.7}]$$

Affinity to Resting State ($K_r$) and Inactivated State (K) of Test Compound

The normalized steady-state inactivation curve is constructed using 2 sec (for vehicle) or 60 sec (for drugs) conditioning pulse to different potentials followed immediately by the test pulse to −10 mV. Peak currents are plotted as fraction of the maximum current at the conditioning potentials ranging from −120 mV to 0 mV for Nav1.7. V1/2 and k values are estimated from Boltzmann fits. The affinity of test compound to resting state of Na channels ($K_{resting}$ or $K_r$) is assessed by depolarizing test pulse from a negative holding potential of −130 mV, where virtually all channels are in the resting state. $K_r$ value is calculated by a conventional 1:1 binding model:

$$K_{resting}(K_r) = \{[\text{drug}]I_{max},\text{drug}/(I_{max}, \text{control} - I_{max}, \text{drug})\} \quad [\text{Math.8}]$$

where $K_{resting}$ (=$K_r$) is a dissociation constant for the resting state and [drug] is compound concentration. $I_{max}$,control and $I_{max}$,drug are peak currents in the absence and presence of compound, respectively.

The affinity of test compound to inactivated state of Na channels ($K_{inact}$ or $K_i$) is estimated from the compound induced leftward shift of the steady-state inactivation curve. Interaction of the compound with the channel on inactivated state is evaluated by the following equation:

$$K_{inact}(K_i) = \{[\text{drug}]/((1+[\text{drug}]/Kr)^* \exp(-\Delta V/k) - 1)\} \quad [\text{Math.9}]$$

where $K_{inact}$ (=$K_i$) is a dissociation constant for the inactivated state. $\Delta V$ is the compound-induced voltage shift of half maximal voltage of Boltzmann curve and k is the slop factor on presense of compound.

Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier (Axon Instruments or HEKA electronik). The extracellular recording solution consists of (mM): 140 NaCl, 5 KCl, 2 $CaCl_2$, 1 $MgCl_2$, 10 HEPES, and 10 Glucose, pH 7.4 adjusted with NaOH. The internal solution consists of (mM): 120 CsF, 15 NaCl, 10 EGTA, and 10 HEPES, pH 7.2 adjusted with CsOH; Upon insertion of the pipette tip into the bath, the pipette resistance is noted (acceptable range is between 1-3 megaohm). The junction potential between the pipette and bath solutions is zeroed on the amplifier. After establishing the whole-cell configuration, approximately 10 minutes are allowed for the pipette solution to equilibrate within the cell before beginning recording. Currents are lowpass filtered between 2-5 kHz and digitally sampled at 10 kHz.

The normalized steady-state inactivation curve is constructed using 2 sec (for vehicle) or 60 sec (for drugs) conditioning pulse to different potentials followed immediately by the test pulse to −10 mV. Peak currents are plotted as fraction of the maximum current at the conditioning potentials ranging from −120 mV to −40 mV for Nav1.3 and from −130 mV to −60 mV for Nav1.7. V1/2 or k values are estimated from Boltzmann fits. The affinity of drugs to resting state of Na channels ($K_{resting}$ or $K_r$) is assessed by 30 msec test pulse from a negative holding potential of −120 or −130 mV, where virtually all channels are in the resting state. $K_r$ value is calculated by a conventional 1:1 binding model:

$$K_{resting}(K_r) = \{[\text{drug}]I_{max},\text{drug}/(I_{max}, \text{control} - I_{max}, \text{drug})\} \quad [\text{Math.10}]$$

where $K_{resting}$ (=$K_r$) is a dissociation constant for the resting state and [drug] is compound concentration. $I_{max}$,control and $I_{max}$,drug are peak currents in the absence and presence of compound, respectively.

The affinity of drug to inactivated state of Na channels ($K_{inact}$ or $K_i$) is estimated from the shift of the availability curve by compound. Interaction of the compound with the channel on inactivated state is evaluated by the following equation:

$$K_{inact}(K_i) = \{[\text{drug}]/((1+[\text{drug}]/Kr)^* \exp(-\Delta V/k) - 1)\} \quad [\text{Math.11}]$$

where $K_{inact}$(=$K_i$) is a dissociation constant for the inactivated state. $\Delta V$ is the compound-induced voltage shift of half maximal voltage of Boltzmann curve and k is the slop factor on presense of compound.

All tested compounds of the invention show potent activities in this model. For example, the activities ($K_i$) of Examples 3 and 4 against Nav1.7 are 0.96 microM and 0.52 microM, respectively.

In Vivo Assay

Chronic Constriction Injury (CCI)-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. CCI-induced static allodynia is assessed by von Frey hair (VFH) test. Surgery is performed according to the method of Bennett G J and Xie Y K (Pain 1988, 33: 87-107). The animals are anesthetized with intraperitoneal injection of pentobarbital sodium. The left common sciatic nerve is exposed at the level of the middle of the thigh, freed of adhering tissue, and four ligatures are loosely tided around it by using 4-0 silk thread. The incision is sutured, and the rats are allowed to recover in their cages with soft bedding. Sham operation is performed in the same manner except of sciatic nerve ligation.

The animals are individually placed in a Plexiglas test chamber on an elevated grid to acclimate before the day of testing. On postoperative day (POD) 14-28, evaluation is performed using a series of calibrated VFH (Semmes-Winstein monofilaments) with 0.4, 0.6, 1, 2, 4, 6, 8 and 15 g force. VFH starting with the 2 g force is applied in an ascending or descending fashion according to a modified Dixon up-down method described by Chaplan S R et al. (J Neurosci Methods 1994, 53: 55-63). Each VFH is presented to the plantar surface of the operated hind paw with steady upward pressure until bent for approximately 6 seconds. In the absence of a paw withdrawal, a stronger stimulus is presented. In the event of a paw withdrawal, the next weaker stimulus is chosen. After the initial change from positive to negative or vice versa 4 more stimulations are applied. The 6-score pattern of positive and negative responses is converted into a 50% paw withdrawal threshold (PWT) using the following formula:

$$50\% \text{ PWT } (g) = (10^{[Xf+\kappa\delta]})/10{,}000 \quad [\text{Math.12}]$$

where $Xf$ is the value (in log units) of the final VFH used, $\kappa$ is the tabular value for the pattern of positive/negative responses and $\delta$ is the mean difference between stimuli in log units (here, 0.224).

In the cases where continuous positive or negative responses are observed all the way out to the end of the stimulus spectrum, values of 0.25 and 15 g are assigned, respectively. The animals showing static allodynia (<4 g of 50% PWT) by CCI surgery are selected for evaluation and randomized to be nearly equal mean 50% PWT across all groups. The compounds of the invention or their vehicles are administered systemically. The rats are habituated to the chamber for at least 20 minutes before the measurement. The 50% PWT is measured at the appropriated time after compound administration. Statistical analysis is performed by unpaired t-test or one-way analysis of variance (ANOVA) with Dunnett's post-hoc test compared to the vehicle group.

All tested compounds of the, invention show potent activities in this model.

Complete Freund's Adjuvant (CFA)-Induced Thermal Hyperalgesia in Rats

Male Sprague-Dawley rats at 6 weeks old are purchased from Charles River Japan Inc., and housed in groups of two per cage under a 12-h light/dark cycle (lights on at 07:00) with access to food and water ad libitum. CFA-induced thermal hyperalgesia is assessed using the plantar test apparatus (Ugo Basile) as described by Hargreaves K et al. (Pain 1988, 32: 77-88). The animals are placed in an apparatus consisting of individual testing box on an elevated glass table and allowed to acclimate for at least 10 minutes. Following the habituation, a mobile radiant heat source is located under the table and heat stimulation is applied to the plantar surface of the right hind paw. The latency to remove its hind paw is defined as paw withdrawal latency (PWL) in sec. The cut-off point is set at 30 seconds to prevent tissue damage. CFA is prepared at a concentration of 2-3 mg/mL of *Mycobacterium tuberculosis* H37 RA in liquid paraffin. After disinfections with 70% ethanol, the rats are injected intraplantarly with 100 microL of CFA (200-300 microgram) into the right hind paw. Two days after CFA injection, PWL is measured in the same manner as mentioned above. The animals showing decrease of the PWL (hyperalgesia) by CFA injection are selected for evaluation and randomized to be nearly equal mean PWL across all groups. The compounds of the invention or their vehicles are administered systemically. The rats are habituated to the apparatus for at least 10 minutes before each measurement. The PWL is measured at the appropriated time after compound administration. Statistical analysis is performed by unpaired t-test or ANOVA with Dunnett's post-hoc test compared to the vehicle group.

All tested compounds of the invention show potent activities in this model.

CFA-Induced Weight Bearing Deficit in Rats

Male Sprague-Dawley rats at 7 weeks old are purchased from Charles River Japan Inc., and housed in groups of two per cage under a 12-h light/dark cycle (lights on at 07:00) with access to food and water ad libitum. CFA-induced weight bearing (WB) deficit is assessed using Incapacitance tester (Linton Instrumentation). The animals are habituated to a plastic ease that comes with Incapacitance tester before the day of CFA injection. On the day of CFA injection, the weight distribution of each hind paw is measured 3 times per rat using the tester, and the difference of weight distribution, weight on the right (injected) paw minus weight on left (non-injected) paw, is defined as WB deficit value in g. The duration of the each measurement is adjusted to 3 seconds. CFA is prepared at a concentration of 2-3 mg/mL of *Mycobacterium tuberculosis*. H37 RA in liquid paraffin. After disinfections with 70% ethanol, the rats are injected intraplantarly with 100 microL of CFA (200-300 microgram) into the right hind paw. Two days after CFA injection, the weight distribution of each hind paw is measured and the WB deficit value is calculated in the same manner as mentioned above. The animals showing decrease of the WB deficit (>30%) by CFA injection are selected for evaluation and randomized to be nearly equal across all groups. The compounds of the invention or their vehicles are administered systemically. The weight distribution of each hind paw is measured at the appropriated time after compound administration, and the WB deficit value is calculated as previously explained. Statistical analysis is performed by unpaired t-test or ANOVA with Dunnett's post-hoc test compared to the vehicle group.

All tested compounds of the invention show potent activities in this model.

Paw Incision-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. Paw incision-induced static allodynia is assessed by VFH test. Surgery is performed according to the procedure described by Brennan et al. (Pain 1996, 64: 493-501). The animals are initially anesthetized with 3-4% isoflurane/$O_2$ mixture in an anesthetic chamber and maintained with 2-3% delivered through a nose cone. The plantar surface of the right hind paw is sterilized with 7.5% povidone-iodine solution. A 1-cm longitudinal incision is made with a number 11 blade, through skin and fascia of the plantar aspect of the paw, starting 0.5 cm from the proximal edge of the heel and extending toward the toes. The plantaris muscle is elevated using forceps and retracted. The muscle origin and insertion remain intact. After hemostasis with gentle pressure, the skin is apposed with 2 sutures of 5-0 nylon. The wound site is covered with Terramycin ointment, and the rats are allowed to recover in their cages with soft bedding. The animals are individually placed in a Plexiglas test chamber on an elevated grid to acclimate for 1 hour before the day of surgery. On POD1, evaluation is performed using a series of calibrated VFH (0.008, 0.02, 0.04, 0.07, 0.16, 0.4, 0.6, 1, 1.4, 2, 4, 6, 8, 10, 15 and 26 g). Starting with the 0.16 g force in an ascending or descending fashion, each VFH is presented to the proximal end of the wound near the lateral heel with steady upward pressure until bent for approximately 6 seconds. In the absence of a paw withdrawal (negative response), a stronger stimulus is presented. In the event of a paw withdrawal (positive response), the next weaker stimulus is chosen. The lowest amount of force required to elicit two positive responses is defined as PWT in g. In the cases where continuous positive or negative responses are observed all the way out to the end of the stimulus spectrum, values of 0.008 and 26 g are assigned, respectively. The animals showing <1.4 g of PWT by incisional surgery are selected for evaluation and randomized to be nearly equal median PWT across all groups. The compounds of the invention or their vehicles are administered systemically. The rats are habituated to the chamber for at least 20 minutes before the measurement. The PWT is measured at the appropriated time after compound administration. Statistical analysis is performed by Mann-Whitney U-test or Kruskal-Wallis with Dunn's post-hoc test compared to the vehicle group.

All tested compounds of the invention show potent activities in this model.

Paclitaxel-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. Paclitaxel-induced static allodynia is assessed by VFH test. Treatment of paclitaxel is performed according to the method of Polomano R C et al. (Pain 2001, 94: 293-304). Paclitaxel (2 mg) is injected intraperitoneally on four alternate days (Days 1, 3, 5 and 7) in a volume of 1 mL/kg. Cumulative dose is 8 mg/kg. In sham group, the vehicle (a mixture of 16.7% Cremophor EL and 163% ethanol in saline) is treated as the same schedule. The animals are individually placed in a Plexiglas test chamber on an elevated grid to acclimate before the day of testing. On Days 15-29, evaluation is performed using a series of calibrated VFH with 0.4, 0.6, 1, 2, 4, 6, 8 and 15 g force. VFH starting with the 2 g force is applied in an ascending or descending fashion according to a modified Dixon up-down method described by Chaplan S R et al. (J Neurosci Methods 1994, 53: 55-63). Each VFH is presented to the plantar surface of the operated hind paw with steady upward pressure until bent for approximately 6 seconds. In the absence of a paw withdrawal, a stronger stimulus is presented. In the event of a paw withdrawal, the next weaker stimulus is chosen. After the initial change from positive to negative or vice versa 4 more stimulations are applied. The 6-score pattern of positive and negative responses is converted into a 50% PWT using the following formula:

$$50\% \text{ PWT } (g) = (10^{[Xf + \kappa\delta]})/10{,}000 \qquad [\text{Math.13}]$$

where Xf is the value (in log units) of the final VFH used, κ is the tabular value for the pattern of positive/negative responses and δ is the mean difference between stimuli in log units (here, 0.224).

In the cases where continuous positive or negative responses are observed all the way out to the end of the stimulus spectrum, values of 0.25 and 15 g are assigned, respectively. The animals showing static allodynia (<4 g of 50% PWT) by paclitaxel treatment are selected for evaluation and randomized to be nearly equal mean 50% PWT across all groups. The compounds of the invention or their vehicles are administered systemically. The rats are habituated to the chamber for at least 20 minutes before the measurement. The 50% PWT is measured at the appropriated time after compound administration. Statistical analysis is performed by unpaired t-test or ANOVA with Dunnett's post-hoc test compared to the vehicle group.

All tested compounds of the invention show potent activities in this model.

Formalin-Induced Nociceptive Behaviors in Rats

Male Sprague-Dawley rats at 6 weeks old are purchased from Charles River Japan Inc., and housed in groups of two per cage under a 12-h light/dark cycle (lights on at 07:00) with access to food and water ad libitum. Formalin test is performed during the light cycle. The animals are acclimated to the testing chamber for at least 30 minutes prior to formalin injection. A mirror is placed behind and/or under the chamber to aid observation. The 50 microL of 5% formalin solution is injected subcutaneously into the plantar surface of the right hind paw. Immediately after the injection, the rats are individually placed in the chamber, and the pain-related behaviors are recorded. After the testing, the time spent licking and/or biting of the injected paw are counted in 5-minutes bins for 45 minutes following the formalin treatment. The sum of time spent licking/biting in seconds from time 0 to 5 minutes is considered as the early phase, whereas the late phase is taken as the sum of time spent licking/biting typically from 15 to 45 minutes. The compounds of the invention or their vehicles are administered systemically at the appropriated time point before the formalin injection. Statistical analysis is performed by unpaired t-test or ANOVA with Dunnett's post-hoc test compared to the vehicle group.

All tested compounds of the invention show potent activities in this model.

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centrifuged at 48,000×g at 4° C. for 20 min. The pellets are then resuspended, homogenized, and centrifuged once more in the same manner. The final pellets are resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at rt. Nonspecific binding is determined by 10 microM E4031 at the final concentration.

All tested compounds of the invention show higher $IC_{50}$ values in human dofetilide binding than $IC_{50}$ values in Nav1.7 or Nav1.8 FRET Assay. The high $IC_{50}$ values in human dofetilide binding activities lead to reducing the risk of cardiovascular adverse events.

Metabolic Stability Assay:

Half-Life in Human Liver Microsomes (HLM)

Test compounds (1 microM) are incubated with 3.3 mM $MgCl_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 and a P450 group. Nicotinamide adenine dinucleotide phosphate (NADPH) is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations:

Half-life=ln 2/$k$ [Math.14]

The compounds of this invention show preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam(ULTRAFINE UC-429) 2 microM) at 3 microM of the each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM MgCl$_2$ and probes as substrate for 5 min. Reaction is started by adding a 20 microL of 10 mM NADPH (20 microL of NADPH generating system, which consist of 10 mM NADP$^+$, 50 mM DL-Isocitric acid and 10 U/mL Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug-drug interaction is interpreted based on generation % of metabolites in the presence or absence of test compound.

The compounds of this invention show preferable results, which show the above-mentioned practical use.

Plasma Protein Binding Assay

Plasma protein binding of the test compound (1 microM) is measured by the method of equilibrium dialysis using 96-well plate type equipment. HTD96a (registered trademark), regenerated cellulose membranes (molecular weight cut-off 12,000-14,000, 22 mm×120 mm) are soaked for overnight in distilled water, then for 15 minutes in 30% ethanol, and finally for 20 minutes in dialysis buffer (Dulbecco's phosphate buffered saline, pH7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile containing internal standard compounds for analysis. The concentration of the compound is determined with LC/NIS/MS analysis.

The fraction of the compound unbound is calculated by the following equation (A) or (B):

(A) $fu=1-\{([plasma]_{eq}-[buffer]_{eq})/([plasma]_{eq})\}$ [Math.15]

wherein [plasma]$_{eq}$ and [buffer]$_{eq}$ are the concentrations of the compound in plasma and buffer, respectively.

[Math. 16]

$$fu(\%) = \frac{Cb/Cis, b \times 4}{Cp/Cis, p \times 4/3} \times 100 \quad (B)$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively.

The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate iso-pore membrane. The concentration of samples is determined by a general gradient HPLC method (J. Pharm. Sci. 2006, 95, 2115-2122).

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

INDUSTRIAL APPLICABILITY

The amide derivatives of the present invention are useful in the treatment of a wide range of disorders in which Nav1.7 and/or Nav1.8 channel blockers are involved, particularly pain, acute pain, chronic pain, neuropathic pain, inflammatory pain, visceral pain, nociceptive pain, pruritus, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, back pain, head or neck pain, severe or intractable pain, breakthrough pain, postsurgical pain, stroke, cancer pain, seizure disorder, causalgia, and chemo-induced pain.

The invention claimed is:

1. A compound of the following formula (I):

$$[R^2]_p \text{-A-X-C}(R^{5a})(R^{5b})\text{-C}(R^{5c})(R^{5d})\text{-NH-C(=O)-[pyridyl with } [R^3]_q, Z]\text{-NH-C(=O)-R}^4 \quad (I)$$

wherein:

A is aryl or heteroaryl;

$R^1$ is selected from the group consisting of: —$CF_3$, —$CHF_2$, —$OCF_3$, —$SF_5$, —$OCHF_2$, —$OCH_2CHF_2$, —$OCH_2CF_3$, —$OCH_2CH_2CF_3$, —$OCH(CH_3)CF_3$, —$OCH_2C(CH_3)F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, —$OCH_2CH_2OCF_3$, and fluorobenzyloxy;

$R^2$ is independently selected from the group consisting of: (1) hydrogen, (2) halogen, (3) hydroxyl, (4) $C_{1-6}$ alkyl, (5) —O—$C_{1-6}$ alkyl, (6) $C_{2-6}$ alkenyl, (7) $C_{3-7}$ cycloalkyl, (8) —CN, and (9) —(C=O)—$NR^6R^7$, wherein the $C_{1-6}$ alkyl, the —O—$C_{1-6}$ alkyl, the $C_{2-6}$ alkenyl or $C_{3-7}$ cycloalkyl is unsubstituted or substituted with one or more substituents independently selected from the group consisting of: halogen and hydroxyl;

$R^1$ and $R^2$ may be the same or different;

p is 0, 1, 2, 3 or 4;

when p is two or more, each $R^2$ is the same or different;

$R^1$ and $R^2$ may be substituted anywhere on the A ring;

X is selected from the group consisting of: —$CR^{8a}R^{8b}$—, —O—, —O—$CR^{8a}R^{8b}$—, —$NR^9$—, —$NR^9$—$CR^{8a}R^{8b}$—, —S—, and —S—$CR^{8a}R^{8b}$—;

Z is CH, $CR^3$, or N;

$R^3$ is independently selected from the group consisting of: (1) hydrogen, (2) halogen, (3) hydroxyl, (4) $C_{1-6}$ alkyl, and (5) —O—$C_{1-6}$ alkyl;

q is 0, 1, 2, or 3; when q is two or more, each $R^3$ is the same or different;

$R^4$ is selected from the group consisting of:
(1) hydrogen, (2) $C_{1-6}$ alkyl, (3) $C_{2-6}$ alkenyl, (4) $C_{3-7}$ cycloalkyl, wherein the $C_{1-6}$ alkyl, the $C_{2-6}$ alkenyl or the $C_{3-7}$ cycloalkyl is unsubstituted or substituted with one or more substituents independently selected form the group consisting of: halogen, hydroxyl, —$C_{1-6}$ alkyl, —O—$C_{1-6}$ alkyl, and $C_{3-7}$ cycloalkyl, and (5) aryl which is unsubstituted or substituted with one or more substituents independently selected from the group consisting of: halogen, hydroxyl, $C_{1-6}$ alkyl, —O—$C_{1-6}$ alkyl, —$C_{3-7}$ cycloalkyl, and —O—$C_{3-7}$ cycloalkyl;

$R^{5a}$ and $R^{5c}$ are independently selected from the group consisting of: (1) hydrogen, (2) halogen, (3) hydroxyl, (4) $C_{1-6}$ alkyl, (5) —O—$C_{1-6}$ alkyl, and (6) $C_{1-6}$ alkoxy$C_{1-6}$ alkyl, wherein the $C_{1-6}$ alkyl, the —O—$C_{1-6}$ alkyl, and the $C_{1-6}$ alkoxy$C_{1-6}$ alkyl is unsubstituted or substituted with one or more substituents independently selected from the group consisting of: halogen and hydroxyl;

$R^{5b}$ and $R^{5d}$ are independently selected from the group consisting of: (1) hydrogen, (2) halogen, and (3) $C_{1-6}$ alkyl;

$R^{5a}$ may form a $C_{3-6}$ cycloalkyl with $R^{5b}$;

$R^{5c}$ may form a $C_{3-6}$ cycloalkyl with $R^{5d}$;

$R^6$ and $R^7$ are independently selected from the group consisting of: (1) hydrogen, (2) $C_{1-6}$ alkyl, and (3) $C_{1-6}$ alkoxy$C_{1-6}$ alkyl, wherein the $C_{1-6}$ alkyl or the $C_{1-6}$ alkoxy$C_{1-6}$ alkyl is unsubstituted or substituted with one or more substituents independently selected from the group consisting of: halogen and hydroxyl;

$R^6$ may form a 4 to 7 membered ring with $R^7$ which may contain a nitrogen atom, an oxygen atom, a sulfur atom, or a double bond;

$R^{8a}$ and $R^{8b}$ are independently selected from the group consisting of:
(1) hydrogen, (2) halogen, (3) hydroxyl, (4) C1-6 alkyl, and (5) -0-C1-6 alkyl; and $R^9$ is selected from the group consisting of: (1) hydrogen and (2) $C_{1-6}$ alkyl; or a pharmaceutically acceptable salt thereof.

2. The compound described in claim 1 wherein:

A is phenyl, pyridyl, pyrazyl, pyrimidyl, quinolyl, isoquinolyl, quinoxalyl, or naphthyl;

X is selected from the group consisting of: —$CR^{8a}R^{8b}$—, —O—, —O—$CR^{8a}R^{8b}$—, —$NR^9$—, —$NR^9$—$CR^{8a}R^{8b}$—, and —S—;

$R^{5a}$ and $R^{5c}$ are independently selected from the group consisting of:
(1) hydrogen, (2) halogen, (3) hydroxyl, and (4) $C_{1-6}$ alkyl, wherein the $C_{1-6}$ alkyl is unsubstituted or substituted with one or more substituents independently selected from the group consisting of: halogen and hydroxyl;

$R^{5b}$ is hydrogen;

$R^{5d}$ is selected from the group consisting of: (1) hydrogen, (2) halogen, and (3) $C_{1-6}$ alkyl; and $R^{5c}$ may form a $C_{3-6}$ cycloalkyl with $R^{5d}$;

or a pharmaceutically acceptable salt thereof.

3. The compound described in claim 1, wherein the compound of the formula (I) is represented by a compound of the following formula (II):

$$\text{(II)}$$

wherein:

W is CH, $CR^1$, $CR^2$ or N;

$R^1$ is selected from the group consisting of: —$CF_3$, —$CHF_2$, —$OCF_3$, —$SF_5$, —$OCH_2CF_3$, and fluorobenzyloxy;

$R^2$ is selected from the group consisting of: (1) hydrogen, (2) halogen, (3) hydroxyl, (4) $C_{1-6}$ alkyl, (5) —$OC_{1-6}$ alkyl, and (8) —CN;

X is selected from the group consisting of: C—$R^{8a}R^{8b}$—, —O—, —O—$CR^{8a}R^{8b}$—, —$NR^9$—, —$NR^9$—$CR^{8a}R^{8b}$—, and —S—;

Z is CH, $CR^3$, or N;

$R^3$ is selected from the group consisting of:
(1) hydrogen, (2) halogen, (3) hydroxyl, (4) $C_{1-6}$ alkyl, and (5) —O—$C_{1-6}$ alkyl;

$R^4$ is selected from the group consisting of: (1) C1-6 alkyl, and (2) C3-7 cycloalkyl, wherein the $C_{1-6}$ alkyl or the $C_{3-7}$ cycloalkyl is unsubstituted or substituted with one or more substituents independently selected form the group consisting of: halogen, hydroxyl, —$C_{1-6}$ alkyl, —O—$C_{1-6}$ alkyl, and $C_{3-7}$ cycloalkyl;

$R^{5a}$ and $R^{5c}$ are independently selected from the group consisting of: (1) hydrogen, (2) halogen, (3) hydroxyl, and (4) $C_{1-6}$ alkyl which is unsubstituted or substituted with one or more substituents independently selected from the group consisting of: halogen and hydroxyl;

$R^{5b}$ is hydrogen;

$R^{5d}$ is selected from the group consisting of: (1) hydrogen, (2) halogen, and (3) $C_{1-6}$ alkyl;

$R^{5c}$ may form a $C_{3-6}$ cycloalkyl with $R^{5d}$;

$R^{8a}$ and $R^{8b}$ are independently selected from the group consisting of:

(1) hydrogen, (2) halogen, (3) hydroxyl, (4) $C_{1-6}$ alkyl, and (5) —O—$C_{1-6}$ alkyl; and $R^9$ is selected from the group consisting of: (1) hydrogen and (2) $C_{1-6}$ alkyl;

or a pharmaceutically acceptable salt thereof.

4. The compound described in claim 1, wherein the compound of the formula (I) is represented by a compound of the following formula (III):

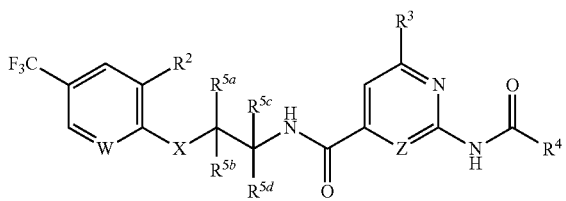

wherein:

W is CH or N;

$R^2$ is selected from the group consisting of: (1) hydrogen, (2) halogen, (3) hydroxyl, (4) $C_{1-6}$ alkyl, (5) —O—$C_{1-6}$ alkyl, and (6) —CN;

X is selected from the group consisting of: —$CR^{8a}R^{8b}$—, —O—, —O—$CR^{8a}R^{8b}$—, —$NR^9$—, —$NR^9$—$CR^{8a}R^{8b}$—, and —S—;

Z is CH or N;

$R^3$ is selected from the group consisting of:

(1) hydrogen, (2) halogen, (3) hydroxyl, (4) $C_{1-6}$ alkyl, and (5) —O—$C_{1-6}$ alkyl;

$R^4$ is selected from the group consisting of: (1) $C_{1-6}$ alkyl and (2) $C_{3-7}$ cycloalkyl, wherein the $C_{1-6}$ alkyl or the $C_{3-7}$ cycloalkyl is unsubstituted or substituted with one or more substituents independently selected form the group consisting of: halogen and hydroxyl;

$R^{5a}$ and $R^{5c}$ are independently selected from the group consisting of: (1) hydrogen, (2) halogen, (3) hydroxyl, and (4) $C_{1-6}$ alkyl which is unsubstituted or substituted with one or more substituents independently selected from the group consisting of: halogen and hydroxyl;

$R^{5b}$ and $R^{5d}$ are hydrogen;

$R^{8a}$ and $R^{8b}$ are hydrogen; and $R^9$ is hydrogen;

or a pharmaceutically acceptable salt thereof.

5. The compound described in claim 4 wherein:

W is N;

or a pharmaceutically acceptable salt thereof.

6. The compound described in claim 1, which is selected from the group consisting of:

2-(cyclopropanecarboxamido)-N-(2-(4-(trifluoromethyl)phenoxy)propyl)isonicotinamide;
2-acetamido-N-(2-((3-chloro-5-(trifluoromethyl)pyridin-2-yl)amino)ethyl)isonicotinamide;
N-(2-((3-chloro-5-(trifluoromethyl)pyridin-2-yl)amino)ethyl)-2-propionamidoisonicotinamide;
2-acetamido-N-(2-((3-chloro-5-(trifluoromethyl)pyridin-2-yl)amino)ethyl)-6-methylisonicotinamide;
N-(2-((3-chloro-5-(trifluoromethyl)pyridin-2-yl)amino)ethyl)-2-methyl-6-propionamidoisonicotinamide;
N-(2-((3-chloro-5-(trifluoromethyl)pyridin-2-yl)amino)ethyl)-2-(cyclopropanecarboxamido)isonicotinamide;
N-(2-((3-chloro-5-(trifluoromethyl)pyridin-2-yl)amino)ethyl)-2-isobutyramidoisonicotinamide;
2-acetamido-N-(2-((3-chloro-5-(trifluoromethyl)pyridin-2-yl)oxy)ethyl)isonicotinamide;
N-(2-((3-chloro-5-(trifluoromethyl)pyridin-2-yl)oxy)ethyl)-2-propionamidoisonicotinamide;
2-acetamido-N-(2-((3-chloro-5-(trifluoromethyl)pyridin-2-yl)oxy)ethyl)-6-methylisonicotinamide;
2-acetamido-N-(2-((3-chloro-5-(trifluoromethyl)pyridin-2-yl)oxy)ethyl)-6-methylpyrimidine-4-carboxamide;
2-methyl-6-propionamido-N-(2-((5-(trifluoromethyl)pyridin-2-yl)oxy)ethyl)isonicotinamide;
N-(2-((3-chloro-5-(trifluoromethyl)pyridin-2-yl)oxy)ethyl)-2-isobutyramidoisonicotinamide;
N-(2-((3-chloro-5-(trifluoromethyl)pyridin-2-yl)oxy)ethyl)-2-(cyclopropanecarboxamido)isonicotinamide;
N-(2-((3-chloro-5-(trifluoromethyl)pyridin-2-yl)oxy)ethyl)-2-methyl-6-propionamidoisonicotinamide;
N-(2-((3-chloro-5-(trifluoromethyl)pyridin-2-yl)oxy)ethyl)-2-(cyclopropanecarboxamido)-6-methylpyrimidine-4-carboxamide;
(R)—N-(2-((3-chloro-5-(trifluoromethyl)pyridin-2-yl)oxy)propyl)-2-isobutyramidoisonicotinamide;
2-isobutyramido-N-(2-(3-(trifluoromethoxy)phenoxy)ethyl)isonicotinamide;
2-acetamido-6-methyl-N-(2-(3-(trifluoromethoxy)phenoxy)ethyl)isonicotinamide;
2-acetamido-N-(2-(2-chloro-4-(trifluoromethyl)phenoxy)ethyl)isonicotinamide;
N-(2-(2-chloro-4-(trifluoromethyl)phenoxy)ethyl)-2-propionamidoisonicotinamide;
N-(2-(2-chloro-4-(trifluoromethyl)phenoxy)ethyl)-2-isobutyramidoisonicotinamide;
2-acetamido-N-(2-(2-chloro-4-(trifluoromethyl)phenoxy)ethyl)-6-methylisonicotinamide;
2-acetamido-6-methyl-N-(2-(4-(trifluoromethyl)phenoxy)ethyl)isonicotinamide;
N-(2-((3-chloro-5-(trifluoromethyl)pyridin-2-yl)oxy)ethyl)-2-(cyclopropanecarboxamido)-6-methylisonicotinamide;
N-(2-((3-chloro-5-(trifluoromethyl)pyridin-2-yl)amino)ethyl)-2-(cyclopropanecarboxamido)-6-methylisonicotinamide;
N-(3-(3-chloro-5-(trifluoromethyl)pyridin-2-yl)propyl)-2-(cyclopropanecarboxamido)isonicotinamide;
2-acetamido-N-(3-(3-chloro-5-(trifluoromethyl)pyridin-2-yl)propyl)-6-methylisonicotinamide;
N-(2-((3-fluoro-5-(trifluoromethyl)pyridin-2-yl)oxy)ethyl)-2-isobutyramido-6-methylisonicotinamide;
N-(3-(3-chloro-5-(trifluoromethyl)pyridin-2-yl)propyl)-2-propionamidoisonicotinamide;
2-acetamido-6-methyl-N-(2-(4-(pentafluorosulfanyl)phenoxy)ethyl)isonicotinamide;
2-propionamido-N-(2-(4-(pentafluorosulfanyl)phenoxy)ethyl)isonicotinamide;

2-(cyclopropanecarboxamido)-N-(2-(4-(pentafluorosulfanyl)phenoxy)ethyl)isonicotinamide;

2-isobutyramido-N-(2-(4-(pentafluorosulfanyl)phenoxy)ethyl)isonicotinamide;

N-(2-((3-chloro-5-(trifluoromethyl)pyridin-2-yl)oxy)ethyl)-2-isobutyramido-6-methylisonicotinamide;

N-(2-((3-chloro-5-(trifluoromethyl)pyridin-2-yl)oxy)ethyl)-2-(cyclopropanecarboxamido)pyrimidine-4-carboxamide;

N-(2-((3-chloro-5-(trifluoromethyl)pyridin-2-yl)amino)ethyl)-2-isobutyramido-6-methylisonicotinamide;

N-(2-((3-chloro-5-(trifluoromethyl)pyridin-2-yl)amino)ethyl)-2-(cyclopropanecarboxamido)pyrimidine-4-carboxamide;

N-(2-(2-chloro-4-(trifluoromethyl)phenoxy)ethyl)-2-methyl-6-propionamidoisonicotinamide;

N-(2-(2-chloro-4-(trifluoromethyl)phenoxy)ethyl)-2-(cyclopropanecarboxamido)isonicotinamide;

N-(2-(2-chloro-4-(trifluoromethyl)phenoxy)ethyl)-2-(cyclopropanecarboxamido)-6-methylisonicotinamide;

N-(2-(2-chloro-4-(trifluoromethyl)phenoxy)ethyl)-2-isobutyramido-6-methylisonicotinamide;

N-(2-(2-chloro-4-(trifluoromethyl)phenoxy)ethyl)-2-(cyclopropanecarboxamido)pyrimidine-4-carboxamide;

2-methyl-6-propionamido-N-(2-((6-(trifluoromethyl)quinolin-2-yl)oxy)ethyl)isonicotinamide;

2-(cyclopropanecarboxamido)-N-(2-((6-(trifluoromethyl)quinolin-2-yl)oxy)ethyl)isonicotinamide;

2-isobutyramido-N-(2-((6-(trifluoromethyl)quinolinyl)oxy)ethyl)isonicotinamide;

2-isobutyramido-N-(2-((6-(trifluoromethyl)quinolin-2-yl)amino)ethyl)isonicotinamide;

2-methyl-6-propionamido-N-(2-((6-(trifluoromethyl)isoquinolin-1-yl)oxy)ethyl)isonicotinamide;

2-methyl-6-propionamido-N-(2-((6-(2,2,2-trifluoroethoxy)naphthalen-2-yl)oxy)ethyl)isonicotinamide;

2-(cyclopropanecarboxamido)-N-(2-((6-(2,2,2-trifluoroethoxy)naphthalen-2-yl)oxy)ethyl)isonicotinamide;

2-isobutyramido-N-(2-((6-(2,2,2-trifluoroethoxy)naphthalen-2-yl)oxy)ethyl)isonicotinamide;

2-acetamido-N-(2-((3-chloro-5-(trifluoromethyl)pyridin-2-yl)thio)ethyl)isonicotinamide;

N-(2-((3-chloro-5-(trifluoromethyl)pyridin-2-yl)thio)ethyl)-2-isobutyramidoisonicotinamide;

2-acetamido-N-(2-((3-chloro-5-(trifluoromethyl)pyridin-2-yl)thio)ethyl)-6-methylisonicotinamide;

N-(2-((3-chloro-5-(trifluoromethyl)pyridin-2-yl)thio)ethyl)-2-methyl-6-propionamidoisonicotinamide;

2-acetamido-N-(2-((6-(trifluoromethyl)quinolin-2-yl)oxy)ethyl)isonicotinamide;

2-propionamido-N-(2-((6-(trifluoromethyl)quinolin-2-yl)oxy)ethyl)isonicotinamide;

2-acetamido-6-methyl-N-(2-((6-(trifluoromethyl)quinolin-2-yl)oxy)ethyl)isonicotinamide;

2-(cyclopropanecarboxamido)-6-methyl-N-(2-((6-(trifluoromethyl)quinolin-2-yl)oxy)ethyl)isonicotinamide;

2-isobutyramido-6-methyl-N-(2-((6-(trifluoromethyl)quinolin-2-yl)oxy)ethyl)isonicotinamide;

2-(cyclopropanecarboxamido)-N-(2-((6-(trifluoromethyl)quinolin-2-yl)oxy)ethyl)pyrimidine-4-carboxamide;

2-(2-hydroxy-2-methylpropanamido)-6-methyl-N-(2-((6-(trifluoromethyl)quinolin-2-yl)oxy)ethyl)isonicotinamide;

(R)-2-acetamido-N-(1-((3-chloro-5-(trifluoromethyl)pyridin-2-yl)oxy)propan-2-yl)isonicotinamide;

(R)—N-(1-((3-chloro-5-(trifluoromethyl)pyridin-2-yl)oxy)propan-2-yl)-2-propionamidoisonicotinamide;

(R)-2-acetamido-N-(1-((3-chloro-5-(trifluoromethyl)pyridin-2-yl)oxy)propan-2-yl)-6-methylisonicotinamide;

(R)—N-(1-((3-chloro-5-(trifluoromethyl)pyridin-2-yl)oxy)propan-2-yl)-2-methyl-6-propionamidoisonicotinamide;

(R)—N-(1-((3-chloro-5-(trifluoromethyl)pyridin-2-yl)oxy)propan-2-yl)-2-(cyclopropanecarboxamido)isonicotinamide;

(R)—N-(1-((3-chloro-5-(trifluoromethyl)pyridin-2-yl)oxy)propan-2-yl)-2-isobutyramidoisonicotinamide;

(R)—N-(1-((3-chloro-5-(trifluoromethyl)pyridin-2-yl)oxy)propan-2-yl)-2-(cyclopropanecarboxamido)-6-methylisonicotinamide;

(R)—N-(1-((3-chloro-5-(trifluoromethyl)pyridin-2-yl)oxy)propan-2-yl)-2-isobutyramido-6-methylisonicotinamide;

(R)—N-(1-((3-chloro-5-(trifluoromethyl)pyridin-2-yl)oxy)propan-2-yl)-2-(cyclopropanecarboxamido)pyrimidine-4-carboxamide;

(S)—N-(2-((3-chloro-5-(trifluoromethyl)pyridin-2-yl)oxy)propyl)-2-methyl-6-propionamidoisonicotinamide;

(R)-2-acetamido-N-(2-((3-chloro-5-(trifluoromethyl)pyridin-2-yl)oxy)propyl)-6-methylisonicotinamide;

(R)—N-(2-((3-chloro-5-(trifluoromethyl)pyridin-2-yl)oxy)propyl)-2-methyl-6-propionamidoisonicotinamide;

(R)—N-(2-((3-chloro-5-(trifluoromethyl)pyridin-2-yl)oxy)propyl)-2-(cyclopropanecarboxamido)isonicotinamide;

(R)—N-(2-((3-chloro-5-(trifluoromethyl)pyridin-2-yl)oxy)propyl)-2-(cyclopropanecarboxamido)-6-methylisonicotinamide;

(R)—N-(2-((3-chloro-5-(trifluoromethyl)pyridin-2-yl)oxy)propyl)-2-isobutyramido-6-methylisonicotinamide;

2-methyl-6-propionamido-N-(2-((7-(trifluoromethyl)quinolin-4-yl)oxy)ethyl)isonicotinamide;

2-(cyclopropanecarboxamido)-N-(2-((7-(trifluoromethyl)quinolin-4-yl)oxy)ethyl)isonicotinamide;

2-isobutyramido-N-(2-((7-(trifluoromethyl)quinolin-4-yl)oxy)ethyl)isonicotinamide;

N-(2-((3-fluoro-5-(trifluoromethyl)pyridin-2-yl)oxy)ethyl)-2-methyl-6-propionamidoisonicotinamide;

N-(2-((5-chloro-3-(trifluoromethyl)pyridin-2-yl)oxy)ethyl)-2-methyl-6-propionamidoisonicotinamide;

2-propionamido-N-(2-((4-(trifluoromethyl)quinolin-2-yl)oxy)ethyl)isonicotinamide;

2-methyl-6-propionamido-N-(2-((4-(trifluoromethyl)quinolin-2-yl)oxy)ethyl)isonicotinamide;

2-isobutyramido-N-(2-((4-(trifluoromethyl)quinolin-2-yl)oxy)ethyl)isonicotinamide;

2-(cyclopropanecarboxamido)-N-(2-((4-(trifluoromethyl)quinolin-2-yl)oxy)ethyl)pyrimidine-4-carboxamide;

2-butyramido-N-(2-((3-chloro-5-(trifluoromethyl)pyridin-2-yl)oxy)ethyl)isonicotinamide;

N-(2-((3-chloro-5-(trifluoromethyl)pyridin-2-yl)oxy)ethyl)-2-pivalamidoisonicotinamide;

N-(2-((3-chloro-5-(trifluoromethyl)pyridin-2-yl)oxy)ethyl)-6-methyl-2-propionamidopyrimidine-4-carboxamide;

N-(2((3-chloro-5-(trifluoromethyl)pyridin-2-yl)oxy)ethyl)-2-isobutyramido-6-methylpyrimidine-4-carboxamide;

2-acetamido-N-(2-(2-fluoro-4-(trifluoromethyl)phenoxy)ethyl)isonicotinamide;

N-(2-(2-fluoro-4-(trifluoromethyl)phenoxy)ethyl)-2-propionamidoisonicotinamide;
2-acetamido-N-(2-(2-fluoro-4-(trifluoromethyl)phenoxy)ethyl)-6-methylisonicotinamide;
N-(2-(2-fluoro-4-(trifluoromethyl)phenoxy)ethyl)-2-methyl-6-propionamidoisonicotinamide;
2-(cyclopropanecarboxamido)-N-(2-(2-fluoro-4-(trifluoromethyl)phenoxy)ethyl)isonicotinamide;
N-(2-(2-fluoro-4-(trifluoromethyl)phenoxy)ethyl)-2-isobutyramidoisonicotinamide;
2-(cyclopropanecarboxamido)-N-(2-(2-fluoro-4-(trifluoromethyl)phenoxy)ethyl)-6-methylisonicotinamide;
N-(2-(2-fluoro-4-(trifluoromethyl)phenoxy)ethyl)-2-isobutyramido-6-methylisonicotinamide;
2-(cyclopropanecarboxamido)-N-(2-(2-fluoro-4-(trifluoromethyl)phenoxy)ethyl)pyrimidine-4-carboxamide;
N-(2-(4-chloro-3-(trifluoromethyl)phenoxy)ethyl)-2-methyl-6-propionamidoisonicotinamide;
N-(2-(4-chloro-3-(trifluoromethyl)phenoxy)ethyl)-2-isobutyramidoisonicotinamide;
N-(2-(4-chloro-3-(trifluoromethyl)phenoxy)ethyl)-2-isobutyramido-6-methylisonicotinamide;
N-(2-(2-chloro-5-(trifluoromethyl)phenoxy)ethyl)-2-methyl-6-propionamidoisonicotinamide;
N-(2-(2-chloro-5-(trifluoromethyl)phenoxy)ethyl)-2-isobutyramido-6-methylisonicotinamide;
N-(2-(2-chloro-4-(trifluoromethoxy)phenoxy)ethyl)-2-methyl-6-propionamidoisonicotinamide;
N-(2-(2-chloro-4-(trifluoromethoxy)phenoxy)ethyl)-2-(cyclopropanecarboxamido)isonicotinamide;
N-(2-(2-chloro-4-(trifluoromethoxy)phenoxy)ethyl)-2-isobutyramidoisonicotinamide;
N-(2-(2-chloro-4-(trifluoromethoxy)phenoxy)ethyl)-2-isobutyramido-6-methylisonicotinamide;
N-(1-((3-chloro-5-(trifluoromethyl)pyridin-2-yl)oxy)-2-methylpropan-2-yl)-2-propionamidoisonicotinamide;
N-(1-((3-chloro-5-(trifluoromethyl)pyridin-2-yl)oxy)-2-methylpropan-2-yl)-2-(cyclopropanecarboxamido)-6-methylpyrimidine-4-carboxamide;
N-(1-(((3-chloro-5-(trifluoromethyl)pyridin-2-yl)oxy)methyl)cyclopropyl)-2-isobutyramido-6-methylisonicotinamide;
N-(2-((3-cyano-5-(trifluoromethyl)pyridin-2-yl)oxy)ethyl)-2-methyl-6-propionamidoisonicotinamide;
2-acetamido-N-(2-(2-chloro-4-(trifluoromethoxy)phenoxy)ethyl)isonicotinamide;
N-(2-(2-chloro-4-(trifluoromethoxy)phenoxy)ethyl)-2-propionamidoisonicotinamide;
N-(2-(2-chloro-4-(trifluoromethoxy)phenoxy)ethyl)-2-(cyclopropanecarboxamido)-6-methylisonicotinamide;
2-acetamido-N-(2-(2-chloro-4-(trifluoromethoxy)phenoxy)ethyl)=6-methylisonicotinamide;
N-(2-(2-chloro-4-(trifluoromethoxy)phenoxy)ethyl)-2-(cyclopropanecarboxamido)pyrimidine-4-carboxamide;
2-acetamido-N-(3-((3-chloro-5-(trifluoromethyl)pyridin-2-yl)amino)propyl)isonicotinamide;
N-(3-((3-chloro-5-(trifluoromethyl)pyridin-2-yl)amino)propyl)-2-propionamidoisonicotinamide;
N-(3-((3-chloro-5-(trifluoromethyl)pyridin-2-yl)amino)propyl)-2-isobutyramidoisonicotinamide;
2-acetamido-N-(3-((3-chloro-5-(trifluoromethyl)pyridin-2-yl)amino)propyl)-6-methylisonicotinamide;
2-acetamido-N-(3-((3-chloro-5-(trifluoromethyl)pyridin-2-yl)oxy)propyl)isonicotinamide;
N-(3-((3-chloro-5-(trifluoromethyl)pyridin-2-yl)oxy)propyl)-2-isobutyramidoisonicotinamide;
2-acetamido-N-(3-((3-chloro-5-(trifluoromethyl)pyridin-2-yl)oxy)propyl)-6-methylisonicotinamide;
N-(3-((3-chloro-5-(trifluoromethyl)pyridin-2-yl)oxy)propyl)-2-(cyclopropanecarboxamido)-6-methylpyrimidine-4-carboxamide;
2-acetamido-N-(2-(2-methoxy-4-(trifluoromethyl)phenoxy)ethyl)isonicotinamide;
N-(2-(2-methoxy-4-(trifluoromethyl)phenoxy)ethyl)-2-propionamidoisonicotinamide;
2-acetamido-N-(2-(2-methoxy-4-(trifluoromethyl)phenoxy)ethyl)-6-methylisonicotinamide;
N-(2-(2-methoxy-4-(trifluoromethyl)phenoxy)ethyl)-2-methyl-6-propionamidoisonicotinamide;
2-(cyclopropanecarboxamido)-N-(2-(2-methoxy-4-(trifluoromethyl)phenoxy)ethyl)isonicotinamide;
2-isobutyramido-N-(2-(2-methoxy-4-(trifluoromethyl)phenoxy)ethyl)isonicotinamide;
2-(cyclopropanecarboxamido)-N-(2-(2-methoxy-4-(trifluoromethyl)phenoxy)ethyl)-6-methylisonicotinamide;
2-isobutyramido-N-(2-(2-methoxy-4-(trifluoromethyl)phenoxy)ethyl)-6-methylisonicotinamide;
2-(cyclopropanecarboxamido)-N-(2-(2-methoxy-4-(trifluoromethyl)phenoxy)ethyl)pyrimidine-4-carboxamide;
N-(1-(((3-chloro-5-(trifluoromethyl)pyridin-2-yl)oxy)methyl)cyclopropyl)-2-isobutyramido-6-methylpyrimidine-4-carboxamide;
N-(1-(((3-chloro-5-(trifluoromethyl)pyridin-2-yl)oxy)methyl)cyclopropyl)-2-(cyclopropanecarboxamido)-6-methylpyrimidine-4-carboxamide;
2-butyramido-N-(1-(((3-chloro-5-(trifluoromethyl)pyridin-2-yl)oxy)methyl)cyclopropyl)isonicotinamide;
2-acetamido-N-(2-(2-methyl-4-(trifluoromethyl)phenoxy)ethyl)isonicotinamide;
N-(2-(2-methyl-4-(trifluoromethyl)phenoxy)ethyl)-2-propionamidoisonicotinamide;
2-acetamido-6-methyl-N-(2-(2-methyl-4-(trifluoromethyl)phenoxy)ethyl)isonicotinamide;
2-methyl-N-(2-(2-methyl-4-(trifluoromethyl)phenoxy)ethyl)-6-propionamidoisonicotinamide;
2-(cyclopropanecarboxamido)-N-(2-(2-methyl-4-(trifluoromethyl)phenoxy)ethyl)isonicotinamide;
2-isobutyramido-N-(2-(2-methyl-4-(trifluoromethyl)phenoxy)ethyl)isonicotinamide;
2-(cyclopropanecarboxamido)-6-methyl-N-(2-(2-methyl-4-(trifluoromethyl)phenoxy)ethyl)isonicotinamide;
2-isobutyramido-6-methyl-N-(2-(2-methyl-4-(trifluoromethyl)phenoxy)ethyl)isonicotinamide;
2-(cyclopropanecarboxamido)-N-(2-(2-methyl-4-(trifluoromethyl)phenoxy)ethyl)pyrimidine-4-carboxamide;
N-(2-(4-chloro-3-(trifluoromethyl)phenoxy)ethyl)-2-(cyclopropanecarboxamido)-6-methylpyrimidine-4-carboxamide;
N-(2-(3-fluoro-4-(trifluoromethoxy)phenoxy)ethyl)-2-propionamidoisonicotinamide;
N-(2-(3-fluoro-4-(trifluoromethoxy)phenoxy)ethyl)-2-isobutyramidoisonicotinamide;
2-(cyclopropanecarboxamido)-N-(2-(3-fluoro-4-(trifluoromethoxy)phenoxy)ethyl)pyrimidine-4-carboxamide;
2-(cyclopropanecarboxamido)-N-(2-(3-fluoro-4-(trifluoromethoxy)phenoxy)ethyl)isonicotinamide;
2-acetamido-N-(2-(3-fluoro-4-(trifluoromethoxy)phenoxy)ethyl)-6-methylisonicotinamide;
2-(cyclopropanecarboxamido)-N-(2-(3-fluoro-4-(trifluoromethoxy)phenoxy)ethyl)-6-methylpyrimidine-4-carboxamide;

2-acetamido-N-(2-(3-fluoro-4-(trifluoromethoxy)phenoxy)ethyl)isonicotinamide; and
N-(2-(3-fluoro-4-(trifluoromethyl)phenoxy)ethyl)-2-isobutyramidoisonicotinamide;
or a prodrug thereof or a pharmaceutically acceptable salt thereof.

7. The compound as described in claim 6, which is selected from the group consisting of:
2-(cyclopropanecarboxamido)-N-(2-(4-(trifluoromethyl)phenoxy)propyl)isonicotinamide;
2-acetamido-N-(2-((3-chloro-5-(trifluoromethyl)pyridin-2-yl)amino)ethyl)isonicotinamide;
N-(2-((3-chloro-5-(trifluoromethyl)pyridin-2-yl)amino)ethyl)-2-propionamidoisonicotinamide;
2-acetamido-N-(2-((3-chloro-5-(trifluoromethyl)pyridin-2-yl)amino)ethyl)-6-methylisonicotinamide;
N-(2-((3-chloro-5-(trifluoromethyl)pyridin-2-yl)amino)ethyl)-2-methyl-6-propionamidoisonicotinamide;
N-(2-((3-chloro-5-(trifluoromethyl)pyridin-2-yl)amino)ethyl)-2-(cyclopropanecarbox amido)isonicotinamide;
N-(2-((3-chloro-5-(trifluoromethyl)pyridin-2-yl)amino)ethyl)-2-isobutyramidoisonicotinamide;
2-acetamido-N-(2-((3-chloro-5-(trifluoromethyl)pyridin-2-yl)oxy)ethyl)isonicotinamide;
N-(2-((3-chloro-5-(trifluoromethyl)pyridin-2-yl)oxy)ethyl)-2-propionamidoisonicotinamide;
2-acetamido-N-(2-((3-chloro-5-(trifluoromethyl)pyridin-2-yl)oxy)ethyl)-6-methylisonicotinamide;
2-acetamido-N-(2-((3-chloro-5-(trifluoromethyl)pyridin-2-yl)oxy)ethyl)-6-methylpyrimidine-4-carboxamide;
2-methyl-6-propionamido-N-(2-((5-(trifluoromethyl)pyridin-2-yl)oxy)ethyl)isonicotinamide;
N-(2-((3-chloro-5-(trifluoromethyl)pyridin-2-yl)oxy)ethyl)-2-isobutyramidoisonicotinamide;
N-(2-((a-chloro-5-(trifluoromethyl)pyridin-2-yl)oxy)ethyl)-2-(cyclopropanecarboxamido)isonicotinamide;
N-(2-((3-chloro-5-(trifluoromethyl)pyridin-2-yl)oxy)ethyl)-2-methyl-6-propionamidoisonicotinamide;
N-(2-((3-chloro-5-(trifluoromethyl)pyridin-2-yl)oxy)ethyl)-2-(cyclopropanecarboxamido)-6-methylpyrimidine-4-carboxamide;
(R)—N-(2-((3-chloro-5-(trifluoromethyl)pyridin-2-yl)oxy)propyl)-2-isobutyramidoisonicotinamide;
2-isobutyramido-N-(2-(3-(trifluoromethoxy)phenoxy)ethyl)isonicotinamide;
2-acetamido-6-methyl-N-(2-(3-(trifluoromethoxy)phenoxy)ethyl)isonicotinamide;
2-acetamido-N-(2-(2-chloro-4-(trifluoromethyl)phenoxy)ethyl)isonicotinamide;
N-(2-(2-chloro-4-(trifluoromethyl)phenoxy)ethyl)-2-propionamidoisonicotinamide;
N-(2-(2-chloro-4-(trifluoromethyl)phenoxy)ethyl)-2-isobutyramidoisonicotinamide;
2-acetamido-N-(2-(2-chloro-4-(trifluoromethyl)phenoxy)ethyl)-6-methylisonicotinamide;
2-acetamido-6-methyl-N-(2-(4-(trifluoromethyl)phenoxy)ethyl)isonicotinamide;
N-(2-((3-chloro-5-(trifluoromethyl)pyridin-2-yl)oxy)ethyl)-2-(cyclopropanecarboxamido)-6-methylisonicotinamide;
N-(2-((3-chloro-5-(trifluoromethyl)pyridin-2-yl)amino)ethyl)-2-(cyclopropanecarboxamido)-6-methylisonicotinamide;
N-(3-(3-chloro-5-(trifluoromethyl)pyridin-2-yl)propyl)-2-(cyclopropanecarboxamido)isonicotinamide;
2-acetamido-N-(3-(3-chloro-5-(trifluoromethyl)pyridin-2-yl)propyl)-6-methylisonicotinamide;
N-(2-((3-fluoro-5-(trifluoromethyl)pyridin-2-yl)oxy)ethyl)-2-isobutyramido-6-methylisonicotinamide;
N-(3-(3-chloro-5-(trifluoromethyl)pyridin-2-yl)propyl)-2-propionamidoisonicotinamide;
2-acetamido-6-methyl-N-(2-(4-(pentafluorosulfanyl)phenoxy)ethyl)isonicotinamide;
2-propionamido-N-(2-(4-(pentafluorosulfanyl)phenoxy)ethyl)isonicotinamide;
2-(cyclopropanecarboxamido)-N-(2-(4-(pentafluorosulfanyl)phenoxy)ethyl)isonicotinamide;
2-isobutyramido-N-(2-(4-(pentafluorosulfanyl)phenoxy)ethyl)isonicotinamide;
N-(2-((3-chloro-5-(trifluoromethyl)pyridin-2-yl)oxy)ethyl)-2-isobutyramido-6-methylisonicotinamide;
N-(2-((3-chloro-5-(trifluoromethyl)pyridin2-yl)oxy)ethyl)-2-(cyclopropanecarboxamido)pyrimidine-4-carboxamide;
N-(2-((3-chloro-5-(trifluoromethyl)pyridin-2-yl)amino)ethyl)-2-isobutyramido-6-methylisonicotinamide;
N-(2-((3-chloro-5-(trifluoromethyl)pyridin-2-yl)amino)ethyl)-2-(cyclopropanecarboxamido)pyrimidine-4-carboxamide;
N-(2-(2-chloro-4-(trifluoromethyl)phenoxy)ethyl)-2-methyl-6-propionamidoisonicotinamide;
N-(2-(2-chloro-4-(trifluoromethyl)phenoxy)ethyl)-2-(cyclopropanecarboxamido)isonicotinamide;
N-(2-(2-chloro-4-(trifluoromethyl)phenoxy)ethyl)-2-(cyclopropanecarboxamido)-6-methylisonicotinamide;
N-(2-(2-chloro-4-(trifluoromethyl)phenoxy)ethyl)-2-isobutyramido-6-methylisonicotinamide;
N-(2-(2-chloro-4-(trifluoromethyl)phenoxy)ethyl)-2-(cyclopropanecarboxamido)pyrimidine-4-carboxamide;
2-acetamido-N-(2-((3-chloro-5-(trifluoromethyl)pyridin-2-yl)thio)ethyl)isonicotinamide;
N-(2-((3-chloro-5-(trifluoromethyl)pyridin-2-yl)thio)ethyl)-2-isobutyramidoisonicotinamide;
2-acetamido-N-(2-((3-chloro-5-(trifluoromethyl)pyridin-2-yl)thio)ethyl)-6-methylisonicotinamide;
N-(2-((3-chloro-5-(trifluoromethyl)pyridin-2-yl)thio)ethyl)-2-methyl-6-propionamidoisonicotinamide;
(R)-2-acetamido-N-(1-((3-chloro-5-(trifluoromethyl)pyridin-2-yl)oxy)propan-2-yl)isonicotinamide;
(R)—N-(1-((3-chloro-5-(trifluoromethyl)pyridin-2-yl)oxy)propan-2-yl)-2-propionamidoisonicotinamide;
(R)-2-acetamido-N-(1-((3-chloro-5-(trifluoromethyl)pyridin-2-yl)oxy)propan-2-yl)-6-methylisonicotinamide;
(R)—N-(1-((3-chloro-5-(trifluoromethyl)pyridin-2-yl)oxy)propan-2-yl)-2-methyl-6-propionamidoisonicotinamide;
(R)—N-(1-((3-chloro-5-(trifluoromethyl)pyridin-2-yl)oxy)propan-2-yl)-2-(cyclopropanecarboxamido)isonicotinamide;
(R)—N-(1-((3-chloro-5-(trifluoromethyl)pyridin-2-yl)oxy)propan-2-yl)-2-isobutyramidoisonicotinamide;
(R)—N-(1-((3-chloro-5-(trifluoromethyl)pyridin-2-yl)oxy)propan-2-yl)-2-(cyclopropanecarboxamido)-6-methylisonicotinamide;
(R)—N-(1-((3-chloro-5-(trifluoromethyl)pyridin-2-yl)oxy)propan-2-yl)-2-isobutyramido-6-methylisonicotinamide;
(R)—N-(1-((3-chloro-5-(trifluoromethyl)pyridin-2-yl)oxy)propan-2-yl)-2-(cyclopropanecarboxamido)pyrimidine-4-carboxamide;
(S)—N-(2-((3-chloro-5-(trifluoromethyl)pyridin-2-yl)oxy)propyl)-2-methyl-6-propionamidoisonicotinamide;

(R)-2-acetamido-N-(2-((3-chloro-5-(trifluoromethyl)pyridin-2-yl)oxy)propyl)-6-methylisonicotinamide;
(R)—N-(2-((3-chloro-5-(trifluoromethyl)pyridin-2-yl)oxy)propyl)-2-methyl-6-propionamidoisonicotinamide;
(R)—N-(2-((3-chloro-5-(trifluoromethyl)pyridin-2-yl)oxy)propyl)-2-(cyclopropanecarboxamido)isonicotinamide;
(R)—N-(2-((3-chloro-5-(trifluoromethyl)pyridin-2-yl)oxy)propyl)-2-(cyclopropanecarboxamido)-6-methylisonicotinamide;
(R)—N-(2-((3-chloro-5-(trifluoromethyl)pyridin-2-yl)oxy)propyl)-2-isobutyramido-6-methylisonicotinamide;
N-(2-((3-fluoro-5-(trifluoromethyl)pyridin-2-yl)oxy)ethyl)-2-methyl-6-propionamidoisonicotinamide;
N-(2-((5-chloro-3-(trifluoromethyl)pyridin-2-yl)oxy)ethyl)-2-methyl-6-propionamidoisonicotinamide;
2-butyramido-N-(2-((3-chloro-5-(trifluoromethyl)pyridin-2-yl)oxy)ethyl)isonicotinamide;
N-(2-((3-chloro-5-(trifluoromethyl)pyridin-2-yl)oxy)ethyl)-2-pivalamidoisonicotinamide;
N-(2-((3-chloro-5-(trifluoromethyl)pyridin-2-yl)oxy)ethyl)-6-methyl-2-propionamidopyrimidine-4-carboxamide;
N-(2-((3-chloro-5-(trifluoromethyl)pyridin-2-yl)oxy)ethyl)-2-isobutyramido-6-methylpyrimidine-4-carboxamide;
2-acetamido-N-(2-(2-fluoro-4-(trifluoromethyl)phenoxy)ethyl)isonicotinamide;
N-(2-(2-fluoro-4-(trifluoromethyl)phenoxy)ethyl)-2-propionamidoisonicotinamide;
2-acetamido-N-(2-(2-fluoro-4-(trifluoromethyl)phenoxy)ethyl)-6-methylisonicotinamide;
N-(2-(2-fluoro-4-(trifluoromethyl)phenoxy)ethyl)-2-methyl-6-propionamidoisonicotinamide;
2-(cyclopropanecarboxamido)-N-(2-(2-fluoro-4-(trifluoromethyl)phenoxy)ethyl)isonicotinamide;
N-(2-(2-fluoro-4-(trifluoromethyl)phenoxy)ethyl)-2-isobutyramidoisonicotinamide;
2-(cyclopropanecarboxamido)-N-(2-fluoro-4-(trifluoromethyl)phenoxy)ethyl)-6-methylisonicotinamide;
N-(2-(2-fluoro-4-(trifluoromethyl)phenoxy)ethyl)-2-isobutyramido-6-methylisonicotinamide;
2-(cyclopropanecarboxamido)-N-(2-(2-fluoro-4-(trifluoromethyl)phenoxy)ethyl)pyrimidine-4-carboxamide;
N-(2-(4-chloro-3-(trifluoromethyl)phenoxy)ethyl)-2-methyl-6-propionamidoisonicotinamide;
N-(2-(4-chloro-3-(trifluoromethyl)phenoxy)ethyl)-2-isobutyramidoisonicotinamide;
N-(2-(4-chloro-3-(trifluoromethyl)phenoxy)ethyl)-2-isobutyramido-6-methylisonicotinamide;
N-(2-(2-chloro-5-(trifluoromethyl)phenoxy)ethyl)-2-methyl-6-propionamidoisonicotinamide;
N-(2-(2-chloro-5-(trifluoromethyl)phenoxy)ethyl)-2-isobutyramido-6-methylisonicotinamide;
N-(2-(2-chloro-4-(trifluoromethoxy)phenoxy)ethyl)-2-methyl-6-propionamidoisonicotinamide;
N-(2-(2-chloro-4-(trifluoromethoxy)phenoxy)ethyl)-2-(cyclopropanecarboxamido)isonicotinamide;
N-(2-(2-chloro-4-(trifluoromethoxy)phenoxy)ethyl)-2-isobutyramidoisonicotinamide;
N-(2-(2-chloro-4-(trifluoromethoxy)phenoxy)ethyl)-2-isobutyramidomethylisonicotinamide;
N-(1-((3-chloro-5-(trifluoromethyl)pyridin-2-yl)oxy)-2-methylpropan-2-yl)-2-propionamidoisonicotinamide;
N-(1-((3-chloro-5-(trifluoromethyl)pyridin-2-yl)oxy)-2-methylpropan-2-yl)-2-(cyclopropanecarboxamido)-6-methylpyrimidine-4-carboxamide;
N-(1-(((3-chloro-5-(trifluoromethyl)pyridin-2-yl)oxy)methyl)cyclopropyl)-2-isobutyramido-6-methylisonicotinamide;
N-(2-((3-cyano-5-(trifluoromethyl)pyridin-2-yl)oxy)ethyl)-2-methyl-6-propionamidoisonicotinamide;
2-acetamido-N-(2-(2-chloro-4-(trifluoromethoxy)phenoxy)ethyl)isonicotinamide;
N-(2-(2-chloro-4-(trifluoromethoxy)phenoxy)ethyl)-2-propionamidoisonicotinamide;
N-(2-(2-chloro-4-(trifluoromethoxy)phenoxy)ethyl)-2-(cyclopropanecarboxamido)-6-methylisonicotinamide;
2-acetamido-N-(2-(2-chloro-4-(trifluoromethoxy)phenoxy)ethyl)-6-methylisonicotinamide;
N-(2-(2-chloro-4-(trifluoromethoxy)phenoxy)ethyl)-2-(cyclopropanecarboxamido)pyrimidine-4-carboxamide;
2-acetamido-N-(3-((3-chloro-5-(trifluoromethyl)pyridin-2-yl)amino)propyl)isonicotinamide;
N-(3-((3-chloro-5-(trifluoromethyl)pyridin-2-yl)amino)propyl)-2-propionamidoisonicotinamide;
N-(3-((3-chloro-5-(trifluoromethyl)pyridin-2-yl)amino)propyl)-2-isobutyramidoisonicotinamide;
2-acetamido-N-(3-((3-chloro-5-(trifluoromethyl)pyridin-2-yl)amino)propyl)-6-methylisonicotinamide;
2-acetamido-N-(3-((3-chloro-5-(trifluoromethyl)pyridin-2-yl)oxy)propyl)isonicotinamide;
N-(3-((3-chloro-5-(trifluoromethyl)pyridin-2-yl)oxy)propyl)-2-isobutyramidoisonicotinamide;
2-acetamido-N-(3-((3-chloro-5-(trifluoromethyl)pyridin-2-yl)oxy)propyl)-6-methylisonicotinamide;
N-(343-chloro-5-(trifluoromethyl)pyridin-2-yl)oxy)propyl)-2-(cyclopropanecarboxamido)-6-methylpyrimidine-4-carboxamide;
2-acetamido-N-(2-(2-methoxy-4-(trifluoromethyl)phenoxy)ethyl)isonicotinamide;
N-(2-(2-methoxy-4-(trifluoromethyl)phenoxy)ethyl)-2-propionamidoisonicotinamide;
2-acetamido-N-(2-(2-methoxy-4-(trifluoromethyl)phenoxy)ethyl)-6-methylisonicotinamide;
N-(2-(2-methoxy-4-(trifluoromethyl)phenoxy)ethyl)-2-methyl-6-propionamidoisonicotinamide;
2-(cyclopropanecarboxamido)-N-(2-(2-methoxy-4-(trifluoromethyl)phenoxy)ethyl)isonicotinamide;
2-isobutyramido-N-(2-(2-methoxy-4-(trifluoromethyl)phenoxy)ethyl)isonicotinamide;
2-(cyclopropanecarboxamido)-N-(2-(2-methoxy-4-(trifluoromethyl)phenoxy)ethyl)-6-methylisonicotinamide;
2-isobutyramido-N-(2-(2-methoxy-4-(trifluoromethyl)phenoxy)ethyl)-6-methylisonicotinamide;
2-(cyclopropanecarboxamido)-N-(2-(2-methoxy-4-(trifluoromethyl)phenoxy)ethyl)pyrimidine-4-carboxamide;
N-(1-(((3-chloro-5-(trifluoromethyl)pyridin-2-yl)oxy)methyl)cyclopropyl)-2-isobutyramido-6-methylpyrimidine-4-carboxamide;
N-(1-(((3-chloro-5-(trifluoromethyl)pyridin-2-yl)oxy)methyl)cyclopropyl)-2-(cyclopropanecarboxamido)-6-methylpyrimidine-4-carboxamide;
2-butyramido-N-(1-(((3-chloro-5-(trifluoromethyl)pyridin-2-yl)oxy)methyl)cyclopropyl)isonicotinamide;
2-acetamido-N-(2-(2-methyl-4-(trifluoromethyl)phenoxy)ethyl)isonicotinamide;
N-(2-(2-methyl-4-(trifluoromethyl)phenoxy)ethyl)-2-propionamidoisonicotinamide;

2-acetamido-6-methyl-N-(2-(2-methyl-4-(trifluoromethyl)phenoxy)ethyl)isonicotinamide;
2-methyl-N-(2-(2-methyl-4-(trifluoromethyl)phenoxy)ethyl)-6-propionamidoisonicotinamide;
2-(cyclopropanecarboxamido)-N-(2-(2-methyl-4-(trifluoromethyl)phenoxy)ethyl)isonicotinamide;
2-isobutyramido-N-(2-(2-methyl-4-(trifluoromethyl)phenoxy)ethyl)isonicotinamide;
2-(cyclopropanecarboxamido)-6-methyl-N-(2-(2-methyl-4-(trifluoromethyl)phenoxy)ethyl)isonicotinamide;
2-isobutyramido-6-methyl-N-(2-(2-methyl-4-(trifluoromethyl)phenoxy)ethyl)isonicotinamide;
2-(cyclopropanecarboxamido)-N-(2-(2-methyl-4-(trifluoromethyl)phenoxy)ethyl)pyrimidine-4-carboxamide;
N-(2-(3-fluoro-4-(trifluoromethoxy)phenoxy)ethyl)-2-propionamidoisonicotinamide;
N-(2-(3-fluoro-4-(trifluoromethoxy)phenoxy)ethyl)-2-isobutyramidoisonicotinamide;
2-(cyclopropanecarboxamido)-N-(2-(3-fluoro-4-(trifluoromethoxy)phenoxy)ethyl)pyrimidine-4-carboxamide;
2-(cyclopropanecarboxamido)-N-(2-(3-fluoro-4-(trifluoromethoxy)phenoxy)ethyl)isonicotinamide;
2-acetamido-N-(2-(3-fluoro-4-(trifluoromethoxy)phenoxy)ethyl)-6-methylisonicotinamide;
2-acetamido-N-(2-(3-fluoro-4-(trifluoromethoxy)phenoxy)ethyl)isonicotinamide; and
N-(2-(3-fluoro-4-(trifluoromethyl)phenoxy)ethyl)-2-isobutyramidoisonicotinamide;
or a prodrug thereof or a pharmaceutically acceptable salt thereof.

8. A pharmaceutical composition comprising a compound or a pharmaceutically acceptable salt thereof, as described in claim 1, and a pharmaceutically acceptable carrier.

9. The pharmaceutical composition as described in claim 8, further comprising another pharmacologically active agent.

10. A method for the treatment of a condition or disorder in which Nav1.7 and Nav1.8 channel blockers are involved in an animal or a human, which comprises administering to the animal or human in need of such treatment a therapeutically effective amount of a compound or a pharmaceutically acceptable salt thereof, as described in claim 1, wherein the condition or disorder is at least one selected from the group consisting of: acute pain, chronic pain, neuropathic pain, inflammatory pain, visceral pain, nociceptive pain, pruritus, osteoarthritis, diabetic neuropathy, peripheral neuropathic pain, sciatica, epilepsy, an epileptic condition, a psychiatric disorder, trigeminal neuralgia, herpetic neuralgia, postherpetic neuralgia, severe pain, and chemo-induced pain.

11. A process for preparing a pharmaceutical composition comprising mixing a compound or a pharmaceutically acceptable salt thereof, as described in claim 1, and a pharmaceutically acceptable carrier or excipient.

12. The method as described in claim 10, wherein the psychiatric disorder is at least one selected from the group consisting of anxiety and depression.

* * * * *

UNITED STATES PATENT AND TRADEMARK OFFICE
CERTIFICATE OF CORRECTION

| | |
|---|---|
| PATENT NO. | : 11,154,544 B2 |
| APPLICATION NO. | : 16/301691 |
| DATED | : October 26, 2021 |
| INVENTOR(S) | : Yamagishi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 300 days.

Signed and Sealed this
Seventeenth Day of May, 2022

Katherine Kelly Vidal
*Director of the United States Patent and Trademark Office*